United States Patent
Diebold et al.

(10) Patent No.: US 7,956,185 B2
(45) Date of Patent: Jun. 7, 2011

(54) CYCLOBUT-3-ENE-1,2,-DIONE INHIBITORS OF POLO-LIKE KINASES

(75) Inventors: Robert B. Diebold, Waltham, MA (US);
Stevan W. Djuric, Libertyville, IL (US);
Vincent L. Giranda, Gurnee, IL (US);
Laura A. Hexamer, Grayslake, IL (US);
Nan-Horng Lin, Vernon Hills, IL (US);
Julie M. Miyashiro, Morton Grove, IL (US); Thomas D. Penning, Elmhurst, IL (US); Magdalena Przytulinska, Chicago, IL (US); Thomas J. Sowin, Wadsworth, IL (US); Gerard M. Sullivan, Lake Villa, IL (US); Zhi-Fu Tao, Gurnee, IL (US); Yunsong Tong, Libertyville, IL (US); Anil Vasudevan, Union Grove, WI (US); Le Wang, Vernon Hills, IL (US); Keith W. Woods, Libertyville, IL (US); Zhiren Xia, Gurnee, IL (US); Henry Q. Zhang, Grayslake, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 11/753,279

(22) Filed: May 24, 2007

(65) Prior Publication Data
US 2008/0015192 A1    Jan. 17, 2008

Related U.S. Application Data

(60) Provisional application No. 60/803,313, filed on May 26, 2006.

(51) Int. Cl.
*C07D 239/02* (2006.01)

(52) U.S. Cl. ........ 544/297; 544/162; 544/211; 544/402; 546/159; 546/246; 546/268.1; 548/127; 548/128; 548/161; 548/202; 548/235; 548/257; 548/262.2; 548/307.4; 548/346.1; 548/362.1; 548/373.1; 548/470; 548/503; 548/517; 549/49; 549/80; 549/471; 585/23

(58) Field of Classification Search ............ 544/162, 544/211, 297, 402; 546/159, 246, 268.1; 548/127, 128, 161, 202, 235, 257, 262.2, 548/307.4, 346.1, 362.1, 373.1, 470, 503, 548/517; 549/49, 80, 471; 585/23
See application file for complete search history.

(56) References Cited

U.S. PATENT DOCUMENTS
5,354,763  A    10/1994  Butera et al.
6,251,912  B1 *  6/2001  Wissner et al. ............ 514/228.2

FOREIGN PATENT DOCUMENTS
EP    0591891         4/1994
EP    1000039         5/2000
JP    06092915     *  4/1994
JP    H06-92915       4/1994
WO    02062761        8/2002
WO    2005019193      3/2005

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Cross & Klyne: International Union of Pure and Applied Chemistry, vol. 45, p. 13, 1976.
Butera, et al., "Design and SAR of Novel Potassium Channel Openers Targeted for Urge Urinary Incontinence. 1. N-Cyanoguanidine Bioisosteres Possessing in Vivo Bladder Selectivity", J. Med. Chem. 2000, vol. 43, p. 1187-1202.

* cited by examiner

*Primary Examiner* — James O Wilson
*Assistant Examiner* — Douglas M Willis
(74) *Attorney, Agent, or Firm* — Susan L. Steele; Gregory B. Donner; Gregory W. Steele

(57) ABSTRACT

Compounds of formula (I)

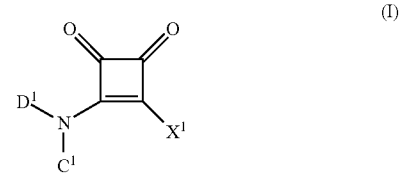

where $X^1$, $C^1$, and $D^1$ are defined herein, are inhibitors of polo-like kinases. The compounds of formula (I) are useful for treatment of diseases of cellular proliferation, such as, for example, cancer.

5 Claims, No Drawings

CYCLOBUT-3-ENE-1,2,-DIONE INHIBITORS OF POLO-LIKE KINASES

CROSS-REFERENCE TO RELATED APPLICATIONS

This application claims priority to commonly-owned U.S. Provisional Patent Application Ser. No. 60/803,313, filed May 26, 2006.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATED-BY-REFERENCE OF MATERIAL SUBMITTED ON A COMPACT DISC

Not Applicable.

BACKGROUND OF THE INVENTION

This invention pertains to compounds that inhibit Plk1, compositions containing the compounds and methods of treating diseases using the compounds.

Polo-like kinases (Plk's) are important in mitotic progression, and are therefore important for cell proliferation. For example, Plk1 is essential for the proper function of bipolar spindles and chromosomal segregation during metaphase of cell division. Plk1 depletion causes a defect in the attachment between the mitotic spindles and centrosomes, causing these cells to accumulate during mitosis then die. Because inhibition of Plk1 causes mitotic arrest, inhibitors of Plk1 have the potential to be cytotoxic agents that are useful for treatment of diseases of cellular proliferation, such as, for example, cancer.

BRIEF SUMMARY OF THE INVENTION

One embodiment of this invention, therefore, comprises compounds which inhibit polo-like kinases, the compounds having formula (I)

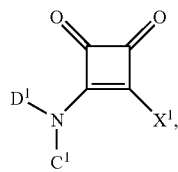

and therapeutically acceptable salts, prodrugs and salts of prodrugs thereof, wherein $X^1$ is $X^2$, $OX^2$, $SX^2$, $S(O)X^2$, $SO_2X^2$ or $N(A^1)(B^1)$;

$X^2$ is $X^3$, $X^4$, $X^5$ or $X^6$;

$X^3$ is phenyl which is unfused or fused with benzene, heteroarene or $X^{3,A}$; $X^{3,A}$ is cycloalkane, cycloalkene, heterocycloalkane or heterocycloalkene;

$X^4$ is heteroaryl which is unfused or fused with benzene, heteroarene or $X^{4,A}$; $X^{4,A}$ is cycloalkane, cycloalkene, heterocycloalkane or heterocycloalkene;

$X^5$ is cycloalkyl, cycloalkenyl, heterocycloalkyl or heterocycloalkenyl, each of which is unfused or fused with benzene, heteroarene or $X^{5,A}$; $X^{5,A}$ is cycloalkane, cycloalkene, heterocycloalkane or heterocycloalkene;

$X^6$ is alkyl, alkenyl or alkynyl, each of which is unsubstituted or substituted with phenyl, furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyrimidinyl, pyrrolyl, 1,2,4-thiadiazolyl, thiazolyl, thiophenyl, triazinyl or 1,2,3-triazolyl;

$A^1$ and $B^1$ are independently selected H, $R^1$, $C(O)R^1$, $C(O)OR^1$, $C(O)NHR^1$, $C(O)N(R^1)_2$, $SO_2NHR^1$ or $SO_2N(R^1)_2$;

$R^1$ is $R^2$, $R^3$, $R^4$ or $R^5$;

$R^2$ is phenyl which is unfused or fused with benzene, heteroarene or $R^{2,A}$; $R^{2,A}$ is cycloalkane, cycloalkene, heterocycloalkane or heterocycloalkene;

$R^3$ is heteroaryl which is unfused or fused with benzene, heteroarene or $R^{3,A}$; $R^{3,A}$ is cycloalkane, cycloalkene, heterocycloalkane or heterocycloalkene;

$R^4$ is cycloalkyl, cycloalkenyl, heterocycloalkyl or heterocycloalkenyl, each of which is unfused or fused with benzene, heteroarene or $R^{4,A}$; $R^{4,A}$ is cycloalkane, cycloalkene, heterocycloalkane or heterocycloalkene;

$R^5$ is alkyl, alkenyl or alkynyl, each of which is unsubstituted or substituted with one or two or three of independently selected $R^6$, $OR^6$, $C(O)OR^6$, $C(O)NH_2$, $C(O)NHR^6$, $C(O)N(R^6)_2$, $NHC(O)R^6$, $NR^6C(O)R^6$, $OH$, $(O)$, $CN$, $NH_2$, $NHR^6$, $N(R^6)_2$, F, Cl, Br or I;

$R^6$ is $R^7$, $R^8$ or $R^9$;

$R^7$ is phenyl which is unfused or fused with benzene, heteroarene or $R^{7,A}$; $R^{7,A}$ is cycloalkane, cycloalkene, heterocycloalkane or heterocycloalkene;

$R^8$ is heteroaryl which is unfused or fused with benzene, heteroarene or $R^{8,A}$; $R^{8,A}$ is cycloalkane, cycloalkene, heterocycloalkane or heterocycloalkene;

$R^9$ is cycloalkyl, cycloalkenyl, heterocycloalkyl or heterocycloalkenyl, each of which is unfused or fused with benzene, heteroarene or $R^{9,A}$; $R^{9,A}$ is cycloalkane, cycloalkene, heterocycloalkane or heterocycloalkene;

$C^1$ is H, $R^{10}$, $C(O)R^{10}$, $C(O)OR^{10}$, $C(O)NHR^{10}$, $C(O)N(R^{10})_2$, $SO_2NHR^{10}$ or $SO_2N(R^{10})_2$;

$R^{10}$ is $R^{11}$, $R^{12}$, $R^{13}$ or $R^{14}$;

$R^{11}$ is phenyl which is unfused or fused with benzene, heteroarene or $R^{11,A}$; $R^{11,A}$ is cycloalkane, cycloalkene, heterocycloalkane or heterocycloalkene;

$R^{12}$ is heteroaryl which is unfused or fused with benzene, heteroarene or $R^{12,A}$; $R^{12,A}$ is cycloalkane, cycloalkene, heterocycloalkane or heterocycloalkene;

$R^{13}$ is cycloalkyl, cycloalkenyl, heterocycloalkyl or heterocycloalkenyl, each of which is unfused or fused with benzene, heteroarene or $R^{13,A}$; $R^{13,A}$ is cycloalkane, cycloalkene, heterocycloalkane or heterocycloalkene;

$R^{14}$ is alkyl, alkenyl or alkynyl, each of which is unsubstituted or substituted with one or two or three of independently selected $R^{14,A}$, $OR^{14,A}$, $C(O)OR^{14,A}$, $C(O)NH_2$, $C(O)NHR^{14,A}$ $C(O)N(R^{14,A})_2$, $NHC(O)R^{14,A}$, $C(O)R^{14,A}$, $OH$, $CN$, $NH_2$, $NHR^{14,A}$, $N(R^{14,A})_2$, F, Cl, Br or I;

$R^{14,A}$ is $R^{15}$, $R^{16}$ or $R^{17}$;

$R^{15}$ is phenyl which is unfused or fused with benzene, heteroarene or $R^{15,A}$; $R^{15,A}$ is cycloalkane, cycloalkene, heterocycloalkane or heterocycloalkene;

$R^{16}$ is heteroaryl which is unfused or fused with benzene, heteroarene or $R^{16,A}$; $R^{16,A}$ is cycloalkane, cycloalkene, heterocycloalkane or heterocycloalkene;

$R^{17}$ is cycloalkyl, cycloalkenyl, heterocycloalkyl or heterocycloalkenyl, each of which is unfused or fused with benzene, heteroarene or $R^{17A}$; $R^{17A}$ is cycloalkane, cycloalkene, heterocycloalkane or heterocycloalkene;

$D^1$ is $R^{18}$, $R^{19}$ or $R^{20}$;

$R^{18}$ is pyrimidinyl which is unfused or fused with benzene, heteroarene or $R^{18A}$ and unsubstituted or substituted with one or two or three of independently selected CN, $NO_2$, F, Cl, Br or I; $R^{18A}$ is cycloalkane, cycloalkene, heterocycloalkane or heterocycloalkene;

$R^{19}$ is pyridinyl which is unfused or fused with benzene, heteroarene or $R^{19A}$ and substituted with $OR^{21}$, $SR^{21}$, $SO_2R^{21}$ or $NHR^{21}$; $R^{19A}$ is cycloalkane, cycloalkene, heterocycloalkane or heterocycloalkene;

$R^{20}$ is furanyl, imidazolyl, isothiazolyl, isoxazolyl, 1,2,3-oxadiazoyl, 1,2,5-oxadiazoyl, oxazolyl, pyrazinyl, pyrazolyl, pyridazinyl, pyrimidinyl, pyrrolyl, 1,2,4-thiadiazolyl, thiazolyl, thiophenyl, triazinyl or 1,2,3-triazolyl, each of which is unfused or fused with benzene or heteroaryl and substituted with $R^{21}$, $OR^{21}$, $SR^{21}$, $SO_2R^{21}$, $NHR^{21}$ or $N(CH_3)R^{21}$;

$R^{21}$ is $R^{22}$, $R^{23}$, $R^{24}$ or $R^{25}$;

$R^{22}$ is phenyl which is unfused or fused with benzene, heteroarene or $R^{22A}$; $R^{22A}$ is cycloalkane, cycloalkene, heterocycloalkane or heterocycloalkene;

$R^{23}$ is heteroaryl which is unfused or fused with benzene, heteroarene or $R^{23A}$; $R^{23A}$ is cycloalkane, cycloalkene, heterocycloalkane or heterocycloalkene;

$R^{24}$ is cycloalkyl, cycloalkenyl, heterocycloalkyl or heterocycloalkenyl, each of which is unfused or fused with benzene, heteroarene or $R^{24A}$; $R^{24A}$ is cycloalkane, cycloalkene, heterocycloalkane or heterocycloalkene;

$R^{25}$ is alkyl, alkenyl or alkynyl, each of which is unsubstituted or substituted with one or two or three of independently selected $R^{26}$, $OR^{26}$, $C(O)OR^{26}$, $C(O)NH_2$, $C(O)NHR^{26}$, $C(O)N(R^{26})_2$, $NHC(O)R^{26}$, $NR^{26}C(O)R^{26}$, OH, CN, $NH_2$, $NHR^{26}$, $N(R^{26})_2$, F, Cl, Br or I;

$R^{26}$ is $R^{27}$, $R^{28}$ or $R^{29}$;

$R^{27}$ is phenyl which is unfused or fused with benzene, heteroarene or $R^{27A}$; $R^{27A}$ is cycloalkane, cycloalkene, heterocycloalkane or heterocycloalkene;

$R^{28}$ is heteroaryl which is unfused or fused with benzene, heteroarene or $R^{28A}$; $R^{28A}$ is cycloalkane, cycloalkene, heterocycloalkane or heterocycloalkene;

$R^{29}$ is cycloalkyl, cycloalkenyl, heterocycloalkyl or heterocycloalkenyl, each of which is unfused or fused with benzene, heteroarene or $R^{29A}$; $R^{29A}$ is cycloalkane, cycloalkene, heterocycloalkane or heterocycloalkene;

each foregoing cyclic moiety is independently unsubstituted, further unsubstituted, substituted or further substituted with one or two or three or four or five of independently selected $R^{30}$, $OR^{30}$, $SR^{30}$, $S(O)R^{30}$, $SO_2R^{30}$, $C(O)R^{30}$, $CO(O)R^{30}$, $OC(O)R^{30}$, $OC(O)OR^{30}$, $NH_2$, $NHR^{30}$, $N(R^{30})_2$, $C(O)NH_2$, $C(O)NHR^{30}$, $C(O)N(R^{30})_2$, $SO_2NH_2$, $SO_2NHR^{30}$, $NHSO_2R^{30}$, $N(R^{30})SO_2R^{30}$, $SO_2N(R^{30})_2$, $CF_3$, $CF_2CF_3$, C(O)H, CN, C(O)OH, (O), OH, $NO_2$, $CF_3$, $CF_2CF_3$, $OCF_3$, $OCF_2CF_3$, F, Cl, Br or I;

$R^{30}$ is $R^{31}$, $R^{32}$, $R^{33}$ or $R^{34}$;

$R^{31}$ is phenyl which is unfused or fused with benzene, heteroarene or $R^{31A}$; $R^{31A}$ is cycloalkane, cycloalkene, heterocycloalkane or heterocycloalkene;

$R^{32}$ is heteroaryl which is unfused or fused with benzene, heteroarene or $R^{32A}$; $R^{32A}$ is cycloalkane, cycloalkene, heterocycloalkane or heterocycloalkene;

$R^{33}$ is cycloalkyl, cycloalkenyl, heterocycloalkyl or heterocloalkenyl, each of which is unfused or fused with benzene, heteroarene or $R^{33A}$; $R^{33A}$ is cycloalkane, cycloalkene, heterocycloalkane or heterocycloalkene;

$R^{34}$ is alkyl, alkenyl or alkynyl, each of which is unsubstituted or substituted with one or two or three of independently selected $R^{35}$, $OR^{35}$, $SR^{35}$, $C(O)OR^{35}$, $NH_2$, $NHR^{35}$, OH, $N(R^{35})_2$, $C(O)NH_2$, $C(O)NHR^{35}$, $C(O)N(R^{35})_2$, $NHC(O)R^{35}$, $N(R^{35})C(O)R^{35}$, F, Cl, Br or I;

$R^{35}$ is $R^{36}$, $R^{37}$, $R^{38}$ or $R^{39}$;

$R^{36}$ is phenyl which is unfused or fused with benzene, heteroarene or $R^{36A}$; $R^{36A}$ is cycloalkane, cycloalkene, heterocycloalkane or heterocycloalkene;

$R^{37}$ is heteroaryl which is unfused or fused with benzene, heteroarene or $R^{37A}$; $R^{37A}$ is cycloalkane, cycloalkene, heterocycloalkane or heterocycloalkene;

$R^{38}$ is cycloalkyl, cycloalkenyl, heterocycloalkyl or heterocloalkenyl, each of which is unfused or fused with benzene, heteroarene or $R^{38A}$; $R^{38A}$ is cycloalkane, cycloalkene, heterocycloalkane or heterocycloalkene;

the moieties represented by $R^{31-33}$ and $R^{36-38}$ are independently unsubstituted or substituted with one, two, three four or five of independently substituted $R^{39}$, $OR^{39}$, C(O) $OR^{39}NH_2$, $NHR^{39}$, $N(R^{39})_2$, $C(O)NH_2$, $C(O)NHR^{39}$, $C(O)N(R^{39})_2$, $NHC(O)R^{39}$, $N(R^{39})C(O)R^{39}$, $SO_2NH_2$, $SO_2NHR^{39}$, $SO_2N(R^{39})_2$, (O), CN, F, Cl, Br or I; and $R^{39}$ is alkyl, alkenyl or alkynyl, each of which is unsubstituted or substituted with phenyl, furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyrimidinyl, pyrrolyl, 1,2,4-thiadiazolyl, thiazolyl, thiophenyl, triazinyl or 1,2,3-triazolyl.

Another embodiment comprises compounds having formula (I), and therapeutically acceptable salts, prodrugs and salts of prodrugs thereof, wherein $X^1$ is $X^2$, $SX^2$ or $N(A^1)(B^1)$;

$X^2$ is $X^3$, $X^4$, $X^5$ or $X^6$ $X^3$ is phenyl which is unfused or fused with benzene or heteroarene;

$X^4$ is heteroaryl which is unfused or fused with benzene or heteroarene;

$X^5$ is cycloalkyl, cycloalkenyl, heterocycloalkyl or heterocycloalkenyl, each of which is unfused or fused with benzene or heteroarene;

$X^6$ is alkyl, alkenyl or alkynyl, each of which is unsubstituted or substituted with phenyl, furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyrimidinyl, pyrrolyl, 1,2,4-thiadiazolyl, thiazolyl, thiophenyl, triazinyl or 1,2,3-triazolyl;

$A^1$ and $B^1$ are independently selected H, $R^1$, $C(O)R^1$, $C(O)OR^1$, $C(O)NHR^1$, $C(O)N(R^1)_2$, $SO_2NHR^1$ or $SO_2N(R^1)_2$;

$R^1$ is $R^2$, $R^3$, $R^4$ or $R^5$;

$R^2$ is phenyl which is unfused or fused with benzene or heteroarene;

$R^3$ is heteroaryl which is unfused or fused with benzene or heteroarene;

$R^4$ is cycloalkyl, cycloalkenyl, heterocycloalkyl or heterocycloalkenyl, each of which is unfused or fused with benzene or heteroarene;

$R^5$ is alkyl, alkenyl or alkynyl, each of which is unsubstituted or substituted with one or two or three of independently selected $R^6$, OH, (O), CN, $NH_2$, $NHR^6$, $N(R^6)_2$, F, Cl, Br or I;

$R^6$ is $R^7$, $R^8$ or $R^9$;

$R^7$ is phenyl which is unfused or fused with benzene or heteroarene;

$R^8$ is heteroaryl which is unfused or fused with benzene or heteroarene;

$R^9$ is cycloalkyl, cycloalkenyl, heterocycloalkyl or heterocycloalkenyl, each of which is unfused or fused with benzene or heteroarene;

C¹ is H;

D¹ is $R^{18}$, $R^{19}$ or $R^{20}$;

$R^{18}$ is pyrimidinyl which is unfused or fused with benzene or heteroarene and unsubstituted or substituted with one or two or three of independently selected CN, NO₂, F, Cl, Br or I;

$R^{19}$ is pyridinyl which is unfused or fused with benzene or heteroarene;

$R^{20}$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyrimidinyl, pyrrolyl, 1,2,4-thiadiazolyl, thiazolyl, thiophenyl, triazinyl or 1,2,3-triazolyl, each of which is unfused or fused with benzene or heteroaryl and substituted with $NHR^{21}$ or $N(CH_3)R^{21}$;

$R^{21}$ is $R^{22}$, $R^{23}$, $R^{24}$ or $R^{25}$;

$R^{22}$ is phenyl which is unfused or fused with benzene, heteroarene or $R^{22A}$; $R^{22A}$ is cycloalkane, cycloalkene, heterocycloalkane or heterocycloalkene;

$R^{23}$ is heteroaryl which is unfused or fused with benzene or heteroarene;

$R^{24}$ is cycloalkyl, cycloalkenyl, heterocycloalkyl or heterocycloalkenyl, each of which is unfused or fused with benzene or heteroarene;

$R^{25}$ is alkyl, alkenyl or alkynyl, each of which is unsubstituted or substituted with one or two or three of independently selected $R^{26}$;

$R^{26}$ is $R^{27}$, $R^{28}$ or $R^{29}$;

$R^{27}$ is phenyl which is unfused or fused with benzene or heteroarene;

$R^{28}$ is heteroaryl which is unfused or fused with benzene or heteroarene;

$R^{29}$ is cycloalkyl, cycloalkenyl, heterocycloalkyl or heterocycloalkenyl, each of which is unfused or fused with benzene or heteroarene;

each foregoing cyclic moiety is independently unsubstituted, further unsubstituted, substituted or further substituted with one or two or three or four or five of independently selected $R^{30}$, $OR^{30}$, $C(O)R^{30}$, $NH_2$, $NHR^{30}$, $N(R^{30})_2$, $C(O)NH_2$, $C(O)NHR^{30}$, $C(O)N(R^{30})_2$, $SO_2NH_2$, $SO_2NHR^{30}$, $NHSO_2R^{30}$, $N(R^{30})SO_2R^{30}$, $SO_2N(R^{30})_2$, $CF_3$, $CF_2CF_3$, $C(O)H$, CN, $C(O)OH$, (O), OH, $NO_2$, $CF_3$, $CF_2CF_3$, $OCF_3$, $OCF_2CF_3$, F, Cl, Br or I;

$R^{30}$ is $R^{31}$, $R^{32}$, $R^{33}$ or $R^{34}$;

$R^{31}$ is phenyl which is unfused or fused with benzene, heteroarene or $R^{31A}$; $R^{31A}$ is cycloalkane, cycloalkene, heterocycloalkane or heterocycloalkene;

$R^{32}$ is heteroaryl which is unfused or fused with benzene, heteroarene or $R^{32A}$; $R^{32A}$ is cycloalkane, cycloalkene, heterocycloalkane or heterocycloalkene;

$R^{33}$ is cycloalkyl, cycloalkenyl, heterocycloalkyl or heterocloalkenyl, each of which is unfused or fused with benzene, heteroarene or $R^{33A}$; $R^{33A}$ is cycloalkane, cycloalkene, heterocycloalkane or heterocycloalkene;

$R^{34}$ is alkyl, alkenyl or alkynyl, each of which is unsubstituted or substituted with one or two or three of independently selected $R^{35}$, $OR^{35}$, $SR^{35}$, $C(O)OR^{35}$, $NH_2$, $NHR^{35}$, OH, $N(R^{35})_2$, $C(O)NH_2$, $C(O)NHR^{35}$, $C(O)N(R^{35})_2$, $NHC(O)R^{35}$, $N(R^{35})C(O)R^{35}$, F, Cl, Br or I;

$R^{35}$ is $R^{36}$, $R^{37}$, $R^{38}$ or $R^{39}$;

$R^{36}$ is phenyl which is unfused or fused with benzene, heteroarene or $R^{36A}$; $R^{36A}$ is cycloalkane, cycloalkene, heterocycloalkane or heterocycloalkene;

$R^{37}$ is heteroaryl which is unfused or fused with benzene, heteroarene or $R^{37A}$; $R^{37A}$ is cycloalkane, cycloalkene, heterocycloalkane or heterocycloalkene;

$R^{38}$ is cycloalkyl, cycloalkenyl, heterocycloalkyl or heterocloalkenyl, each of which is unfused or fused with benzene, heteroarene or $R^{38A}$; $R^{38A}$ is cycloalkane, cycloalkene, heterocycloalkane or heterocycloalkene;

the moieties represented by $R^{31-33}$ and $R^{36-38}$ are independently unsubstituted or substituted with one, two, three four or five of independently substituted $R^{39}$, $OR^{39}$, $C(O)OR^{39}$, $NH_2$, $NHR^{39}$, $N(R^{39})_2$, $C(O)NH_2$, $C(O)NHR^{39}$, $C(O)N(R^{39})_2$, $NHC(O)R^{39}$, $N(R^{39})C(O)R^{39}$, $SO_2NH_2$, $SO_2NHR^{39}$, $SO_2N(R^{39})_2$, (O), CN, F, Cl, Br or I; and $R^{39}$ is alkyl, alkenyl or alkynyl, each of which is unsubstituted or substituted with phenyl, furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyrimidinyl, pyrrolyl, 1,2,4-thiadiazolyl, thiazolyl, thiophenyl, triazinyl or 1,2,3-triazolyl.

Still another embodiment comprises compounds having formula (I), and therapeutically acceptable salts, prodrugs and salts of prodrugs thereof, wherein $X^1$ is $X^2$, $SX^2$ or $N(A^1)(B^1)$;

$X^2$ is $X^5$ or $X^6$;

$X^5$ is cycloalkyl, cycloalkenyl, heterocycloalkyl or heterocycloalkenyl;

$X^6$ is alkyl, alkenyl or alkynyl, each of which is unsubstituted or substituted with phenyl, furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyrimidinyl, pyrrolyl, 1,2,4-thiadiazolyl, thiazolyl, thiophenyl, triazinyl or 1,2,3-triazolyl;

$A^1$ and $B^1$ are independently selected $R^1$;

$R^1$ is $R^2$, $R^3$, $R^4$ or $R^5$;

$R^2$ is phenyl which is unfused or fused with benzene;

$R^3$ is heteroaryl which is unfused or fused with benzene;

$R^4$ is cycloalkyl, cycloalkenyl, heterocycloalkyl or heterocycloalkenyl, each of which is unfused or fused with benzene;

$R^5$ is alkyl, alkenyl or alkynyl, each of which is unsubstituted or substituted with one or two or three of independently selected $R^6$, OH, (O), CN, $NH_2$, $NHR^6$, $N(R^6)_2$, F, Cl, Br or I;

$R^6$ is $R^7$, $R^8$ or $R^9$;

$R^7$ is phenyl which is unfused or fused with benzene;

$R^8$ is heteroaryl which is unfused or fused with benzene;

$R^9$ is cycloalkyl, cycloalkenyl, heterocycloalkyl or heterocycloalkenyl, each of which is unfused or fused with benzene;

$C^1$ is H;

$D^1$ is $R^{18}$, $R^{19}$ or $R^{20}$;

$R^{18}$ is pyrimidinyl which is unfused or fused with benzene and unsubstituted or substituted with one or two or three of independently selected CN, NO₂, F, Cl, Br or I;

$R^{19}$ is pyridinyl which is unfused or fused with benzene;

$R^{20}$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyrimidinyl, pyrrolyl, 1,2,4-thiadiazolyl, thiazolyl, thiophenyl, triazinyl or 1,2,3-triazolyl, each of which is unfused or fused with benzene or heteroaryl and substituted with $NHR^{21}$ or $N(CH_3)R^{21}$;

$R^{21}$ is $R^{22}$, $R^{23}$, $R^{24}$ or $R^{25}$;

$R^{22}$ is phenyl which is unfused or fused with benzene, heteroarene or $R^{22A}$; $R^{22A}$ is cycloalkane, cycloalkene, heterocycloalkane or heterocycloalkene;

$R^{23}$ is heteroaryl which is unfused or fused with benzene;

$R^{24}$ is cycloalkyl, cycloalkenyl, heterocycloalkyl or heterocycloalkenyl, each of which is unfused or fused with benzene;

$R^{25}$ is alkyl, alkenyl or alkynyl, each of which is unsubstituted or substituted with one or two or three of independently selected $R^{26}$;

$R^{26}$ is $R^{27}$, $R^{28}$ or $R^{29}$;

$R^{27}$ is phenyl which is unfused or fused with benzene;

$R^{28}$ is heteroaryl which is unfused or fused with benzene;

$R^{29}$ is cycloalkyl, cycloalkenyl, heterocycloalkyl or heterocycloalkenyl, each of which is unfused or fused with benzene;

each foregoing cyclic moiety is independently unsubstituted, further unsubstituted, substituted or further substituted with one or two or three or four or five of independently selected $R^{30}$, $OR^{30}$, $C(O)R^{30}$, $NH_2$, $N(R^3)_2$, $C(O)NHR^{30}$, $C(O)N(R^{30})_2$, $SO_2NH_2$, $NHSO_2R^{30}$, CN, C(O)OH, (O), OH, $NO_2$, $CF_3$, $OCF_3$, F, Cl, Br or I;

$R^{30}$ is $R^{31}$, $R^{32}$, $R^{33}$ or $R^{34}$;

$R^{31}$ is phenyl which is unfused or fused with benzene;

$R^{32}$ is heteroaryl which is unfused or fused with benzene;

$R^{33}$ is cycloalkyl, cycloalkenyl, heterocycloalkyl or heterocloalkenyl, each of which is unfused or fused with benzene;

$R^{34}$ is alkyl, alkenyl or alkynyl, each of which is unsubstituted or substituted with one or two or three of independently selected $R^{35}$, $OR^{35}$, $SR^{35}$, OH, $N(R^{35})_2$;

$R^{35}$ is $R^{36}$, $R^{37}$, $R^{38}$ or $R^{39}$;

$R^{36}$ is phenyl which is unfused or fused with benzene;

$R^{37}$ is heteroaryl which is unfused or fused with benzene;

$R^{38}$ is cycloalkyl, cycloalkenyl, heterocycloalkyl or heterocloalkenyl, each of which is unfused or fused with benzene;

the moieties represented by $R^{31-33}$ and $R^{36-38}$ are independently unsubstituted or substituted with one, two, three four or five of independently substituted $R^{39}$, $OR^{39}$, $N(R^{39})_2$, $SO_2NH_2$, (O), CN, F, Cl, Br or I; and $R^{39}$ is alkyl, alkenyl or alkynyl, each of which is unsubstituted or substituted with phenyl, furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyrimidinyl, pyrrolyl, 1,2,4-thiadiazolyl, thiazolyl, thiophenyl, triazinyl or 1,2,3-triazolyl.

Still another embodiment comprises compositions comprising an excipient and a therapeutically effective amount of a compound having formula (I).

Still another embodiment comprises methods of treating diseases involving overexpression or unregulation of a protein kinase in a mammal, the methods comprising administering thereto a therapeutically effective amount of a compound having formula (I).

Still another embodiment comprises methods of treating colorectal cancer, endometrial carcinoma, epithelial ovarian cancer, esophageal carcinoma, hepatoblastoma, malignant lymphoma, melanoma, non-Hodgkin's lymphoma, non-small cell lung cancer, oropharyngeal carcinoma, ovarian carcinoma or squamous cell carcinoma in a mammal, the methods comprising administering thereto a therapeutically effective amount of a compound having formula (I).

Still another embodiment comprises compositions comprising an excipient and a therapeutically effective amount of a compound having formula (I) and a therapeutically effective amount of one or more than one additional therapeutic agent.

Still another embodiment comprises methods of treating diseases involving overexpression or unregulation of a protein kinase in a mammal, the methods comprising administering thereto a therapeutically effective amount of a compound having formula (I) and a therapeutically effective amount of one or more than one additional therapeutic agent.

Still another embodiment comprises methods of treating colorectal cancer, endometrial carcinoma, epithelial ovarian cancer, esophageal carcinoma, hepatoblastoma, malignant lymphoma, melanoma, non-Hodgkin's lymphoma, non-small cell lung cancer, oropharyngeal carcinoma, ovarian carcinoma or squamous cell carcinoma in a mammal, the methods comprising administering thereto a therapeutically effective amount of a compound having formula (I) and a therapeutically effective amount of one or more than one additional therapeutic agent.

Still another embodiment comprises compounds having formula (I) which are (R)-3-(2-(3,4,5-trimethoxyphenylamino)pyrimidin-4-ylamino)-4-(1,2,2-trimethylpropylamino)cyclobut-3-ene-1,2-dione, (R,R)-3-(2-(1-phenylethylamino)pyrimidin-4-ylamino)-4-(1,2,2-trimethylpropylamino)cyclobut-3-ene-1,2-dione, (R)-3-(2-(4-bromophenylamino)pyrimidin-4-ylamino)-4-(1,2,2-trimethylpropylamino)cyclobut-3-ene-1,2-dione, (R)-3-(2-(benzo[1,3]dioxol-5-ylamino)pyrimidin-4-ylamino)-4-(1,2,2-trimethylpropylamino)cyclobut-3-ene-1,2-dione, (R)-3-(2-(4-trifluoromethoxyphenylamino)pyrimidin-4-ylamino)-4-(1,2,2-trimethylpropylamino)cyclobut-3-ene-1,2-dione, (R)-3-(2-(3-methylphenylamino)pyrimidin-4-ylamino)-4-(1,2,2-trimethylpropylamino)cyclobut-3-ene-1,2-dione, (R)-3-(2-(4-fluorophenylamino)pyrimidin-4-ylamino)-4-(1,2,2-trimethylpropylamino)cyclobut-3-ene-1,2-dione, (R)-3-(2-(2-isopropylphenylamino)pyrimidin-4-ylamino)-4-(1,2,2-trimethylpropylamino)cyclobut-3-ene-1,2-dione, (R)-3-(2-(4-chlorophenylamino)pyrimidin-4-ylamino)-4-(1,2,2-trimethylpropylamino)cyclobut-3-ene-1,2-dione, (R)-3-(2-phenylaminopyrimidin-4-ylamino)-4-(1,2,2-trimethylpropylamino)cyclobut-3-ene-1,2-dione, (R)-3-(2-(naphthalen-2-ylamino)pyrimidin-4-ylamino)-4-(1,2,2-trimethylpropylamino)cyclobut-3-ene-1,2-dione, (R)-3-(2-(3-bromo-4-methylphenylamino)pyrimidin-4-ylamino)-4-(1,2,2-trimethylpropylamino)cyclobut-3-ene-1,2-dione, (R)-3-(2-(biphenyl-4-ylamino)pyrimidin-4-ylamino)-4-(1,2,2-trimethylpropylamino)cyclobut-3-ene-1,2-dione, (R)-3-(2-(4-phenoxyphenylamino)pyrimidin-4-ylamino)-4-(1,2,2-trimethylpropylamino)cyclobut-3-ene-1,2-dione, (R)-3-(2-(3-phenoxyphenylamino)pyrimidin-4-ylamino)-4-(1,2,2-trimethylpropylamino)cyclobut-3-ene-1,2-dione, (R)-3-(2-(2,3-dimethoxyphenylamino)pyrimidin-4-ylamino)-4-(1,2,2-trimethylpropylamino)cyclobut-3-ene-1,2-dione, R)-3-(2-(2,3-dihydrobenzo[1,4]dioxin-6-ylamino)pyrimidin-4-ylamino)-4-(1,2,2-trimethylpropylamino)cyclobut-3-ene-1,2-dione, (R)-3-(2-(naphthalen-1-ylamino)pyrimidin-4-ylamino)-4-(1,2,2-trimethylpropylamino)cyclobut-3-ene-1,2-dione, R)-3-(2-(2,4-dimethoxyphenylamino)pyrimidin-4-ylamino)-4-(1,2,2-trimethylpropylamino)cyclobut-3-ene-1,2-dione, (R)-3-(2-(2,5-dimethoxyphenylamino)pyrimidin-4-ylamino)-4-(1,2,2-trimethylpropylamino)cyclobut-3-ene-1,2-dione, (R)-3-(2-(biphenyl-3-ylamino)pyrimidin-4-ylamino)-4-(1,2,2-trimethylpropylamino)cyclobut-3-ene-1,2-dione, (R)-3-(2-(4-methoxyphenylamino)pyrimidin-4-ylamino)-4-(1,2,2-trimethylpropylamino)cyclobut-3-ene-1,2-dione, (R)-3-(2-(3-chlorophenylamino)pyrimidin-4-ylamino)-4-(1,2,2-trimethylpropylamino)cyclobut-3-ene-1,2-dione, (R)-3-(2-(3-bromophenylamino)pyrimidin-4-ylamino)-4-(1,2,2-trimethylpropylamino)cyclobut-3-ene-1,2-dione, (R)-3-(2-(3-isopropoxyphenylamino)pyrimidin-4-ylamino)-4-(1,2,2-trimethylpropylamino)cyclobut-3-ene-1,2-dione, (R)-3-(2-(4-morpholin-4-ylphenylamino)pyrimidin-4-ylamino)-4-(1,2,2-trimethylpropylamino)cyclobut-3-ene-1,2-dione, (R)-3-(4-(3,4-dioxo-2-(1,2,2-trimethylpropylamino)cyclobut-1-enylamino)pyrimidin-2-ylamino)benzonitrile, (R)-3-(2-(3,4-difluorophenylamino)pyrimidin-4-ylamino)-4-(1,2,2-trimethylpropylamino)cyclobut-3-ene-1,2-dione, (R)-3-(2-(3-chloro-4-fluorophenylamino)pyrimidin-4-ylamino)-4-(1,2,2-trimethylpropylamino)cyclobut-3-ene-1,2-dione,
(R)-3-(2-(3-trifluoromethylphenylamino)pyrimidin-4-ylamino)-4-(1,2,2-trimethylpropylamino)cyclobut-3-ene-1,2-dione,
(R)-3-(2-(9H-fluoren-2-ylamino)pyrimidin-4-ylamino)-4-(1,2,2-trimethylpropylamino)cyclobut-3-ene-1,2-dione,
(R)-4'-(4-(3,4-dioxo-2-(1,2,2-trimethylpropylamino)cyclobut-1-enylamino)pyrimidin-2-ylamino)biphenyl-4-carbonitrile,
(R)-3-(2-(2'-methoxybiphenyl-4-ylamino)pyrimidin-4-ylamino)-4-(1,2,2-trimethylpropylamino)cyclobut-3-ene-1,2-dione,
(R)-3-(2-(4-imidazol-1-ylphenylamino)pyrimidin-4-ylamino)-4-(1,2,2-trimethylpropylamino)cyclobut-3-ene-1,2-dione,
(R)-3-(2-(4'-methoxybiphenyl-4-ylamino)pyrimidin-4-ylamino)-4-(1,2,2-trimethylpropylamino)cyclobut-3-ene-1,2-dione,
(R)-3-(2-(4-dimethylaminophenylamino)pyrimidin-4-ylamino)-4-(1,2,2-trimethylpropylamino)cyclobut-3-ene-1,2-dione,
(R)-3-(2-((4-methoxyphenyl)methylamino)pyrimidin-4-ylamino)-4-(1,2,2-trimethylpropylamino)cyclobut-3-ene-1,2-dione,
(R)-3-(2-(4'-chlorobiphenyl-4-ylamino)pyrimidin-4-ylamino)-4-(1,2,2-trimethylpropylamino)cyclobut-3-ene-1,2-dione,
(R)-3-(2-(4-[1,2,3]thiadiazol-4-ylphenylamino)pyrimidin-4-ylamino)-4-(1,2,2-trimethylpropylamino)cyclobut-3-ene-1,2-dione,
(R)-3-(2-(4-thiophen-2-ylphenylamino)pyrimidin-4-ylamino)-4-(1,2,2-trimethylpropylamino)cyclobut-3-ene-1,2-dione,
(R)-3-(2-(benzothiazol-6-ylamino)pyrimidin-4-ylamino)-4-(1,2,2-trimethylpropylamino)cyclobut-3-ene-1,2-dione,
3-tert-butylamino-4-(2-(9H-fluoren-2-ylamino)pyrimidin-4-ylamino)cyclobut-3-ene-1,2-dione,
3-tert-butylamino-4-(2-(4-fluoro-3-methylphenylamino)pyrimidin-4-ylamino)cyclobut-3-ene-1,2-dione,
3-(2-(benzothiazol-6-ylamino)pyrimidin-4-ylamino)-4-tert-butylaminocyclobut-3-ene-1,2-dione,
3-tert-butylamino-4-(2-(4-[1,2,3]thiadiazol-4-ylphenylamino)pyrimidin-4-ylamino)cyclobut-3-ene-1,2-dione,
3-tert-butylamino-4-(2-(4-(4-methylpiperazin-1-yl)phenylamino)pyrimidin-4-ylamino)cyclobut-3-ene-1,2-dione,
3-tert-butylamino-4-(2-(4-hydroxy-3-methylphenylamino)pyrimidin-4-ylamino)cyclobut-3-ene-1,2-dione,
3-tert-butylamino-4-(2-(indan-5-ylamino)pyrimidin-4-ylamino)cyclobut-3-ene-1,2-dione,
3-tert-butylamino-4-(2-(4-morpholin-4-ylphenylamino)pyrimidin-4-ylamino)cyclobut-3-ene-1,2-dione,
3-tert-butylamino-4-(2-(4-morpholin-4-ylmethylphenylamino)pyrimidin-4-ylamino)cyclobut-3-ene-1,2-dione,
3-tert-butylamino-4-(2-(naphthalen-2-ylamino)pyrimidin-4-ylamino)cyclobut-3-ene-1,2-dione,
3-(2-(benzo[b]thiophen-5-ylamino)pyrimidin-4-ylamino)-4-tert-butylaminocyclobut-3-ene-1,2-dione,
3-tert-butylamino-4-(2-(2,3-dihydrobenzofuran-5-ylamino)pyrimidin-4-ylamino)cyclobut-3-ene-1,2-dione,
3-(2-(benzofuran-5-ylamino)pyrimidin-4-ylamino)-4-tert-butylaminocyclobut-3-ene-1,2-dione,
3-tert-butylamino-4-(2-(1H-indol-5-ylamino)pyrimidin-4-ylamino)cyclobut-3-ene-1,2-dione,
3-tert-butylamino-4-(2-(1H-indazol-5-ylamino)pyrimidin-4-ylamino)cyclobut-3-ene-1,2-dione,
3-tert-butylamino-4-(2-(1-methyl-1H-indazol-5-ylamino)pyrimidin-4-ylamino)cyclobut-3-ene-1,2-dione,
3-tert-butylamino-4-(2-(4-pyrrol-1-ylphenylamino)pyrimidin-4-ylamino)cyclobut-3-ene-1,2-dione,
3-tert-butylamino-4-(2-(4-pyrazol-1-ylphenylamino)pyrimidin-4-ylamino)cyclobut-3-ene-1,2-dione,
3-tert-butylamino-4-(2-(4-(4,6-dimethoxypyrimidin-2-yl)phenylamino)pyrimidin-4-ylamino)cyclobut-3-ene-1,2-dione,
3-(2-(1-acetyl-2,3-dihydro-1H-indol-5-ylamino)pyrimidin-4-ylamino)-4-tert-butylaminocyclobut-3-ene-1,2-dione,
3-tert-butylamino-4-(2-(2,3-dihydro-1H-indol-5-ylamino)pyrimidin-4-ylamino)cyclobut-3-ene-1,2-dione,
3-tert-butylamino-4-(2-(9H-carbazol-2-ylamino)pyrimidin-4-ylamino)cyclobut-3-ene-1,2-dione,
3-tert-butylamino-4-(2-(9-ethyl-9H-carbazol-2-ylamino)pyrimidin-4-ylamino)cyclobut-3-ene-1,2-dione,
3-(2-(benzothiazol-5-ylamino)pyrimidin-4-ylamino)-4-tert-butylaminocyclobut-3-ene-1,2-dione,
(R)-3-(2-(4-phenylthiazol-2-ylamino)pyrimidin-4-ylamino)-4-(1,2,2-trimethylpropylamino)cyclobut-3-ene-1,2-dione,
3-tert-butylamino-4-(2-(4-phenylthiazol-2-ylamino)pyrimidin-4-ylamino)cyclobut-3-ene-1,2-dione,
3-(2-(biphenyl-4-ylamino)pyrimidin-4-ylamino)-4-tert-butylaminocyclobut-3-ene-1,2-dione,
3-(2-(biphenyl-4-ylamino)pyrimidin-4-ylamino)-4-(4-trifluoromethoxyphenylamino)cyclobut-3-ene-1,2-dione,
11391) 3-(2-(biphenyl-4-ylamino)pyrimidin-4-ylamino)-4-(2,2-dimethylpropylamino)cyclobut-3-ene-1,2-dione,
3-(2-(biphenyl-4-ylamino)pyrimidin-4-ylamino)-4-(cyclopropylmethylamino)cyclobut-3-ene-1,2-dione,
3-(2-(biphenyl-4-ylamino)pyrimidin-4-ylamino)-4-(2-morpholin-4-ylethylamino)cyclobut-3-ene-1,2-dione,
3-(2-(biphenyl-4-ylamino)pyrimidin-4-ylamino)-4-(1,3-dimethylbutylamino)cyclobut-3-ene-1,2-dione,
3-(2-(biphenyl-4-ylamino)pyrimidin-4-ylamino)-4-(1,2-dimethylpropylamino)cyclobut-3-ene-1,2-dione,
3-(2-(biphenyl-4-ylamino)pyrimidin-4-ylamino)-4-(1-phenylethylamino)cyclobut-3-ene-1,2-dione,
(S)-3-(2-(biphenyl-4-ylamino)pyrimidin-4-ylamino)-4-(1,2,2-trimethylpropylamino)cyclobut-3-ene-1,2-dione,
3-(2-(biphenyl-4-ylamino)pyrimidin-4-ylamino)-4-(1,1-dimethylpropylamino)cyclobut-3-ene-1,2-dione,
(R)-3-(4-(3,4,5-trimethoxyphenylamino)-(1,3,5)triazin-2-ylamino)-4-(1,2,2-trimethylpropylamino)cyclobut-3-ene-1,2-dione,
4-(3,4-dioxo-2-(1-phenylethylamino)cyclobut-1-enylamino)-2-(3,4,5-trimethoxyphenylamino)pyrimidine-5-carbonitrile,
(S)-4-(3,4-dioxo-2-(1,2,2-timethylpropylamino)cyclobut-1-enylamino)-2-(3,4,5-trimethoxyphenylamino)pyrimidine-5-carbonitrile,
4-(2-(1,2-dimethylpropylamino)-3,4-dioxocyclobut-1-enylamino)-2-(3,4,5-trimethoxyphenylamino)pyrimidine-5-carbonitrile,
3-tert-butylamino-4-(2-(9H-fluoren-2-ylamino)-5-fluoropyrimidin-4-ylamino)cyclobut-3-ene-1,2-dione,
(R)-3-(3-(biphenyl-4-ylamino)-[1,2,4]thiadiazol-5-ylamino)-4-(1,2,2-trimethylpropylamino)cyclobut-3-ene-1,2-dione,
(S)-3-(3-(biphenyl-4-ylamino)-[1,2,4]thiadiazol-5-ylamino)-4-(1,2,2-trimethylpropylamino)cyclobut-3-ene-1,2-dione,
3-tert-butylamino-4-(2-(4-iodophenylamino)pyrimidin-4-ylamino)cyclobut-3-ene-1,2-dione, 3-tert-butylamino-4-(2-(4-pyridin-4-ylphenylamino)pyrimidin-4-ylamino)cyclobut-3-ene-1,2-dione,
3-tert-butylamino-4-(2-(4-pyridin-3-ylphenylamino)pyrimidin-4-ylamino)cyclobut-3-ene-1,2-dione,
3-tert-butylamino-4-(2-(4-(1H-pyrazol-4-yl)phenylamino)pyrimidin-4-ylamino)cyclobut-3-ene-1,2-dione,
3-tert-butylamino-4-(2-(4-pyrimidin-5-ylphenylamino)pyrimidin-4-ylamino)cyclobut-3-ene-1,2-dione,
3-tert-butylamino-4-(2-(4-(2,4-dimethoxypyrimidin-5-yl)phenylamino)pyrimidin-4-ylamino)cyclobut-3-ene-1,2-dione,
3-tert-butylamino-4-(2-(4-(2-methoxy-pyrimidin-5-yl)phenylamino)pyrimidin-4-ylamino)cyclobut-3-ene-1,2-dione,
3-tert-butylamino-4-(2-chloro-5-fluoropyrimidin-4-ylamino)cyclobut-3-ene-1,2-dione,
3-tert-butylamino-4-(5-fluoro-2-(4-[1,2,3]thiadiazol-4-ylphenylamino)pyrimidin-4-ylamino)cyclobut-3-ene-1,2-dione,
3-tert-butylamino-4-(2-chloropyrimidin-4-ylamino)cyclobut-3-ene-1,2-dione,
3-tert-butylamino-4-(2-(4-(1,2,4-triazol)-1-ylphenylamino)pyrimidin-4-ylamino)cyclobut-3-ene-1,2-dione,
3-tert-butylamino-4-(2-cyclohexylaminopyrimidin-4-ylamino)cyclobut-3-ene-1,2-dione,
3-tert-butylamino-4-(2-(4-(2H-pyrazol-3-yl)phenylamino)pyrimidin-4-ylamino)cycyclobut-3-ene-1,2-dione,
3-(2-(1H-benzotriazol-5-ylamino)pyrimidin-4-ylamino)-4-tert-butylaminocyclobut-3-ene-1,2-dione,
3-tert-butylamino-4-(2-(4-thiophen-3-ylphenylamino)pyrimidin-4-ylamino)cyclobut-3-ene-1,2-dione,
3-(2-(1H-benzoimidazol-5-ylamino)pyrimidin-4-ylamino)-4-tert-butylaminocyclobut-3-ene-1,2-dione,
3-(2-(1-acetyl-2,3-dihydro-1H-indol-6-ylamino)pyrimidin-4-ylamino)-4-tert-butylaminocyclobut-3-ene-1,2-dione,
N-(3-(4-(2-tert-butylamino-3,4-dioxocyclobut-1-enylamino)pyrimidin-2-ylamino)phenyl)methanesulfonamide,
3-tert-butylamino-4-(2-(2-trifluoromethyl-1H-benzoimidazol-5-ylamino)pyrimidin-4-ylamino)cyclobut-3-ene-1,2-dione,
N-(4-(4-(2-tert-butylamino-3,4-dioxocyclobut-1-enylamino)pyrimidin-2-ylamino)phenyl)-4-methylbenzenesulfonamide,
3-tert-butylamino-4-(2-(2-methylbenzothiazol-5-ylamino)pyrimidin-4-ylamino)cyclobut-3-ene-1,2-dione,
3-tert-butylamino-4-(2-(4-(morpholine-4-sulfonyl)phenylamino)pyrimidin-4-ylamino)cyclobut-3-ene-1,2-dione,
3-tert-butylamino-4-(2-(3-(morpholine-4-sulfonyl)phenylamino)pyrimidin-4-ylamino)cyclobut-3-ene-1,2-dione,
3-tert-butylamino-4-(2-(2-methyl-3H-benzoimidazol-5-ylamino)pyrimidin-4-ylamino)cyclobut-3-ene-1,2-dione,
3-tert-butylamino-4-(2-(1-(toluene-4-sulfonyl)-1H-indol-5-ylamino)pyrimidin-4-ylamino)cyclobut-3-ene-1,2-dione,
3-tert-butylamino-4-(2-(1-methanesulfonyl-2,3-dihydro-1H-indol-5-ylamino)pyrimidin-4-ylamino)cyclobut-3-ene-1,2-dione,
3-tert-butylamino-4-(2-(4-pyridin-2-ylphenylamino)pyrimidin-4-ylamino)cyclobut-3-ene-1,2-dione,
3-tert-butylamino-4-(2-(4-(4-methanesulfonylpiperazin-1-yl)phenylamino)pyrimidin-4-ylamino)cyclobut-3-ene-1,2-dione,
3-tert-butylamino-4-(2-(3-oxo-3,4-dihydro-2H-benzo[1,4]oxazin-7-ylamino)pyrimidin-4-ylamino)cyclobut-3-ene-1,2-dione,
3-tert-butylamino-4-(2-(3-pyrrol-1-ylphenylamino)pyrimidin-4-ylamino)cyclobut-3-ene-1,2-dione,
3-tert-butylamino-4-(2-(2-methylbenzothiazol-6-ylamino)pyrimidin-4-ylamino)cyclobut-3-ene-1,2-dione,
3-tert-butylamino-4-(2-(4-oxazol-5-ylphenylamino)pyrimidin-4-ylamino)cyclobut-3-ene-1,2-dione,
3-tert-butylamino-4-(2-(pyridin-4-ylamino)pyrimidin-4-ylamino)cyclobut-3-ene-1,2-dione,
3-tert-butylamino-4-(2-(4-dimethylaminomethylphenylamino)pyrimidin-4-ylamino)cyclobut-3-ene-1,2-dione,
5-(4-(2-tert-butylamino-3,4-dioxocyclobut-1-enylamino)pyrimidin-2-ylamino)-2-methylisoindole-1,3-dione,
3-tert-butylamino-4-(6-chloropyrimidin-4-ylamino)cyclobut-3-ene-1,2-dione,
3-tert-butylamino-4-(6-(4-iodophenylamino)pyrimidin-4-ylamino)cyclobut-3-ene-1,2-dione,
3-cyclopropylamino-4-(2-(4-iodophenylamino)pyrimidin-4-ylamino)cyclobut-3-ene-1,2-dione,
3-cyclobutylamino-4-(2-(4-iodophenylamino)pyrimidin-4-ylamino)cyclobut-3-ene-1,2-dione,
3-cyclobutylamino-4-(2-(4-pyridin-4-ylphenylamino)pyrimidin-4-ylamino)cyclobut-3-ene-1,2-dione,
4'-(4-(2-tert-butylamino-3,4-dioxocyclobut-1-enylamino)pyrimidin-2-ylamino)biphenyl-4-carboxylic acid dimethylamide,
3-tert-butylamino-4-(2-(6-methyl-2-(4-thiophen-3-ylphenylamino)pyrimidin-4-ylamino)cyclobut-3-ene-1,2-dione,
3-(4-(2-tert-butylamino-3,4-dioxocyclobut-1-enylamino)pyrimidin-2-ylamino)benzenesulfonamide,
3-tert-butylamino-4-(2-(3-methoxyphenylamino)pyrimidin-4-ylamino)cyclobut-3-ene-1,2-dione,
3-(2-(4-(4-benzylpiperazin-1-yl)phenylamino)pyrimidin-4-ylamino)-4-tert-butylaminocyclobut-3-ene-1,2-dione,
3-tert-butylamino-4-(2-(4-nitrophenylamino)pyrimidin-4-ylamino)cyclobut-3-ene-1,2-dione,
3-tert-butylamino-4-(2-(6-chloro-5-methylpyridin-3-ylamino)pyrimidin-4-ylamino)cyclobut-3-ene-1,2-dione,
4-(4-(2-tert-butylamino-3,4-dioxocyclobut-1-enylamino)pyrimidin-2-ylamino)-3-methoxy-N-piperidin-4-ylbenzamide,
3-tert-butylamino-4-(pyrimidin-4-ylamino)cyclobut-3-ene-1,2-dione,
S-3-(2-chloropyrimidin-4-ylamino)-4-(1-cyclohexylethylamino)cyclobut-3-ene-1,2-dione,
R-3-(2-chloropyrimidin-4-ylamino)-4-(1-cyclohexylethylamino)cyclobut-3-ene-1,2-dione,
S-3-(1-cyclohexylethylamino)-4-(2-(4-thiophen-3-ylphenylamino)pyrimidin-4-ylamino)cyclobut-3-ene-1,2-dione,
(R)-3-(1-cyclohexylethylamino)-4-(2-(4-thiophen-3-ylphenylamino)pyrimidin-4-ylamino)cyclobut-3-ene-1,2-dione,
(S)-3-(1-cyclohexylethylamino)-4-(2-(4-(4,6-dimethoxypyrimidin-2-yl)phenylamino)pyrimidin-4-ylamino)cyclobut-3-ene-1,2-dione,
(R)-3-(1-cyclohexylethylamino)-4-(2-(4-(4,6-dimethoxypyrimidin-2-yl)phenylamino)pyrimidin-4-ylamino)cyclobut-3-ene-1,2-dione,
(S)-3-(1-cyclohexylethylamino)-4-(2-(4-pyridin-4-ylphenylamino)pyrimidin-4-ylamino)cyclobut-3-ene-1,2-dione,
(R)-3-(1-cyclohexylethylamino)-4-(2-(4-pyridin-4-ylphenylamino)pyrimidin-4-ylamino)cyclobut-3-ene-1,2-dione,
3-tert-butylamino-4-(2-(3,4,5,6-tetrahydro-2H-[1,4']bipyridinyl-4-ylamino)pyrimidin-4-ylamino)cyclobut-3-ene-1,2-dione,
3-tert-butylamino-4-(2-(4-(1-methylpiperidin-4-yl)phenylamino)pyrimidin-4-ylamino)cyclobut-3-ene-1,2-dione,
3-(piperidin-4-ylamino)-4-(2-(4-pyridin-4-ylphenylamino)pyrimidin-4-ylamino)cyclobut-3-ene-1,2-dione, 3-(4-(2-tert-butylamino-3,4-dioxocyclobut-1-enylamino)pyrimidin-2-ylamino)-N-(1-methylpiperidin-4-yl)benzamide,
3-(4-(2-tert-butylamino-3,4-dioxocyclobut-1-enylamino)pyrimidin-2-ylamino)benzoic acid,
3-(4-(2-tert-butylamino-3,4-dioxo-cyclobut-1-enylamino)pyrimidin-2-ylamino)-N-cycloheptylbenzamide,
3-(4-(2-tert-butylamino-3,4-dioxo-cyclobut-1-enylamino)pyrimidin-2-ylamino)-N-cyclohexylbenzamide,
3-(4-(2-tert-butylamino-3,4-dioxo-cyclobut-1-enylamino)pyrimidin-2-ylamino)-N-cyclopentylbenzamide,
3-(4-(2-tert-butylamino-3,4-dioxo-cyclobut-1-enylamino)pyrimidin-2-ylamino)-N-cyclobutylbenzamide,
3-(4-(2-tert-butylamino-3,4-dioxo-cyclobut-1-enylamino)pyrimidin-2-ylamino)-N-cyclohexyl-4-methoxybenzamide,
3-(4-(2-tert-butylamino-3,4-dioxo-cyclobut-1-enylamino)pyrimidin-2-ylamino)-4-methoxybenzoic acid,
3-tert-butylamino-4-(2-(quinolin-6-ylamino)pyrimidin-4-ylamino)cyclobut-3-ene-1,2-dione,
(R)-3-(2-(4-fluoro-3-methylphenylamino)pyrimidin-4-ylamino)-4-(1,2,2-trimethylpropylamino)cyclobut-3-ene-1,2-dione,
3-tert-butylamino-4-(5-fluoro-2-(2'-methoxybiphenyl-4-ylamino)pyrimidin-4-ylamino)cyclobut-3-ene-1,2-dione,
N-cyclobutyl-4-((4-((2-((2-hydroxy-1,1-dimethylethyl)amino)-3,4-dioxocyclobut-1-en-1-yl)amino)pyrimidin-2-yl)amino)-3-methoxybenzamide,
N-cyclobutyl-3-methoxy-4-((4-((2-((1-methyl-1-phenylethyl)amino)-3,4-dioxocyclobut-1-en-1-yl)amino)pyrimidin-2-yl)amino)benzamide,
N-cyclobutyl-4-((4-((2-((1,1-dimethylprop-2-ynyl)amino)-3,4-dioxocyclobut-1-en-1-yl)amino)pyrimidin-2-yl)amino)-3-methoxybenzamide,
4-((4-((2-((1-cyano-1-methylethyl)amino)-3,4-dioxocyclobut-1-en-1-yl)amino)pyrimidin-2-yl)amino)-N-cyclobutyl-3-methoxybenzamide,
N-cyclobutyl-4-((4-((2-((1-cyclopropyl-1-methylethyl)amino)-3,4-dioxocyclobut-1-en-1-yl)amino)pyrimidin-2-yl)amino)-3-methoxybenzamide,
N-cyclobutyl-4-((4-((2-((1,1-dimethyl-2-morpholin-4-ylethyl)amino)-3,4-dioxocyclobut-1-en-1-yl)amino)pyrimidin-2-yl)amino)-3-methoxybenzamide,
N-cyclobutyl-3-methoxy-4-((4-((2-morpholin-4-yl-3,4-dioxocyclobut-1-en-1-yl)amino)pyrimidin-2-yl)amino)benzamide,
N-cyclobutyl-4-((4-((2-((1,1-dimethyl-3-oxobutyl)amino)-3,4-dioxocyclobut-1-en-1-yl)amino)pyrimidin-2-yl)amino)-3-methoxybenzamide,
N-cyclobutyl-4-((4-((3,4-dioxo-2-(propylamino)cyclobut-1-en-1-yl)amino)pyrimidin-2-yl)amino)-3-methoxybenzamide,
4-((4-((2-anilino-3,4-dioxocyclobut-1-en-1-yl)amino)pyrimidin-2-yl)amino)-N-cyclobutyl-3-methoxybenzamide,
N-cyclobutyl-4-((4-((3,4-dioxo-2-(propylthio)cyclobut-1-en-1-yl)amino)pyrimidin-2-yl)amino)-3-methoxybenzamide,
3-((2-(1,1'-biphenyl-4-ylamino)pyridin-4-yl)amino)-4-(tert-butylamino)cyclobut-3-ene-1,2-dione,
3-(tert-butylamino)-4-((2-((4-pyridin-4-ylphenyl)amino)pyridin-4-yl)amino)cyclobut-3-ene-1,2-dione,
4-((4-((2-(tert-butylamino)-3,4-dioxocyclobut-1-en-1-yl)amino)pyridin-2-yl)amino)-N-cyclohexyl-3-methoxybenzamide,
N-cyclopentyl-4-((4-((2-(diethylamino)-3,4-dioxocyclobut-1-en-1-yl)amino)pyrimidin-2-yl)amino)-3-methoxybenzamide,
N-cyclopentyl-3-methoxy-4-((4-((2-neopentyl-3,4-dioxocyclobut-1-en-1-yl)amino)pyrimidin-2-yl)amino)benzamide,
N-cyclopentyl-4-((4-((2-(1-ethylpropyl)-3,4-dioxocyclobut-1-en-1-yl)amino)pyrimidin-2-yl)amino)-3-methoxybenzamide,
N-cyclopentyl-3-methoxy-4-((4-((2-(2-methylprop-1-enyl)-3,4-dioxocyclobut-1-en-1-yl)amino)pyrimidin-2-yl)amino)benzamide,
2-(4-((4-((2-(tert-butylamino)-3,4-dioxocyclobut-1-en-1-yl)amino)pyrimidin-2-yl)amino)phenyl)-N-(1-methylpiperidin-4-yl)acetamide,
2-(4-((4-((2-(tert-butylamino)-3,4-dioxocyclobut-1-en-1-yl)amino)pyrimidin-2-yl)amino)phenyl)-N-(pyridin-3-ylmethyl)acetamide,
2-(3-((4-((2-(tert-butylamino)-3,4-dioxocyclobut-1-en-1-yl)amino)pyrimidin-2-yl)amino)phenyl)-N-(1-methylpiperidin-4-yl)acetamide,
2-(3-((4-((2-(tert-butylamino)-3,4-dioxocyclobut-1-en-1-yl)amino)pyrimidin-2-yl)amino)phenyl)-N-cyclobutylacetamide,
3-(tert-butylamino)-4-((2-((4-(pyridin-2-ylethynyl)phenyl)amino)pyrimidin-4-yl)amino)cyclobut-3-ene-1,2-dione,
3-(tert-butylamino)-4-((2-((4-pent-1-ynylphenyl)amino)pyrimidin-4-yl)amino)cyclobut-3-ene-1,2-dione,
3-(tert-butylamino)-4-((2-((4-(3-(diethylamino)prop-1-ynyl)phenyl)amino)pyrimidin-4-yl)amino)cyclobut-3-ene-1,2-dione,
3-(tert-butylamino)-4-((2-((4-((1E)-4-hydroxybut-1-enyl)phenyl)amino)pyrimidin-4-yl)amino)cyclobut-3-ene-1,2-dione,
3-(tert-butylamino)-4-((2-((4-((E)-2-pyridin-2-ylvinyl)phenyl)amino)pyrimidin-4-yl)amino)cyclobut-3-ene-1,2-dione,
3-(tert-butylamino)-4-((2-((4-((1E)-pent-1-enyl)phenyl)amino)pyrimidin-4-yl)amino)cyclobut-3-ene-1,2-dione,
N-(4-((4-((2-(tert-butylamino)-3,4-dioxocyclobut-1-en-1-yl)amino)pyrimidin-2-yl)amino)-3-methoxyphenyl)cyclopentanecarboxamide,
3-((2-((4-amino-2-methoxyphenyl)amino)pyrimidin-4-yl)amino)-4-(tert-butylamino)cyclobut-3-ene-1,2-dione,
6-((4-((2-(tert-butylamino)-3,4-dioxocyclobut-1-en-1-yl)amino)pyrimidin-2-yl)amino)-N-cyclopentylnicotinamide,
4-((4-((2-(tert-butylamino)-3,4-dioxocyclobut-1-en-1-yl)amino)pyrimidin-2-yl)amino)-N-cyclopentyl-3-fluorobenzamide,
4-((4-((2-(tert-butylamino)-3,4-dioxocyclobut-1-en-1-yl)amino)pyrimidin-2-yl)amino)benzoic acid,
4-((4-((2-(tert-butylamino)-3,4-dioxocyclobut-1-en-1-yl)amino)pyrimidin-2-yl)amino)-N-((1R)-1-(hydroxymethyl)-3-methylbutyl)benzamide,
N-2-(4-((4-((2-(tert-butylamino)-3,4-dioxocyclobut-1-en-1-yl)amino)pyrimidin-2-yl)amino)benzoyl)-L-leucinamide,
4-((4-((2-(tert-butylamino)-3,4-dioxocyclobut-1-en-1-yl)amino)pyrimidin-2-yl)amino)-N-((1S)-2-hydroxy-1-phenylethyl)benzamide,
4-((4-((2-(tert-butylamino)-3,4-dioxocyclobut-1-en-1-yl)amino)pyrimidin-2-yl)amino)-N-(3-ethoxypropyl)benzamide,
4-((4-((2-(tert-butylamino)-3,4-dioxocyclobut-1-en-1-yl)amino)pyrimidin-2-yl)amino)-N-(3-(methylthio)propyl)benzamide,
4-((4-((2-(tert-butylamino)-3,4-dioxocyclobut-1-en-1-yl)amino)pyrimidin-2-yl)amino)-N-(4-(dimethylamino)butyl)benzamide, 4-((4-((2-(tert-butylamino)-3,4-dioxocyclobut-1-en-1-yl)
  amino)pyrimidin-2-yl)amino)-N-(2-phenoxyethyl)benza-
  mide,
4-((4-((2-(tert-butylamino)-3,4-dioxocyclobut-1-en-1-yl)
  amino)pyrimidin-2-yl)amino)-N-(3-(2-oxopyrrolidin-1-
  yl)propyl)benzamide,
4-((4-((2-(tert-butylamino)-3,4-dioxocyclobut-1-en-1-yl)
  amino)pyrimidin-2-yl)amino)-N-(2-(5-methoxy-1H-in-
  dol-3-yl)ethyl)benzamide,
4-((4-((2-(tert-butylamino)-3,4-dioxocyclobut-1-en-1-yl)
  amino)pyrimidin-2-yl)amino)-N-(3,4-difluorobenzyl)
  benzamide,
4-((4-((2-(tert-butylamino)-3,4-dioxocyclobut-1-en-1-yl)
  amino)pyrimidin-2-yl)amino)-N-((1S)-1-(1-naphthyl)
  ethyl)benzamide,
N-(2-(4-(aminosulfonyl)phenyl)ethyl)-4-((4-((2-(tert-buty-
  lamino)-3,4-dioxocyclobut-1-en-1-yl)amino)pyrimidin-
  2-yl)amino)benzamide,
4-((4-((2-(tert-butylamino)-3,4-dioxocyclobut-1-en-1-yl)
  amino)pyrimidin-2-yl)amino)-N-(pyridin-2-ylmethyl)
  benzamide,
4-((4-((2-(tert-butylamino)-3,4-dioxocyclobut-1-en-1-yl)
  amino)pyrimidin-2-yl)amino)-N-(2-(1H-imidazol-4-yl)
  ethyl)benzamide,
4-((4-((2-(tert-butylamino)-3,4-dioxocyclobut-1-en-1-yl)
  amino)pyrimidin-2-yl)amino)-N-(2-morpholin-4-ylethyl)
  benzamide,
4-((4-((2-(tert-butylamino)-3,4-dioxocyclobut-1-en-1-yl)
  amino)pyrimidin-2-yl)amino)-3-methoxybenzoic acid,
4-((4-((2-(tert-butylamino)-3,4-dioxocyclobut-1-en-1-yl)
  amino)pyrimidin-2-yl)amino)-N-(4-(dimethylamino)cy-
  clohexyl)-3-methoxybenzamide,
4-((4-((2-(tert-butylamino)-3,4-dioxocyclobut-1-en-1-yl)
  amino)pyrimidin-2-yl)amino)-N-(1,1-dimethyl-2-mor-
  pholin-4-ylethyl)-3-methoxybenzamide,
4-((4-((2-(tert-butylamino)-3,4-dioxocyclobut-1-en-1-yl)
  amino)pyrimidin-2-yl)amino)-N-(1-ethylpiperidin-3-yl)-
  3-methoxybenzamide,
4-((4-((2-(tert-butylamino)-3,4-dioxocyclobut-1-en-1-yl)
  amino)pyrimidin-2-yl)amino)-N-cyclobutyl-3-(trifluo-
  romethoxy)benzamide and
4-((6-((2-(tert-butylamino)-3,4-dioxocyclobut-1-en-1-yl)
  amino)-9H-purin-2-yl)amino)-N-cyclobutyl-3-methoxy-
  benzamide.

BRIEF DESCRIPTION OF THE SEVERAL
VIEWS OF THE DRAWING(S)

Not Applicable.

DETAILED DESCRIPTION OF THE INVENTION

Variable moieties of compounds herein are represented by identifiers (capital letters with numerical and/or alphabetical superscripts) and may be specifically embodied.

It is meant to be understood that proper valences are maintained for all moieties and combinations thereof, that monovalent moieties having more than one atom are attached through their left ends.

It is also meant to be understood that a specific embodiment of a variable moiety may be the same or different as another specific embodiment having the same identifier.

The term "cyclic moiety," as used herein, means benzene, cycloalkane, cycloalkyl, cycloalkene, cycloalkenyl, heteroarene, heteroaryl, heterocycloalkane, heterocycloalkyl, heterocycloalkene, heterocycloalkenyl, phenyl, spiroalkyl, spiroalkenyl, spiroheteroalkyl and spiroheteroalkenyl.

The term "cycloalkane," as used herein, means $C_3$-cycloalkane, $C_4$-cycloalkane, $C_5$-cycloalkane and $C_6$-cycloalkane.

The term "cycloalkyl," as used herein, means $C_3$-cycloalkyl, $C_4$-cycloalkyl, $C_5$-cycloalkyl, $C_6$-cycloalkyl, $C_7$-cycloalkyl and $C_8$-cycloalkyl.

The term "cycloalkene," as used herein, means $C_4$-cycloalkene, $C_5$-cycloalkene, $C_6$-cycloalkene, $C_7$-cycloalkene, and $C_8$-cycloalkene.

The term "cycloalkenyl," as used herein, means $C_4$-cycloalkenyl, $C_5$-cycloalkenyl, $C_6$-cycloalkenyl, $C_7$-cycloalkenyl, and $C_8$-cycloalkenyl.

The term "heteroarene," as used herein, means furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine and 1,2,3-triazole.

The term "heteroaryl," as used herein, means furanyl, imidazolyl, isothiazolyl, isoxazolyl, 1,2,4-oxadiazoyl, 1,3,4-oxadiazolyl, oxazolyl, pyrazinyl, pyrazolyl, pyridazinyl, pyridinyl, pyrimidinyl, pyrrolyl, tetrazolyl, 1,3,4-thiadiazolyl, thiazolyl, thiophenyl, 1,3,5-triazinyl and 1,2,3-triazolyl.

The term "heterocycloalkane," as used herein, means cycloalkane having one or two or three $CH_2$ moieties replaced with independently selected O, S, S(O), $SO_2$ or NH and one or two CH moieties unreplaced or replaced with N and also means cycloalkane having one or two or three $CH_2$ moieties unreplaced or replaced with independently selected O, S, S(O), $SO_2$ or NH and one or two CH moieties replaced with N. The term "heterocycloalkane," as used herein, also means the saturated part of indoline.

The term "heterocycloalkyl," as used herein, means cycloalkyl having one or two or three $CH_2$ moieties replaced with independently selected O, S, S(O), $SO_2$ or NH and one or two CH moieties unreplaced or replaced with N and also means cycloalkyl having one or two or three $CH_2$ moieties unreplaced or replaced with independently selected O, S, S(O), $SO_2$ or NH and one or two CH moieties replaced with N.

The term "heterocycloalkene," as used herein, means cycloalkene having one or two or three $CH_2$ moieties replaced with independently selected O, S, S(O), $SO_2$ or NH and one or two CH moieties unreplaced or replaced with N and also means cycloalkene having one or two or three $CH_2$ moieties unreplaced or replaced with independently selected O, S, S(O), $SO_2$ or NH and one or two CH moieties replaced with N.

The term "heterocycloalkenyl," as used herein, means cycloalkenyl having one or two or three $CH_2$ moieties replaced with independently selected O, S, S(O), $SO_2$ or NH and one or two CH moieties unreplaced or replaced with N and also means cycloalkenyl having one or two or three $CH_2$ moieties unreplaced or replaced with independently selected O, S, S(O), $SO_2$ or NH and one or two CH moieties replaced with N.

The term "alkenyl," as used herein, means $C_2$-alkenyl, $C_3$-alkenyl, $C_4$-alkenyl, $C_5$-alkenyl and $C_6$-alkenyl.

The term "alkyl," as used herein, means $C_1$-alkyl, $C_2$-alkyl, $C_3$-alkyl, $C_4$-alkyl, $C_5$-alkyl and $C_6$-alkyl.

The term "alkynyl," as used herein, means $C_2$-alkynyl, $C_3$-alkynyl, $C_4$-alkynyl, $C_5$-alkynyl and $C_6$-alkynyl.

The term "$C_2$-alkenyl," as used herein, means ethenyl (vinyl).

The term "$C_3$-alkenyl," as used herein, means 1-propen-1-yl, 1-propen-2-yl (isopropenyl) and 1-propen-3-yl (allyl).

The term "$C_4$-alkenyl," as used herein, means 1-buten-1-yl, 1-buten-2-yl, 1,3-butadien-1-yl, 1,3-butadien-2-yl, 2-buten-1-yl, 2-buten-2-yl, 3-buten-1-yl, 3-buten-2-yl, 2-methyl-1-propen-1-yl and 2-methyl-2-propen-1-yl.

The term "$C_5$-alkenyl," as used herein, means 2-methylene-3-buten-1-yl, 2-methylenebut-1-yl, 2-methyl-1-buten-1-yl, 2-methyl-1,3-butadien-1-yl, 2-methyl-2-buten-1-yl, 2-methyl-3-buten-1-yl, 2-methyl-3-buten-2-yl, 3-methyl-1-buten-1-yl, 3-methyl-1-buten-2-yl, 3-methyl-1,3-butadien-1-yl, 3-methyl-1,3-butadien-2-yl, 3-methyl-2-buten-1-yl, 3-methyl-2-buten-2-yl, 3-methyl-3-buten-1-yl, 3-methyl-3-buten-2-yl, 1-penten-1-yl, 1-penten-2-yl, 1-penten-3-yl, 1,3-pentadien-1-yl, 1,3-penta-dien-2-yl, 1,3-pentadien-3-yl, 1,4-pentadien-1-yl, 1,4-pentadien-2-yl, 1,4-pentadien-3-yl, 2-penten-1-yl, 2-penten-2-yl, 2-penten-3-yl, 2,4-pentadien-1-yl, 2,4-pentadien-2-yl, 3-penten-1-yl, 3-penten-2-yl, 4-penten-1-yl and 4-penten-2-yl.

The term "$C_6$-alkenyl," as used herein, means 2,2-dimethyl-3-buten-1-yl, 2,3-dimethyl-1-buten-1-yl, 2,3-dimethyl-1,3-butadien-1-yl, 2,3-dimethyl-2-buten-1-yl, 2,3-dimethyl-3-buten-1-yl, 2,3-dimethyl-3-buten-2-yl, 3,3-dimethyl-1-buten-1-yl, 3,3-dimethyl-1-buten-2-yl, 2-ethenyl-1,3-butadien-1-yl, 2-ethenyl-2-buten-1-yl, 2-ethyl-1-buten-1-yl, 2-ethyl-1,3-butadien-1-yl, 2-ethyl-2-buten-1-yl, 2-ethyl-3-buten-1-yl, 1-hexen-1-yl, 1-hexen-2-yl, 1-hexen-3-yl, 1,3-hexadien-1-yl, 1,3-hexadien-2-yl, 1,3-hexadien-3-yl, 1,3,5-hexatrien-1-yl, 1,3,5-hexatrien-2-yl, 1,3,5-hexatrien-3-yl, 1,4-hexadien-1-yl, 1,4-hexadien-2-yl, 1,4-hexadien-3-yl, 1,5-hexadien-1-yl, 1,5-hexadien-2-yl, 1,5-hexadien-3-yl, 2-hexen-1-yl, 2-hexen-2-yl, 2-hexen-3-yl, 2,4-hexadien-1-yl, 2,4-hexadien-2-yl, 2,4-hexadien-3-yl, 2,5-hexadien-1-yl, 2,5-hexadien-2-yl, 2,5-hexadien-3-yl, 3-hexen-1-yl, 3-hexen-2-yl, 3-hexen-3-yl, 3,5-hexadien-1-yl, 3,5-hexadien-2-yl, 3,5-hexadien-3-yl, 4-hexen-1-yl, 4-hexen-2-yl, 4-hexen-3-yl, 5-hexen-1-yl, 5-hexen-2-yl, 5-hexen-3-yl, 2-methylene-3-methyl-3-buten-1-yl, 2-methylene-3-methylbut-1-yl, 2-methylene-3-penten-1-yl, 2-methylene-4-penten-1-yl, 2-methylenepent-1-yl, 2-methylenepent-3-yl, 3-methylene-1-penten-1-yl, 3-methylene-1-penten-2-yl, 3-methylenepent-1-yl, 3-methylene-1,4-pentadien-1-yl, 3-methylene-1,4-pentadien-2-yl, 3-methylene-pent-2-yl, 2-methyl-1-penten-1-yl, 2-methyl-1-penten-3-yl, 2-methyl-1,3-pentadien-1-yl, 2-methyl-1,3-pentadien-3-yl, 2-methyl-1,4-pentadien-1-yl, 2-methyl-1,4-pentadien-3-yl, 2-methyl-2-penten-1-yl, 2-methyl-2-penten-3-yl, 2-methyl-2,4-pentadien-1-yl, 2-methyl-2,4-pentadien-3-yl, 2-methyl-3-penten-1-yl, 2-methyl-3-penten-2-yl, 2-methyl-3-penten-3-yl, 2-methyl-4-penten-1-yl, 2-methyl-4-penten-2-yl, 2-methyl-4-penten-3-yl, 3-methyl-1-penten-1-yl, 3-methyl-1-penten-2-yl, 3-methyl-1,3-pentadien-1-yl, 3-methyl-1,3-pentadien-2-yl, 3-methyl-1,4-pentadien-1-yl, 3-methyl-1,4-pentadien-2-yl, 3-methyl-2-penten-1-yl, 3-methyl-2-penten-2-yl, 3-methyl-2,4-pentadien-1-yl, 3-methyl-3-penten-1-yl, 3-methyl-3-penten-2-yl, 3-methyl-4-penten-1-yl, 3-methyl-4-penten-2-yl, 3-methyl-4-penten-3-yl, 4-methyl-1-penten-1-yl, 4-methyl-1-penten-2-yl, 4-methyl-1-penten-3-yl, 4-methyl-1,3-pentadien-1-yl, 4-methyl-1,3-pentadien-2-yl, 4-methyl-1,3-pentadien-3-yl, 4-methyl-1,4-pentadien-1-yl, 4-methyl-1,4-pentadien-2-yl, 4-methyl-1,4-pentadien-3-yl, 4-methylene-2-penten-3-yl, 4-methyl-2-penten-1-yl, 4-methyl-2-penten-2-yl, 4-methyl-2-penten-3-yl, 4-methyl-2,4-pentadien-1-yl, 4-methyl-2,4-pentadien-2-yl, 4-methyl-3-penten-1-yl, 4-methyl-3-penten-2-yl, 4-methyl-3-penten-3-yl, 4-methyl-4-penten-1-yl and 4-methyl-4-penten-2-yl.

The term "$C_1$-alkyl," as used herein, means methyl.

The term "$C_2$-alkyl," as used herein, means ethyl.

The term "$C_3$-alkyl," as used herein, means prop-1-yl and prop-2-yl (isopropyl).

The term "$C_4$-alkyl," as used herein, means but-1-yl, but-2-yl, 2-methylprop-1-yl and 2-methylprop-2-yl (tert-butyl).

The term "$C_5$-alkyl," as used herein, means 2,2-dimethylprop-1-yl (neo-pentyl), 2-methylbut-1-yl, 2-methylbut-2-yl, 3-methylbut-1-yl, 3-methylbut-2-yl, pent-1-yl, pent-2-yl and pent-3-yl.

The term "$C_6$-alkyl," as used herein, means 2,2-dimethylbut-1-yl, 2,3-dimethylbut-1-yl, 2,3-dimethylbut-2-yl, 3,3-dimethylbut-1-yl, 3,3-dimethylbut-2-yl, 2-ethylbut-1-yl, hex-1-yl, hex-2-yl, hex-3-yl, 2-methylpent-1-yl, 2-methylpent-2-yl, 2-methylpent-3-yl, 3-methylpent-1-yl, 3-methylpent-2-yl, 3-methylpent-3-yl, 4-methylpent-1-yl and 4-methylpent-2-yl.

The term "$C_2$-alkynyl," as used herein, means ethynyl (acetylenyl).

The term "$C_3$-alkynyl," as used herein, means 1-propyn-1-yl and 2-propyn-1-yl (propargyl).

The term "$C_4$-alkynyl," as used herein, means 1-butyn-1-yl, 1,3-butadiyn-1-yl, 2-butyn-1-yl, 3-butyn-1-yl and 3-butyn-2-yl.

The term "$C_5$-alkynyl," as used herein, means 2-methyl-3-butyn-1-yl, 2-methyl-3-butyn-2-yl, 3-methyl-1-butyn-1-yl, 1,3-pentadiyn-1-yl, 1,4-pentadiyn-1-yl, 1,4-pentadiyn-3-yl, 2,4-pentadiyn-1-yl, 1-pentyn-1-yl, 1-pentyn-3-yl, 2-pentyn-1-yl, 3-pentyn-1-yl, 3-pentyn-2-yl, 4-pentyn-1-yl and 4-pentyn-2-yl.

The term "$C_6$-alkynyl," as used herein, means 2,2-dimethyl-3-butyn-1-yl, 3,3-dimethyl-1-butyn-1-yl, 2-ethyl-3-butyn-1-yl, 2-ethynyl-3-butyn-1-yl, 1-hexyn-1-yl, 1-hexyn-3-yl, 1,3-hexadiyn-1-yl, 1,3,5-hexatriyn-1-yl, 1,4-hexadiyn-1-yl, 1,4-hexadiyn-3-yl, 1,5-hexadiyn-1-yl, 1,5-hexadiyn-3-yl, 2-hexyn-1-yl, 2,5-hexadiyn-1-yl, 3-hexyn-1-yl, 3-hexyn-2-yl, 3,5-hexadiyn-2-yl, 4-hexyn-1-yl, 4-hexyn-2-yl, 4-hexyn-3-yl, 5-hexyn-1-yl, 5-hexyn-2-yl, 5-hexyn-3-yl, 2-methyl-3-pentyn-1-yl, 2-methyl-3-pentyn-2-yl, 2-methyl-4-pentyn-1-yl, 2-methyl-4-pentyn-2-yl, 2-methyl-4-pentyn-3-yl, 3-methyl-1-pentyn-1-yl, 3-methyl-4-pentyn-1-yl, 3-methyl-4-pentyn-2-yl, 3-methyl-1,4-pentadiyn-1-yl, 3-methyl-1,4-pentadiyn-3-yl, 3-methyl-4-pentyn-1-yl, 3-methyl-4-pentyn-3-yl, 4-methyl-1-pentyn-1-yl and 4-methyl-2-pentyn-1-yl.

The term "$C_4$-cycloalkane," as used herein, means cyclobutane.

The term "$C_5$-cycloalkane," as used herein, means cyclopentane and the saturated part of fluorene.

The term "$C_6$-cycloalkane," as used herein, means cyclohexane.

The term "$C_4$-cycloalkene," as used herein, means cyclobutene and 1,3-cyclobutadiene.

The term "$C_5$-cycloalkene," as used herein, means cyclopentene and 1,3-cyclopentadiene.

The term "$C_6$-cycloalkene," as used herein, means cyclohexene, 1,3-cyclohexadiene and 1,4-cyclohexadiene.

The term "$C_7$-cycloalkene," as used herein, means cycloheptene and 1,3-cycloheptadiene.

The term "$C_8$-cycloalkene," as used herein, means cyclooctene, 1,3-cyclooctadiene, 1,4-cyclooctadiene, 1,5-cyclooctadiene, 1,3,5-cyclooctatriene and 1,3,6-cyclooctatriene.

The term "$C_7$-cycloalkane," as used herein, means cycloheptane.

The term "$C_8$-cycloalkane," as used herein, means cyclooctane.

The term "$C_3$-cycloalkenyl," as used herein, means cycloprop-1-en-1-yl and cycloprop-2-en-1-yl.

The term "$C_4$-cycloalkenyl," as used herein, means cyclobut-1-en-1-yl and cyclobut-2-en-1-yl.

The term "C$_5$-cycloalkenyl," as used herein, means cyclopent-1-en-1-yl, cyclopent-2-en-1-yl, cyclopent-3-en-1-yl and cyclopenta-1,3-dien-1-yl.

The term "C$_6$-cycloalkenyl," as used herein, means cyclohex-1-en-1-yl, cyclohex-2-en-1-yl, cyclohex-3-en-1-yl, cyclohexa-1,3-dien-1-yl, cyclohexa-1,4-dien-1-yl, cyclohexa-1,5-dien-1-yl, cyclohexa-2,4-dien-1-yl and cyclohexa-2,5-dien-1-yl.

The term "C$_7$-cycloalkenyl," as used herein, means bicyclo[2.2.1]hept-2-en-1-yl, bicyclo[2.2.1]hept-2-en-2-yl, bicyclo[2.2.1]hept-2-en-5-yl, bicyclo[2.2.1]hept-2-en-7-yl, bicyclo[2.2.1]hepta-2,5-dien-1-yl, bicyclo[2.2.1]hepta-2,5-dien-2-yl, bicyclo[2.2.1]hepta-2,5-dien-7-yl, cyclohept-1-en-1-yl, cyclohept-2-en-1-yl, cyclohept-3-en-1-yl, cyclohept-4-en-1-yl, cyclohepta-1,3-dien-1-yl, cyclohepta-1,4-dien-1-yl, cyclohepta-1,5-dien-1-yl, cyclohepta-1,6-dien-1-yl, cyclohepta-2,4-dien-1-yl, cyclohepta-2,5-dien-1-yl, cyclohepta-2,6-dien-1-yl, cyclohepta-3,5-dien-1-yl, cyclohepta-1,3,5-trien-1-yl, cyclohepta-1,3,6-trien-1-yl, cyclohepta-1,4,6-trien-1-yl and cyclohepta-2,4,6-trien-1-yl.

The term "C$_8$-cycloalkenyl," as used herein, means bicyclo[2.2.2]oct-2-en-1-yl, bicyclo[2.2.2]oct-2-en-2-yl, bicyclo[2.2.2]oct-2-en-5-yl, bicyclo[2.2.2]oct-2-en-7-yl, bicyclo[2.2.2]octa-2,5-dien-1-yl, bicyclo[2.2.2]octa-2,5-dien-2-yl, bicyclo[2.2.2]octa-2,5-dien-7-yl, bicyclo[2.2.2]octa-2,5,7-trien-1-yl, bicyclo[2.2.2]octa-2,5,7-trien-2-yl cyclooct-1-en-1-yl, cyclooct-2-en-1-yl, cyclooct-3-en-1-yl, cyclooct-4-en-1-yl, cycloocta-1,3-dien-1-yl, cycloocta-1,4-dien-1-yl, cycloocta-1,5-dien-1-yl, cycloocta-1,6-dien-1-yl, cycloocta1,7-dien-1-yl, cycloocta-2,4-dien-1-yl, cycloocta-2,5-dien-1-yl, cycloocta-2,6-dien-1-yl, cycloocta-2,7-dien-1-yl, cycloocta-3,5-dien-1-yl, cycloocta-3,6-dien-1-yl, cycloocta-1,3,5-trien-1-yl, cycloocta-1,3,6-trien-1-yl, cycloocta-1,3,7-trien-1-yl, cycloocta-1,4,6-trien-1-yl, cycloocta-1,4,7-trien-1-yl, cycloocta-1,5,7-trien-1-yl, cycloocta-2,4,6-trien-1-yl, cycloocta-2,4,7-trien-1-yl, cycloocta-2,5,7-trien-1-yl and cycloocta-1,3,5,7-tetraen-1-yl.

The term "C$_3$-cycloalkyl," as used herein, means cycloprop-1-yl.

The term "C$_4$-cycloalkyl," as used herein, means cyclobut-1-yl.

The term "C$_5$-cycloalkyl," as used herein, means cyclopent-1-yl.

The term "C$_6$-cycloalkyl," as used herein, means cyclohex-1-yl.

Compounds of this invention may contain asymmetrically substituted carbon atoms in the R or S configuration, wherein the terms "R" and "S" are as defined in Pure Appl. Chem. (1976) 45, 13-10. Compounds having asymmetrically substituted carbon atoms with equal amounts of R and S configurations are racemic at those atoms. Atoms having excess of one configuration over the other are assigned the configuration in excess, preferably an excess of about 85%-90%, more preferably an excess of about 95%-99%, and still more preferably an excess greater than about 99%. Accordingly, this invention is meant to embrace racemic mixtures and relative and absolute diastereoisomers of the compounds thereof.

Compounds of this invention may also contain carbon-carbon double bonds or carbon-nitrogen double bonds in the Z or E configuration, in which the term "Z" represents the larger two substituents on the same side of a carbon-carbon or carbon-nitrogen double bond and the term "E" represents the larger two substituents on opposite sides of a carbon-carbon or carbon-nitrogen double bond. The compounds of this invention may also exist as a mixture of "Z" and "E" isomers.

Compounds of this invention may also exist as tautomers or equilibrium mixtures thereof wherein a proton of a compound shifts from one atom to another. Examples of tautomers include, but are not limited to, keto-enol, phenol-keto, oxime-nitroso, nitro-aci, imine-enamine and the like.

Compounds of this invention containing NH, C(O)OH, OH or SH moieties may have attached thereto prodrug-forming moieties. The prodrug-forming moieties are removed by metabolic processes and release the compounds having the freed NH, C(O)OH, OH or SH in vivo. Prodrugs are useful for adjusting such pharmacokinetic properties of the compounds as solubility and/or hydrophobicity, absorption in the gastrointestinal tract, bioavailability, tissue penetration, and rate of clearance.

Metabolites of compounds having formula (I) produced by in vitro or in vivo metabolic processes, may also have utility for treating diseases associated with overexpression or unregulation of a kinase.

Certain precursor compounds which may be metabolized in vitro or in vivo to form compounds having formula (I) may also have utility for treating diseases associated with overexpression or unregulation of a kinase.

Compounds having formula (I) may also be radiolabeled with a radioactive isotope such as a radioactive isotope of carbon (i.e. $^{13}$C), hydrogen (i.e. $^3$H), nitrogen (i.e. $^{15}$N), phosphorus (i.e. $^{32}$P), sulfur (i.e. $^{35}$S) or iodide (i.e. $^{125}$I). Radioactive isotopes may be incorporated into the compounds having formula (II) by reacting the same and a radioactive derivitizing agent or by incorporating a radiolabeled intermediate into their syntheses. The radiolabeled compounds of formula (II) are useful for both prognostic and diagnostic applications as well as for in vivo and in vitro imaging.

Compounds having formula (I) may exist as acid addition salts, basic addition salts or zwitterions. Salts of compounds having formula (I) are prepared during their isolation or following their purification. Acid addition salts are those derived from the reaction of a compound having formula (I) with acid. Accordingly, salts including the acetate, adipate, alginate, bicarbonate, citrate, aspartate, benzoate, benzenesulfonate (besylate), bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate and undecanoate salts of the compounds having formula (I) are meant to be embraced by this invention. Basic addition salts of compounds are those derived from the reaction of the compounds having formula (I) with the bicarbonate, carbonate, hydroxide or phosphate of cations such as lithium, sodium, potassium, calcium and magnesium.

Compounds having formula (I) may be administered, for example, bucally, ophthalmically, orally, osmotically, parenterally (intramuscularly, intraperintoneally intrasternally, intravenously, subcutaneously), rectally, topically, transdermally, vaginally and intraarterially as well as by intraarticular injection, infusion, and placement in the body, such as, for example, the vasculature by means of, for example, a stent.

Therapeutically effective amounts of a compound having formula (I) depend on recipient of treatment, disease treated and severity thereof, composition comprising it, time of administration, route of administration, duration of treatment, potency, rate of clearance and whether or not another drug is co-administered. The amount of a compound having formula (I) used to make a composition to be administered daily to a mammal in a single dose or in divided doses is from about 0.03 to about 200 mg/kg body weight. Single dose compositions contain these amounts or a combination of sub-multiples thereof.

Compounds having formula (I) may be administered with or without an excipient. Excipients include, but are not limited to, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like.

Excipients for preparation of compositions comprising a compound having formula (I) to be administered orally include, but are not limited to, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, mixtures thereof and the like. Excipients for preparation of compositions comprising a compound having formula (I) to be administered ophthalmically or orally include, but are not limited to, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like. Excipients for preparation of compositions comprising a compound having formula (I) to be administered osmotically include, but are not limited to, chlorofluorohydrocarbons, ethanol, water, mixtures thereof and the like. Excipients for preparation of compositions comprising a compound having formula (I) to be administered parenterally include, but are not limited to, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like. Excipients for preparation of compositions comprising a compound having formula (I) to be administered rectally or vaginally include, but are not limited to, cocoa butter, polyethylene glycol, wax, mixtures thereof and the like.

This invention also comprises combination therapeutic methods of treating disease conditions involving polo-like kinases, such as cancer, in a patient comprising administering thereto a therapeutically effective amount of a pharmaceutical composition comprising a compound having formula (I) and a therapeutically effective amount of one or more than one additional therapeutic agents and/or ionizing radiation.

The combination therapeutic methods include administering compositions of a compound having formula (I) and one or more than one additional therapeutic agents or ionizing radiation to a patient using any desired dosing and/or scheduling regimen.

Compounds having formula (I) may be administered with one or more than one additional therapeutic agents, wherein the additional therapeutic agents include ionizing radiation or chemotherapeutic agents, wherein chemotherapeutic agents include, but are not limited to, carboplatin, cisplatin, cyclophosphamide, dacarbazine, dexamethasone, docetaxel, doxorubicin, etoposide, fludarabine, irinotecan, CHOP (C: Cytoxan® (cyclophosphamide); H: Adriamycin® (hydroxydoxorubicin); O: Vincristine (Oncovin®); P: prednisone), paclitaxel, rapamycin, Rituxin® (rituximab), vincristine and the like.

Compounds having formula (I) are also expected to be useful as chemotherapeutic agents in combination with therapeutic agents that include, but are not limited to, angiogenesis inhibitors, antiproliferative agents, kinase inhibitors, receptor tyrosine kinase inhibitors, aurora kinase inhibitors, other polo-like kinase inhibitors, bcr-abl kinase inhibitors, growth factor inhibitors, COX-2 inhibitors, non-steroidal anti-inflammatory drugs (NSAIDS), antimitotic agents, alkylating agents, antimetabolites, intercalating antibiotics, platinum containing agents, growth factor inhibitors, ionizing radiation, cell cycle inhibitors, enzymes, topoisomerase inhibitors, biologic response modifiers, immunologicals, antibodies, hormonal therapies, retinoids/deltoids plant alkaloids, proteasome inhibitors, HSP-90 inhibitors, histone deacetylase inhibitors (HDAC) inhibitors, purine analogs, pyrimidine analogs, MEK inhibitors, CDK inhibitors, ErbB2 receptor inhibitors, mTOR inhibitors as well as other antitumor agents.

Angiogenesis inhibitors include, but are not limited to, EGFR inhibitors, PDGFR inhibitors, VEGFR inhibitors, TIE2 inhibitors, IGF1R inhibitors, matrix metalloproteinase 2 (MMP-2) inhibitors, matrix metalloproteinase-9 (MMP-9) inhibitors, thrombospondin analogs and the like.

Examples of EGFR inhibitors include, but are not limited to, Iressa (gefitinib), Tarceva (erlotinib or OSI-774), Erbitux (cetuximab), EMD-7200, ABX-EGF, HR3, IgA antibodies, TP-38 (IVAX), EGFR fusion protein, EGF-vaccine, anti-EGFr immunoliposomes, Tykerb (lapatinib) and the like.

Examples of PDGFR inhibitors include, but are not limited to, CP-673,451, CP-868596 and the like.

Examples of VEGFR inhibitors include, but are not limited to, Avastin (bevacizumab), Sutent (sunitinib, SU11248), Nexavar (sorafenib, BAY43-9006), CP-547,632, axitinib (AG13736), Zactima (vandetanib, ZD-6474), AEE788, AZD-2171, VEGF trap, Vatalanib (PTK-787, ZK-222584), Macugen, IM862, Pazopanib (GW786034), ABT-869, angiozyme and the like.

Examples of thrombospondin analogs include, but are not limited to, TSP-1, ABT-510, ABT-567, ABT-898 and the like.

Examples of aurora kinase inhibitors include, but are not limited to, VX-680, AZD-1152, MLN-8054 and the like.

An example of another polo-like kinase inhibitor includes, but is not limited to BI-2536 and the like.

Examples of bcr-abl kinase inhibitors include, but are not limited to, Gleevec (imatinib), Dasatinib (BMS354825) and the like.

Examples of platinum containing agents includes, but are not limited to, cisplatin, Paraplatin (carboplatin), eptaplatin, lobaplatin, nedaplatin, Eloxatin (oxaliplatin), satraplatin and the like.

Examples of mTOR inhibitors includes, but are not limited to, CCI-779, rapamycin, temsirolimus, everolimus, RAD001, AP-23573 and the like.

Examples of HSP-90 inhibitors includes, but are not limited to, geldanamycin, radicicol, 17-AAG, KOS-953, 17-DMAG, CNF-101, CNF-1010,17-AAG-nab, NCS-683664, Mycograb, CNF-2024, PU3, PU24FC1, VER49009, IPI-504, SNX-2112, STA-9090 and the like.

Examples of histone deacetylase inhibitors (HDAC) includes, but are not limited to, Suberoylanilide hydroxamic acid (SAHA), MS-275, Valproic acid, TSA, LAQ-824, Trapoxin, Depsipeptide and the like.

Examples of MEK inhibitors include, but are not limited to, PD325901, ARRY-142886, ARRY-438162, PD98059 and the like.

Examples of CDK inhibitors include, but are not limited to, flavopyridol, MCS-5A, CVT-2584, seliciclib (CYC-202, R-roscovitine), ZK-304709, PHA-690509, BMI-1040, GPC-286199, BMS-387,032, PD0332991, AZD-5438 and the like.

Examples of useful COX-2 inhibitors include, but are not limited to, CELEBREX™ (celecoxib), parecoxib, deracoxib, ABT-963, MK-663 (etoricoxib), COX-189 Lumiracoxib), BMS347070, RS 57067, NS-398, Bextra (valdecoxib), paracoxib, Vioxx (rofecoxib), SD-8381, 4-Methyl-2-(3,4-dimethylphenyl)-1-(4-sulfamoyl-phenyl-1H-pyrrole, T-614, JTE-522, S-2474, SVT-2016, CT-3, SC-58125, Arcoxia (etoricoxib) and the like.

Examples of non-steroidal anti-inflammatory drugs (NSAIDs) include, but are not limited to, Salsalate (Amigesic), Diflunisal (Dolobid), Ibuprofen (Motrin), Ketoprofen (Orudis), Nabumetone (Relafen), Piroxicam (Feldene), Naproxen (Aleve, Naprosyn), Diclofenac (Voltaren), Indomethacin (Indocin), Sulindac (Clinoril), Tolmetin (Tolectin), Etodolac (Lodine), Ketorolac (Toradol), Oxaprozin (Daypro) and the like.

Examples of ErbB2 receptor inhibitors include, but are not limited to, CP-724-714, CI-1033 (canertinib), Herceptin (trastuzumab), Omitarg (2C4, petuzumab), TAK-165, GW-572016 (Ionafarnib), GW-282974, EKB-569, PI-166, dHER2 (HER2Vaccine), APC8024 (HER2 Vaccine), anti-HER/2neu bispecific antibody, B7.her2IgG3, AS HER2 trifunctional bispecfic antibodies, mAB AR-209, mAB 2B-1 and the like.

Examples of alkylating agents include, but are not limited to, nitrogen mustard N-oxide, cyclophosphamide, ifosfamide, trofosfamide, chlorambucil, melphalan, busulfan, mitobronitol, carboquone, thiotepa, ranimustine, nimustine, Cloretazine (VNP 40101M), temozolomide, AMD-473, altretamine, AP-5280, apaziquone, brostallicin, bendamustine, carmustine, estramustine, fotemustine, glufosfamide, KW-2170, mafosfamide, mitolactol, carmustine (BCNU), lomustine (CCNU), Busulfan, Treosulfan, Decarbazine, Temozolomide and the like.

Examples of antimetabolites include but are not limited to, methotrexate, 6-mercaptopurine riboside, mercaptopurine, 5-fluorouracil (5-FU) alone or in combination with leucovorin, tegafur, UFT, doxifluridine, carmofur, cytarabine, cytarabine ocfosfate, enocitabine, S-1, Alimta (premetrexed disodium, LY231514, MTA), Gemzar (gemcitabine, Eli Lilly), fludarabine, 5-azacitidine, capecitabine, cladribine, clofarabine, decitabine, eflornithine, ethnylcytidine, cytosine arabinoside, hydroxyurea, TS-1, melphalan, nelarabine, nolatrexed, ocfosate, disodium premetrexed, pentostatin, pelitrexol, raltitrexed, triapine, trimetrexate, vidarabine, mycophenolic acid, tiazofurin, Ribavirin, EICAR, hydroxyurea, deferoxamine and the like.

Examples of antibiotics include intercalating antibiotics but are not limited to, aclarubicin, actinomycin D, amrubicin, annamycin, adriamycin, bleomycin, daunorubicin, doxorubicin, elsamitrucin, epirbucin, glarbuicin, idarubicin, mitomycin C, nemorubicin, neocarzinostatin, peplomycin, pirarubicin, rebeccamycin, stimalamer, streptozocin, valrubicin, zinostatin, combinations thereof and the like.

Examples of topoisomerase inhibiting agents include, but are not limited to, one or more agents selected from the group consisting of aclarubicin, amonafide, belotecan, camptothecin, 10-hydroxycamptothecin, 9-aminocamptothecin, Amsacrine, Cardioxane (Dexrazoxine), diflomotecan, irinotecan HCL (Camptosar), edotecarin, epirubicin (Ellence), etoposide, exatecan, Becatecarin, gimatecan, lurtotecan, orathecin (Supergen), BN-80915, mitoxantrone, pirarbucin, pixantrone, rubitecan, sobuzoxane, SN-38, tafluposide, topotecan and the like.

Examples of antibodies include, but are not limited to, Rituximab, Cetuximab, Bevacizumab, Trastuzimab, specific CD40 antibodies and specific IGF1R antibodies, chTNT-1/B, Denosumab, Panorex (Edrecolomab), Rencarex (WX G250), Zanolimumab, Lintuzumab Ticilimumab and the like.

Examples of hormonal therapies include, but are not limited to, exemestane (Aromasin), leuprolide acetate, Buserelin, Cetrorelix, Deslorelin, Vantas, anastrozole (Arimidex), fosrelin (Zoladex), goserelin, Degarelix, doxercalciferol, fadrozole, formestane, tamoxifen citrate (tamoxifen), Arzoxifene, Casodex, Abarelix, Trelstar, finasteride, fulvestrant, toremifene, raloxifene, Trilostane (Modrastane, Desopan), lasofoxifene, letrozole, flutamide, bicalutamide, megesterol, mifepristone, nilutamide, dexamethasone, predisone, other glucocorticoids and the like.

Examples of retinoids/deltoids include, but are not limited to, seocalcitol (EB 1089, CB 1093), lexacalcitrol (KH 1060), fenretinide, Panretin (aliretinoin), Atragen, Bexarotene, LGD-1550 and the like.

Examples of plant alkaloids include, but are not limited to, vincristine, vinblastine, vindesine, vinorelbine and the like.

Examples of proteasome inhibitors include, but are not limited to, bortezomib (Velcade), MG132, NPI-0052, PR-171 and the like.

Examples of immunologicals include, but are not limited to, interferons and numerous other immune enhancing agents. Interferons include interferon alpha, interferon alpha-2a, interferon alpha-2b, interferon beta, interferon gamma-1a, interferon gamma-1b (Actimmune), or interferon gamma-n1 and combinations thereof. Other agents include Alfaferone (Leukocyte alpha interferon, Cliferon), filgrastim, lentinan, sizofilan, TheraCys, ubenimex, WF-10, aldesleukin, alemtuzumab, BAM-002, decarbazine, daclizumab, denileukin, gemtuzumab ozogamicin, ibritumomab, imiquimod, lenograstim, lentinan, melanoma vaccine (Corixa), molgramostim, OncoVAC-CL, sargaramostim, tasonermin, tecleukin, thymalasin, tositumomab, Virulizin, Z-100, epratuzumab, mitumomab, oregovomab, pemtumomab (Y-muHMFG1), Provenge (Dendreon), CTLA4 (cytotoxic lymphocyte antigen 4) antibodies, agents capable of blocking CTLA4 such as MDX-010 and the like.

Examples of biological response modifiers are agents that modify defense mechanisms of living organisms or biological responses, such as survival, growth, or differentiation of tissue cells to direct them to have anti-tumor activity. Such agents include krestin, lentinan, sizofuran, picibanil PF-3512676 (CpG-8954), ubenimex and the like.

Examples of pyrimidine analogs include, but are not limited to, 5-Fluorouracil, Floxuridine, Doxifluridine, Ratitrexed, cytarabine (ara C), Cytosine arabinoside, Fludarabine, triacetyluridine Troxacitabine (Troxatyl), Gemcitabine and the like.

Examples of purine analogs include but are not limited to, Mercaptopurine, thioguanine and the like.

Examples of antimitotic agents include, but are not limited to, N-(2-((4-hydroxyphenyl)amino)pyridin-3-yl)-4-methoxybenzenesulfonamide, paclitaxel, docetaxel, epothilone D (KOS-862), PNU100940 (109881), Batabulin, Ixabepilone (BMS 247550), Patupilone, XRP-9881, Vinflunine, ZK-EPO and the like.

Compounds of the present invention are also intended to be used as a radiosensitizer that enhances the efficacy of radiotherapy. Examples of radiotherapy include but are not limited to, external beam radiotherapy (XBRT), or teletherapy, brachtherapy or sealed source radiotherapy, unsealed source radiotherapy and the like.

Additionally, compounds having formula (I) may be combined with other antitumor agents selected from the following agents, Genasense, Panitumumab, Zevalin, Bexxar (Corixa), Arglabin, Abarelix, Alimta, EPO906, discodermolide, Neovastat, enzastaurin, Combrestatin A4P, ZD-6126, AVE-8062, DMXAA, Thymitaq, Temodar, Revlimid, Cypat, Histerelin, Plenaizis, Atrasentan, Celeuk (celmoleukin), Satraplatin, thalomide (Thalidomide), theratope, Temilifene, ABI-007, Evista, Atamestane, Xyotax, Targretin, Triazone, Aposyn, Nevastat, Ceplene, Lanreotide, Aredia (pamidronic acid), Orathecin, Virulizin, Gastrimmune, DX-8951f, Mepact (Liposome muramyl tripeptide phophatidylethanolamine, Junovan), Dimericine (Liposome T4 endonuclease V), Onconase, BEC2, Xcytrin, CeaVac, NewTrexin, OvaRex, Osidem, Advexin, RSR13 (efaproxiral, Cotara, NBI-3001 (IL-4), Canvaxin, GMK vaccine, PEG Interferon A, Taxoprexin, gene therapy agents such as TNFerade (GeneVac) or GVAX, Interferon-alpha, Interferon-gamma, Gardasil, Eniluracil (GW 776C85), Lonafarnib, ABT-100, Tumor necrosis factor, Lovastatin, staurosporine, dactinomycin, zorubicin, Bosentan, OncoVAX, Cervarix, Cintredekin besudotox (IL-13-PE38, IL-13-PE38QQR, Interleukin 13-pseudomonas exotoxin), Oncophage (HSPPC 96), Phenoxodiol (NV 06), IGN 101, PANVAC (CEA, MUC-1 vaccinia), ampligen, ibandronic acid, miltefosine, L-asparaginase, procarbazine, Trabectedin (ET-743, Ecteinascidin 743, Yondelis), 5,10-methylenetetrahydrofolate, hydroxycarbamide, pegaspargase, pentostatin, tazarotne, TransMID 107R (KSB 311), Trisenox, Telcyta, tretinoin, acitretin, Zometa (zolendronic acid), Pandimex (Aglycon protopanaxadiol, PBD-2131), Talabostat (PT100), Tesmilifene, Tetrandrine, halofuginone, rebimastat, removab, squalamine, ukrain, paditaxel, Zinecard, Vitaxin and the like.

To determine the binding of compounds having formula (I) to a representative protein kinase, the following in vitro kinase assay was used:

Recombinant GST-Plk1 (1-331) was expressed using the FastBac bacculovirus expression system (GIBCO BRL, Gaithersburg, Md.) and purified using glutathione (GST) affinity chromatography. Kinase reactions were conducted using 1 nM Plk1, 5 µM $\gamma$-$^{33}$P-ATP (2mCi/µmol), 2 µM biotinylated peptides substrate biotin-ahx-AKMETT FYDDAL-NASFLPSEKKK-amide (SEQ. ID. 1), and various concentrations of inhibitor in kinase buffer (25 mM Hepes pH 7.5, 1 mM DTT, 10 mM MgCl$_2$ 100 µM Na$_3$ VO$_4$ 0.075 mg/mL Triton X-100) for 30 min at ambient temperature prior to stopping the reaction with 50 mM EDTA. Stopped reactions were transferred to streptavidin-coated FlashPlates, the plates washed, and scintillation counted on a TopCount plate reader. Ki values of representative examples (µM) in are shown in TABLE 1.

TABLE 1

| | | | | | |
|---|---|---|---|---|---|
| 0.001 | 0.001 | 0.001 | 0.002 | 0.002 | 0.002 |
| 0.003 | 0.003 | 0.003 | 0.004 | 0.004 | 0.004 |
| 0.004 | 0.004 | 0.004 | 0.005 | 0.005 | 0.005 |
| 0.006 | 0.006 | 0.006 | 0.007 | 0.007 | 0.007 |
| 0.007 | 0.008 | 0.008 | 0.008 | 0.008 | 0.008 |
| 0.009 | 0.0096 | 0.0098 | 0.010 | 0.012 | 0.014 |
| 0.014 | 0.014 | 0.014 | 0.015 | 0.015 | 0.015 |
| 0.015 | 0.015 | 0.016 | 0.016 | 0.017 | 0.017 |
| 0.019 | 0.02 | 0.02 | 0.02 | 0.02 | 0.022 |
| 0.024 | 0.025 | 0.025 | 0.025 | 0.026 | 0.027 |
| 0.027 | 0.028 | 0.029 | 0.030 | 0.032 | 0.032 |
| 0.032 | 0.036 | 0.036 | 0.038 | 0.041 | 0.041 |
| 0.041 | 0.42 | 0.043 | 0.043 | 0.043 | 0.43 |
| 0.045 | 0.045 | 0.047 | 0.049 | 0.054 | 0.056 |
| 0.057 | 0.057 | 0.058 | 0.058 | 0.059 | 0.062 |
| 0.069 | 0.071 | 0.071 | 0.075 | 0.078 | 0.080 |
| 0.081 | 0.081 | 0.081 | 0.082 | 0.083 | 0.085 |
| 0.086 | 0.087 | 0.089 | 0.09 | 0.092 | 0.093 |
| 0.094 | 0.11 | 0.12 | 0.12 | 0.12 | 0.13 |
| 0.13 | 0.13 | 0.13 | 0.14 | 0.15 | 0.16 |
| 0.16 | 0.16 | 0.16 | 0.17 | 0.14 | 0.15 |
| 0.16 | 0.16 | 0.20 | 0.23 | 0.23 | 0.23 |
| 0.25 | 0.26 | 0.27 | 0.29 | 0.30 | 0.31 |
| 0.32 | 0.32 | 0.32 | 0.33 | 0.33 | 0.35 |
| 0.35 | 0.36 | 0.39 | 0.47 | 0.49 | 0.54 |
| 0.56 | 0.59 | 0.60 | 0.61 | 0.65 | 0.70 |
| 0.77 | 1.0 | 1.14 | 1.3 | 1.40 | 1.50 |
| 1.61 | 1.8 | 1.80 | 1.9 | 1.9 | 1.50 |
| 1.60 | 2.2 | 2.30 | 3.2 | 3.2 | 3.50 |
| 4.50 | 5 | 6.700 | 70 | 8.5 | 9.30 |
| 9.9 | 14 | 18 | 29 | >8.9 | >8.9 |
| >8.9 | >8.9 | >8.9 | >8.9 | >8.9 | >8.90 |
| >8.9 | >8.9 | >8.9 | >8.9 | >8.9 | >8.9 |
| >8.9 | >8.9 | >8.9 | >8.9 | >8.9 | >8.9 |
| 0.25 | | | | | |

The data from these assays demonstrate the utility of compounds having formula (I) as Plk1 inhibitors. Compounds having formula (I) are therefore expected to have utility in treatment of diseases during which Plk1 is expressed.

Diseases involving overexpression or unregulation of Plk1 include, but are not limited to, acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myleogeneous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, oropharyngeal carcinoma, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer, Wilms' tumor and the like.

It is also expected that compounds having formula (I) would inhibit the growth of cells derived from a cancer or neoplasm such as breast cancer (including estrogen-receptor positive breast cancer), colorectal cancer, endometrial cancer, lung cancer (including small cell lung cancer), lymphoma (including follicular or Diffuse Large B-cell), lymphoma (including non-Hodgkin's lymphoma), neuroblastoma, ovarian cancer, prostate cancer (including hormone-insensitive prostate cancer) and testicular cancer (including germ cell testicular cancer).

It is also expected that compounds having formula (I) would inhibit the growth of cells derived from a pediatric cancer or neoplasm such as embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer.

For example, involvement of Plk1 in non-small cell lung cancer is reported in Oncogene 14, 543-9 (1997).

Involvement of Plk1 in colorectal cancer is reported in Cancer Science. 94, 148-52 (2003).

Involvement of Plk1 in hepatoblastoma is reported in Oncogene 23, 5901-11 (2004).

Involvement of Plk1 in endometrial carcinoma is reported in Cancer Letters. 169, 41-9 (2001).

Involvement of Plk1 in ovarian carcinoma is reported in British Journal of Cancer 90, 815-21 (2004).

Involvement of Plk1 in squamous cell carcinomas is reported in Cancer Research. 59, 2794-7 (1999).

Involvement of Plk1 in oropharyngeal carcinomas is reported in International Journal of Oncology. 15, 687-92 (1999).

Involvement of Plk1 in esophageal carcinoma is reported in International Journal of Oncology. 15, 687-92 (1999).

Involvement of Plk1 in melanomas is reported in. JAMA 283, 479-80 (2000).

Involvement of Plk1 in malignant lymphoma of the thyroid is reported in Anticancer research 24, 259-63 (2004).

Involvement of Plk1 in non-Hodgkin's lymphomas is reported in Leukemia & Lymphoma 46, 225-31 (2005).

Involvement of Plk1 in epithelial ovarian cancer is reported in Journal of Clinical Oncology 15, 199-206, (1997).

Compounds having formula (I) may be made by synthetic chemical processes, examples of which are shown hereinbelow. It is meant to be understood that the order of the steps in the processes may be varied, that reagents, solvents and reaction conditions may be substituted for those specifically mentioned, and that vulnerable moieties may be protected and deprotected, as necessary.

Protecting groups for C(O)OH moieties include, but are not limited to, acetoxymethyl, allyl, benzoylmethyl, benzyl, benzyloxymethyl, tert-butyl, tert-butyldiphenylsilyl, diphenylmethyl, cyclobutyl, cyclohexyl, cyclopentyl, cyclopropyl, diphenylmethylsilyl, ethyl, para-methoxybenzyl, methoxymethyl, methoxyethoxymethyl, methyl, methylthiomethyl, naphthyl, para-nitrobenzyl, phenyl, n-propyl, 2,2,2-trichloroethyl, triethylsilyl, 2-(trimethylsilyl)ethyl, 2-(trimethylsilyl)ethoxymethyl, triphenylmethyl and the like.

Protecting groups for C(O) and C(O)H moieties include, but are not limited to, 1,3-dioxylketal, diethylketal, dimethylketal, 1,3-dithianylketal, O-methyloxime, O-phenyloxime and the like.

Protecting groups for NH moieties include, but are not limited to, acetyl, alanyl, benzoyl, benzyl (phenylmethyl), benzylidene, benzyloxycarbonyl (Cbz), tert-butoxycarbonyl (Boc), 3,4-dimethoxybenzyloxycarbonyl, diphenylmethyl, diphenylphosphoryl, formyl, methanesulfonyl, para-methoxybenzyloxycarbonyl, phenylacetyl, phthaloyl, succinyl, trichloroethoxycarbonyl, triethylsilyl, trifluoroacetyl, trimethylsilyl, triphenylmethyl, triphenylsilyl, para-toluenesulfonyl and the like.

Protecting groups for OH and SH moieties include, but are not limited to, acetyl, allyl, allyloxycarbonyl, benzyloxycarbonyl (Cbz), benzoyl, benzyl, tert-butyl, tert-butyldimethylsilyl, tert-butyldiphenylsilyl, 3,4-dimethoxybenzyl, 3,4-dimethoxybenzyloxycarbonyl, 1,1-dimethyl-2-propenyl, diphenylmethyl, formyl, methanesulfonyl, methoxyacetyl, 4-methoxybenzyloxycarbonyl, para-methoxybenzyl, methoxycarbonyl, methyl, para-toluenesulfonyl, 2,2,2-trichloroethoxycarbonyl, 2,2,2-trichloroethyl, triethylsilyl, trifluoroacetyl, 2-(trimethylsilyl)ethoxycarbonyl, 2-trimethylsilylethyl, triphenylmethyl, 2-(triphenylphosphonio)ethoxycarbonyl and the like.

The following abbreviations have the meanings indicated. ADDP means 1,1'-(azodicarbonyl)dipiperidine; AD-mix-13 means a mixture of $(DHQD)_2PHAL$, $K_3Fe(CN)_6$, $K_2CO_3$ and $K_2SO_4$); AIBN means 2,2'-azobis(2-methylpropionitrile); 9-BBN means 9-borabicyclo[3.3.1]nonane; Cp means cyclopentadiene; $(DHQD)_2PHAL$ means hydroquinidine 1,4-phthalazinediyl diethyl ether; DBU means 1,8-diazabicyclo [5.4.0]undec-7-ene; DIBAL means diisobutylaluminum hydride; DIEA means diisopropylethylamine; DMAP means N,N-dimethylaminopyridine; DME means 1,2-dimethoxyethane; DMF means N,N-dimethylformamide; dmpe means 1,2-bis(dimethylphosphino)ethane; DMSO means dimethylsulfoxide; dppa means diphenylphosphoryl azide; dppb means 1,4-bis(diphenylphosphino)butane; dppe means 1,2-bis(diphenylphosphino)ethane; dppf means 1,1'-bis(diphenylphosphino)ferrocene; dppm means 1,1-bis(diphenylphosphino)methane; EDAC means 1-(3-dimethylaminopropyl)-3-ethylcarbodiimide; Fmoc means fluorenylmethoxycarbonyl; HATU means O-(7-azabenzotriazol-1-yl)-N,N'N'N'-tetramethyluronium hexafluorophosphate; HMPA means hexamethylphosphoramide; IPA means isopropyl alcohol; LDA means lithium diisopropylamide; LHMDS means lithium bis(hexamethyldisilylamide); MP-$BH_3$ means macroporus triethylammonium methylpolystyrene cyanoborohydride; LAH means lithium aluminum hydride; NCS means N-chlorosuccinimide; PyBOP means benzotriazol-1-yloxytripyrrolidinophosphonium hexafluorophosphate; TDA-1 means tris(2-(2-methoxyethoxy)ethyl) amine; TEA means triethylamine; TFA means trifluoroacetic acid; THF means tetrahydrofuran; NCS means N-chlorosuccinimide; NMM means N-methylmorpholine; NMP means N-methylpyrrolidine and PPh₃ means triphenylphosphine.

SCHEME 1

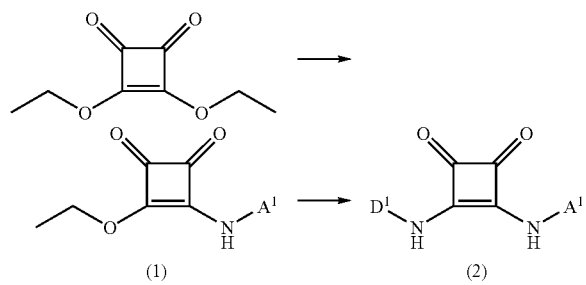

As shown in Scheme 1, 3,4-diethoxycyclobut-3-ene-1,2-dione can be reacted with compounds having formula $H_2N$-$A^1$ to provide compounds having formula (I). Compounds having formula (I) can be converted to compounds having formula (2) by reacting the former, an alkoxide base and compounds having formula $H_2N$-$D^1$ to provide compounds having formula (2). Conversion of 1,3,4-diethoxycyclobut-3-ene-1,2-dione to compounds having formula (I) is usually conducted in solvents such as methanol, ethanol or tert-butanol at about 25° C. over about 24 hours. Conversion of compounds having formula (I) to compounds having formula (2) is usually conducted in solvents such as DMSO at about 50° C. to 100° C. over about 24 hours.

SCHEME 2

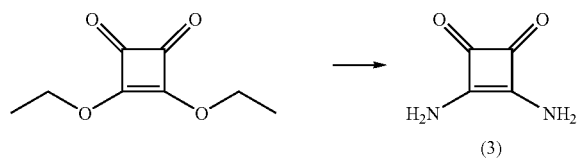

As shown in Scheme 2, 3,4-diethoxycyclobut-3-ene-1,2-dione can be reacted with ammonia in methanol to provide compounds having formula (3). The reaction is typically conducted at about 25° C. to about 50° C. over about 24 hours. Compounds having formula (3) can be reacted with the appropriately functionalized compounds having formula $ClC(O)R^1$, $ClC(O)OR^1$, $ClC(O)NHR^1$, $ClC(O)N(R^1)_2$, $ClSO_2NHR^1$ or $ClSO_2N(R^1)_2$, with or without a base, to provide compounds having formula (I). Examples of bases include, but are not limited to TEA, DIEA and the like. The degree of reactivity of the amino moieties can be determined by the molar ratios of the reactants, the temperatures at which the reactions are conducted, and whether or not a promoter such as DMAP is used.

The size, length and nature of substitution of $R^{2-4}$ and $R^{7-9}$ can be tailored according to the nature of substituents on the proximal ring. Rings having a desired substitution pattern may be purchased or derivatized by means well-known in the art. Accordingly, the following examples are presented to provide specifics of what is believed to be the most useful and readily understood description of procedures and conceptual aspects of this invention.

Example 1

A mixture of 3,4-diethoxycyclobut-3-ene-1,2-dione (1.9 g) and 1,2-dimethylpropylamine (0.87 g) in ethanol (10 mL) was stirred at ambient temperature overnight. The mixture was concentrated, and 15:1 pentane/ether was added. The solid was collected, washed with 15:1 pentane/ether and dried. ¹H NMR (DMSO-$d_6$) δ 0.83 (d, J=8 Hz, 6H), 1.16 (d, J=8 Hz, 3H), 1.38 (m, 3H), 1.67 (m, 1H), 3.42-3.82 (m, 1H), 4.63 (m, 2H), 8.55-8.75 (m, 1H).

Example 2

This example was prepared as described in EXAMPLE 1 using 1,3-dimethylbutylamine in place of 1,2-dimethylpropylamine. ¹H NMR (DMSO-$d_6$) δ 0.83 (d, J=8 Hz, 6H), 1.16 (d, J=8 Hz, 3H), 1.22 (m, 1H), 1.35 (m, 3H), 1.44 (m, 1H), 1.54 (m, 1H), 3.65-4.10 (m, 1H), 4.63 (m, 2H), 8.42-8.64 (m, 1H).

Example 3

This example was prepared as described in EXAMPLE 1 using (R)-1,2,2-trimethylpropylamine in place of 1,2-dimethylpropylamine. ¹H NMR (CDCl₃) δ 0.93 (s, 9H), 1.22 (d, J=8 Hz, 3H), 1.47 (m, 3H), 3.57 (m, 1H), 4.80 (m, 2H), 5.58 (m, 1H).

Example 4

This example was prepared as described in EXAMPLE 1 using (S)-1,2,2-trimethylpropylamine in place of 1,2-dimethylpropylamine. ¹H NMR (DMSO-$d_6$) δ 0.84 (s, 9H), 1.12 (d, J=8 Hz, 3H), 1.38 (m, 3H), 3.42-3.92 (m, 1H), 4.63 (m, 2H), 8.47-8.67 (m, 1H).

Example 5

This example was prepared as described in EXAMPLE 1 using 1,1-dimethylpropylamine in place of 1,2-dimethylpropylamine. ¹H NMR (DMSO-$d_6$) δ 0.80 (t, J=8 Hz, 3H), 1.24 (s, 6H), 1.38 (m, 3H), 1.62 (m, 2H), 4.70 (m, 2H), 8.47-8.57 (m, 1H).

Example 6

This example was prepared as described in EXAMPLE 1 using tert-butylamine in place of 1,2-dimethylpropylamine. ¹H NMR (DMSO-$d_6$) δ 1.32 (s, 9H), 1.38 (t, J=10 Hz, 3H), 4.70 (m, 2H), 8.66 (d, J=7 Hz, 1H).

Example 7

This example was prepared as described in EXAMPLE 1 using 2,2-dimethylpropylamine in place of 1,2-dimethylpropylamine.

Example 8

This example was prepared as described in EXAMPLE 1 using cyclopropylmethylamine in place of 1,2-dimethylpropylamine.

Example 9

This example was prepared as described in EXAMPLE 1 using 2-morpholin-4-yl-ethylamine in place of 1,2-dimethylpropylamine.

Example 10

This example was prepared as described in EXAMPLE 1 using 1-phenylethylamine in place of 1,2-dimethylpropylamine.

Example 11

A mixture of 3,4-diethoxycyclobut-3-ene-1,2-dione (1.7 g) and 4-trifluoromethoxyphenylamine (1.05 g) was stirred at ambient temperature for 3 days. 1:5 ethyl acetate/hexane was added, and the solid was collected, washed with 1:5 ethyl acetate/hexane and dried. $^1$H NMR (DMSO-$d_6$) δ 1.40 (t, J=8 Hz, 3H), 4.77 (q, J=8 Hz, 2H), 7.40 (d, J=8 Hz, 2H), 7.50 (d, J=8 Hz, 2H), 10.87 (s, 1H).

Example 12A

To 4-aminopyrimidine-2-thiol (0.254 g) was added water (3 mL), ammonium hydroxide (3 mL), tetrahydrofuran (20 mL) and 2M iodomethane in tert-butyl methyl ether (3 mL). The mixture was stirred at ambient temperature for 1.5 hours and concentrated. Ethyl acetate and water was added, and the organic phase was separated, dried over magnesium sulfate, filtered and concentrated. $^1$H NMR (CDCl$_3$) δ 2.50 (s, 3H), 4.90 (br s, 2H), 6.16 (d, J=6 Hz, 1H), 8.05 (d, J=6 Hz, 1H).

Example 12B

A mixture of EXAMPLE 3 (1.57 g), EXAMPLE 12A (1.48 g), N,N'-dimethylformamide (100 mL) and sodium ethoxide (21% (w/w) in ethanol, 3 mL) was heated at reflux overnight. The mixture was concentrated, water was added and concentrated hydrochloric acid was added to adjust the pH to ~2. The solution was filtered, and the solid was dried. $^1$H NMR (DMSO-$d_6$) δ 0.95 (s, 9H), 1.22 (d, J=8 Hz, 3H), 2.50 (s, 3H), 4.08 (m, 1H), 7.12 (m, 1H), 8.17 (d, J=10 Hz, 1H), 8.41 (d, J=6 Hz, 1H), 11.01 (br s, 1H).

Example 12C

A mixture of Oxone® (14.2 g) in water (100 mL) was added slowly to a solution of EXAMPLE 12B (2.03 g) in methanol (120 mL). The mixture was stirred at ambient temperature overnight and partially concentrated. The solution was filtered and the solid washed with water and ethanol and dried. $^1$H NMR (DMSO-$d_6$) δ 0.95 (s, 9H), 1.22 (d, J=8 Hz, 3H), 3.40 (s, 3H), 4.22 (m, 1H), 7.49 (m, 1H), 8.34 (d, J=10 Hz, 1H), 8.70 (d, J=6 Hz, 1H), 11.60 (br s, 1H).

Example 12D

A mixture of EXAMPLE 12C (15 mg), 3,4,5-trimethoxyphenylamine (18.3 mg), and p-toluenesulfonic acid in tetrahydrofuran (0.5 mL) was heated at 88° C. overnight. The mixture was purified by preparative HPLC on a C8 column using a gradient of 10% to 100% acetonitrile/water containing 0.1% trifluoroacetic acid to give the desired product as the trifluoroacetate salt. $^1$H NMR (DMSO-$d_6$) δ 0.88 (s, 9H), 1.09 (d, J=8 Hz, 3H), 3.64 (s, 3H), 3.77 (s, 6H), 3.97 (m, 1H), 6.97 (s, 2H), 7.28 (d, J=6 Hz, 1H), 7.91 (d, J=10 Hz, 1H), 8.28 (d, J=6 Hz, 1H), 9.27 (s, 1H), 10.39 (br s, 1H).

Example 13

This example as the trifluoroacetate salt was prepared as described in EXAMPLE 12D using (R)-1-phenylethylamine in place of 3,4,5-trimethoxyphenylamine. $^1$H NMR (DMSO-$d_6$) δ 0.90 (s, 9H), 1.19 (d, J=8 Hz, 3H), 1.48 (d, J=8 Hz, 3H), 3.99 (m, 1H), 5.22 (m, 1H), 7.20 (m, 2H), 7.38 (m, 4H), 8.04 (d, J=10 Hz, 1H), 8.17 (d, J=6 Hz, 1H), 10.56 (br s, 1H).

Example 14

This example as the trifluoroacetate salt was prepared as described in EXAMPLE 12D using 4-bromophenylamine in place of 3,4,5-trimethoxyphenylamine. $^1$H NMR (DMSO-$d_6$) δ 0.88 (s, 9H), 1.16 (d, J=8 Hz, 3H), 4.00 (m, 1H), 7.40 (d, J=6 Hz, 1H), 7.48 (d, J=8 Hz, 2H), 7.66 (d, J=8 Hz, 2H), 7.96 (d, J=10 Hz, 1H), 8.32 (d, J=6 Hz, 1H), 9.51 (s, 1H), 10.26 (br s, 1H).

Example 15

This example as the trifluoroacetate salt was prepared as described in EXAMPLE 12D using benzo[1,3]dioxol-5-ylamine in place of 3,4,5-trimethoxyphenylamine. $^1$H NMR (DMSO-$d_6$) δ 0.88 (s, 9H), 1.16 (d, J=8 Hz, 3H), 3.98 (m, 1H), 5.98 (s, 2H), 6.87 (d, J=8 Hz, 1H), 7.00 (d, J=8 Hz, 1H), 7.31 (s, 1H), 7.38 (d, J=6 Hz, 1H), 8.00 (d, J=10 Hz, 1H), 8.24 (d, J=6 Hz, 1H), 9.41 (s, 1H), 10.31 (br s, 1H).

Example 16

This example as the trifluoroacetate salt was prepared as described in EXAMPLE 12D using 4-trifluoromethoxyphenylamine in place of 3,4,5-trimethoxyphenylamine. $^1$H NMR (DMSO-$d_6$) δ 0.89 (s, 9H), 1.17 (d, J=8 Hz, 3H), 3.99 (m, 1H), 7.30 (d, J=8 Hz, 2H), 7.42 (d, J=6 Hz, 1H), 7.77 (d, J=8 Hz, 2H), 7.99 (d, J=10 Hz, 1H), 8.34 (d, J=6 Hz, 1H), 9.61 (s, 1H), 10.30 (br s, 1H).

Example 17

This example as the trifluoroacetate salt was prepared as described in EXAMPLE 12D using 3-methylphenylamine in place of 3,4,5-trimethoxyphenylamine. $^1$H NMR (DMSO-$d_6$) δ 0.88 (s, 9H), 1.17 (d, J=8 Hz, 3H), 2.28 (s, 3H), 3.99 (m, 1H), 6.82 (d, J=8 Hz, 1H), 7.20 (t, J=8 Hz, 1H), 7.38 (m, 2H), 7.56 (d, J=8 Hz, 1H), 8.01 (d, J=10 Hz, 1H), 8.30 (d, J=6 Hz, 1H), 9.35 (s, 1H), 10.32 (br s, 1H).

Example 18

This example as the trifluoroacetate salt was prepared as described in EXAMPLE 12D using 4-fluorophenylamine in place of 3,4,5-trimethoxyphenylamine $^1$H NMR (DMSO-$d_6$) δ 0.89 (s, 9H), 1.17 (d, J=8 Hz, 3H), 3.99 (m, 1H), 7.18 (t, J=8 Hz, 2H), 7.42 (d, J=6 Hz, 1H), 7.66 (m, 2H), 8.01 (d, J=10 Hz, 1H), 8.30 (d, J=6 Hz, 1H), 9.50 (s, 1H), 10.30 (br s, 1H).

Example 19

This example as the trifluoroacetate salt was prepared as described in EXAMPLE 12D using 2-isopropylphenylamine in place of 3,4,5-trimethoxyphenylamine. $^1$H NMR (DMSO-$d_6$) δ 0.88 (s, 9H), 1.17 (d, J=8 Hz, 3H), 1.18 (d, J=8 Hz, 6H), 3.18 (m, 1H), 3.98 (m, 1H), 7.22 (m, 3H), 7.38 (m, 2H), 8.03 (d, J=10 Hz, 1H), 8.20 (d, J=6 Hz, 1H), 9.00 (s, 1H), 10.28 (br s, 1H).

Example 20

This example as the trifluoroacetate salt was prepared as described in EXAMPLE 12D using 4-chlorophenylamine in place of 3,4,5-trimethoxyphenylamine. ¹H NMR (DMSO-d₆) δ 0.88 (s, 9H), 1.11 (d, J=8 Hz, 3H), 3.97 (m, 1H), 7.30 (d, J=8 Hz, 2H), 7.37 (d, J=6 Hz, 1H), 7.66 (d, J=8 Hz, 2H), 7.95 (d, J=10 Hz, 1H), 8.28 (d, J=6 Hz, 1H), 9.45 (s, 1H), 10.20 (br s, 1H).

Example 21

This example as the trifluoroacetate salt was prepared as described in EXAMPLE 20 using aniline in place of 4-fluoro-3-methylphenylamine ¹H NMR (DMSO-d₆) δ 0.90 (s, 9H), 1.13 (d, J=7 Hz, 3H), 4.00 (m, 1H), 6.98 (m, 1H), 7.29 (t, J=8 Hz, 2H), 7.40 (t, J=6 Hz, 1H), 8.68 (d, J=8 Hz, 2H), 8.00 (d, J=8 Hz, 1H), 8.31 (d, J=6 Hz, 1H), 9.38 (s, 1H), 10.25 (s, 1H).

Example 22

This example as the trifluoroacetate salt was prepared as described in EXAMPLE 20 using 2-naphthylamine in place of 4-fluoro-3-methylphenylamine. ¹H NMR (DMSO-d₆) δ 0.90 (s, 9H), 1.13 (d, J=7 Hz, 3H), 4.00 (m, 1H), 7.38 (m, 2H), 7.45 (t, J=8 Hz, 1H), 7.80 (m, 4H), 7.98 (d, J=8 Hz, 1H), 8.26 (s, 1H), 8.36 (d, J=6 Hz, 1H), 9.53 (s, 1H), 10.29 (s, 1H).

Example 23

This example as the trifluoroacetate salt was prepared as described in EXAMPLE 20 using 3-bromo-4-methylphenylamine in place of 4-fluoro-3-methylphenylamine. ¹H NMR (DMSO-d₆) δ 0.90 (s, 9H), 1.13 (d, J=7 Hz, 3H), 2.29 (s, 3H), 4.00 (m, 1H), 7.26 (d, J=8 Hz, 1H), 7.36 (d, J=6 Hz, 1H), 7.65 (d, J=8 Hz, 1H), 7.90 (s, 4H), 7.98 (d, J=8 Hz, 1H), 8.33 (d, J=6 Hz, 1H), 9.35 (s, 1H), 10.25 (s, 1H).

Example 24

This example as the trifluoroacetate salt was prepared as described in EXAMPLE 20 using 4-aminobiphenyl in place of 4-fluoro-3-methylphenylamine. ¹H NMR (DMSO-d₆) δ 0.90 (s, 9H), 1.15 (d, J=7 Hz, 3H), 4.00 (m, 1H), 7.32 (t, J=8 Hz, 1H), 7.39 (d, J=6 Hz, 1H), 7.45 (t, J=8 Hz, 2H), 7.65 (t, J=8 Hz, 4H), 7.78 (d, J=8 Hz, 2H), 7.98 (d, J=8 Hz, 1H), 8.33 (d, J=6 Hz, 1H), 9.52 (s, 1H), 10.28 (s, 1H).

Example 25

This example as the trifluoroacetate salt was prepared as described in EXAMPLE 20 using 4-phenoxyphenylamine in place of 4-fluoro-3-methylphenylamine. ¹H NMR (DMSO-d₆) δ 0.90 (s, 9H), 1.15 (d, J=7 Hz, 3H), 4.00 (m, 1H), 6.99 (t, J=8 Hz, 4H), 7.10 (t, J=8 Hz, 1H), 7.38 (m, 3H), 7.67 (d, J=8 Hz, 2H), 7.99 (d, J=8 Hz, 1H), 8.30 (d, J=6 Hz, 1H), 9.42 (s, 1H), 10.26 (s, 1H).

Example 26

This example as the trifluoroacetate salt was prepared as described in EXAMPLE 20 using 3-phenoxyphenylamine in place of 4-fluoro-3-methylphenylamine. ¹H NMR (DMSO-d₆) δ 0.90 (s, 9H), 1.15 (d, J=7 Hz, 3H), 4.00 (m, 1H), 6.57 (d, J=6 Hz, 1H), 7.04 (d, J=8 Hz, 2H), 7.12 (t, J=8 Hz, 1H), 7.28 (t, J=8 Hz, 1H), 7.38 (m, 4H), 7.52 (d, J=6 Hz, 1H), 7.98 (d, J=8 Hz, 1H), 8.30 (d, J=6 Hz, 1H), 9.46 (s, 1H), 10.26 (s, 1H).

Example 27

This example as the trifluoroacetate salt was prepared as described in EXAMPLE 20 using 2,3-dimethoxyphenylamine in place of 4-fluoro-3-methylphenylamine. ¹H NMR (DMSO-d₆) δ 0.91 (s, 9H), 1.18 (d, J=7 Hz, 3H), 3.74 (s, 3H), 3.82 (s, 3H), 4.00 (m, 1H), 6.75 (d, J=8 Hz, 1H), 7.01 (m, 1H), 7.26 (d, J=6 Hz, 1H), 7.79 (d, J=8 Hz, 1H), 7.88 (s, 1H), 8.01 (d, J=8 Hz, 1H), 8.31 (d, J=6 Hz, 1H), 10.40 (s, 1H).

Example 28

This example as the trifluoroacetate salt was prepared as described in EXAMPLE 20 using 2,3-dihydrobenzo[1,4]dioxin-6-ylamine in place of 4-fluoro-3-methylphenylamine ¹H NMR (DMSO-d₆) δ 0.91 (s, 9H), 1.18 (d, J=7 Hz, 3H), 4.00 (m, 1H), 4.22 (m, 4H), 6.79 (d, J=8 Hz, 1H), 7.03 (d, J=8 Hz, 1H), 7.22 (s, 1H), 7.37 (d, J=6 Hz, 1H), 8.04 (d, J=8 Hz, 1H), 8.26 (d, J=6 Hz, 1H), 9.32 (s, 1H), 10.30 (s, 1H).

Example 29

This example as the trifluoroacetate salt was prepared as described in EXAMPLE 20 using 1-naphthylamine in place of 4-fluoro-3-methylphenylamine. ¹H NMR (DMSO-d₆) δ 0.91 (s, 9H), 1.18 (d, J=7 Hz, 3H), 4.00 (m, 1H), 7.40 (d, J=6 Hz, 1H), 7.52 (m, 3H), 7.65 (d, J=8 Hz, 1H), 7.82 (d, J=8 Hz, 1H), 7.99 (m, 3H), 8.25 (d, J=6 Hz, 1H), 9.50 (s, 1H), 10.32 (s, 1H).

Example 30

This example as the trifluoroacetate salt was prepared as described in EXAMPLE 20 using 2,4-dimethoxyphenylamine in place of 4-fluoro-3-methylphenylamine. ¹H NMR (DMSO-d₆) δ 0.91 (s, 9H), 1.18 (d, J=7 Hz, 3H), 3.78 (s, 3H), 3.81 (s, 3H), 4.00 (m, 1H), 6.58 (d, J=6 Hz, 1H), 6.70 (s, 1H), 7.35 (br s, 1H), 7.58 (br s, 1H), 8.10 (d, J=8 Hz, 1H), 8.21 (d, J=6 Hz, 1H), 8.70 (br s, 1H), 10.67 (s, 1H).

Example 31

This example as the trifluoroacetate salt was prepared as described in EXAMPLE 20 using 2,5-dimethoxyphenylamine in place of 4-fluoro-3-methylphenylamine. ¹H NMR (DMSO-d₆) δ 0.91 (s, 9H), 1.18 (d, J=7 Hz, 3H), 3.72 (s, 3H), 3.80 (s, 3H), 4.00 (m, 1H), 6.81 (d, J=8 Hz, 1H), 7.00 (d, J=6 Hz, 1H), 7.21 (m, 1H), 7.80 (s, 1H), 8.06 (d, J=8 Hz, 1H), 8.10 (br s, 1H), 8.31 (d, J=6 Hz, 1H), 10.69 (s, 1H).

Example 32

This example as the trifluoroacetate salt was prepared as described in EXAMPLE 20 using 3-aminobiphenyl in place of 4-fluoro-3-methylphenylamine. ¹H NMR (DMSO-d₆) δ 0.90 (s, 9H), 1.15 (d, J=7 Hz, 3H), 4.00 (m, 1H), 7.28 (d, J=8 Hz, 1H), 7.35 (m, 3H), 7.43 (t, J=8 Hz, 2H), 7.63 (d, J=8 Hz, 2H), 7.78 (d, J=8 Hz, 1H), 7.85 (s, 1H), 7.98 (d, J=8 Hz, 1H), 8.33 (d, J=6 Hz, 1H), 9.42 (s, 1H), 10.29 (s, 1H).

Example 33

This example as the trifluoroacetate salt was prepared as described in EXAMPLE 20 using 4-methoxyphenylamine in place of 4-fluoro-3-methylphenylamine. ¹H NMR (DMSO-d₆) δ 0.89 (s, 9H), 1.15 (d, J=7 Hz, 3H), 3.72 (s, 3H), 4.00 (m, 1H), 6.91 (d, J=8 Hz, 2H), 7.35 (d, J=6 Hz, 1H), 7.52 (d, J=8 Hz, 2H), 8.00 (d, J=8 Hz, 1H), 8.22 (d, J=6 Hz, 1H), 9.20 (s, 1H), 10.28 (s, 1H).

Example 34

This example as the trifluoroacetate salt was prepared as described in EXAMPLE 20 using 3-chlorophenylamine in place of 4-fluoro-3-methylphenylamine. ¹H NMR (DMSO-d₆) δ 0.90 (s, 9H), 1.15 (d, J=7 Hz, 3H), 4.01 (m, 1H), 7.00 (d, J=8 Hz, 1H), 7.30 (t, J=8 Hz, 1H), 7.41 (d, J=6 Hz, 1H), 7.68 (d, J=8 Hz, 1H), 7.81 (s, 1H), 7.98 (d, J=8 Hz, 1H), 8.35 (d, J=6 Hz, 1H), 9.52 (s, 1H), 10.28 (s, 1H).

Example 35

This example as the trifluoroacetate salt was prepared as described in EXAMPLE 20 using 3-bromophenylamine in place of 4-fluoro-3-methylphenylamine. ¹H NMR (DMSO-d₆) δ 0.90 (s, 9H), 1.15 (d, J=7 Hz, 3H), 4.01 (m, 1H), 7.11 (d, J=8 Hz, 1H), 7.28 (t, J=8 Hz, 1H), 7.39 (d, J=6 Hz, 1H), 7.73 (d, J=8 Hz, 1H), 7.91 (s, 1H), 7.98 (d, J=8 Hz, 1H), 8.35 (d, J=6 Hz, 1H), 9.45 (s, 1H), 10.23 (s, 1H).

Example 36

This example as the trifluoroacetate salt was prepared as described in EXAMPLE 20 using 3-isopropoxyphenylamine in place of 4-fluoro-3-methylphenylamine. ¹H NMR (DMSO-d₆) δ 0.90 (s, 9H), 1.15 (d, J=7 Hz, 3H), 1.28 (d, J=4 Hz, 6H), 3.98 (m, 1H), 4.55 (m, 1H), 6.56 (d, J=8 Hz, 1H), 7.18 (m, 2H), 7.30 (d, J=8 Hz, 1H), 7.35 (d, J=6 Hz, 1H), 7.98 (d, J=8 Hz, 1H), 8.30 (d, J=6 Hz, 1H), 9.30 (s, 1H), 10.28 (s, 1H).

Example 37

This example as the trifluoroacetate salt was prepared as described in EXAMPLE 20 using 4-morpholin-4-ylphenylamine in place of 4-fluoro-3-methylphenylamine. ¹H NMR (DMSO-d₆) δ 0.90 (s, 9H), 1.15 (d, J=7 Hz, 3H), 3.08 (t, J=5 Hz, 4H), 3.72 (t, J=5 Hz, 4H), 3.98 (m, 1H), 6.93 (d, J=8 Hz, 2H), 7.38 (d, J=6 Hz, 1H), 7.46 (d, J=8 Hz, 2H), 8.00 (d, J=8 Hz, 1H), 8.25 (d, J=6 Hz, 1H), 9.38 (s, 1H), 10.38 (s, 1H).

Example 38

This example as the trifluoroacetate salt was prepared as described in EXAMPLE 20 using 3-aminobenzonitrile in place of 4-fluoro-3-methylphenylamine ¹H NMR (DMSO-d₆) δ 0.90 (s, 9H), 1.15 (d, J=7 Hz, 3H), 4.00 (m, 1H), 7.06 (d, J=8 Hz, 1H), 7.32 (t, J=8 Hz, 1H), 7.39 (d, J=6 Hz, 1H), 7.75 (s, 1H), 7.81 (d, J=8 Hz, 1H), 8.00 (d, J=8 Hz, 1H), 8.25 (d, J=6 Hz, 1H), 9.42 (s, 1H), 10.28 (s, 1H).

Example 39

This example as the trifluoroacetate salt was prepared as described in EXAMPLE 20 using 3,4-difluorophenylamine in place of 4-fluoro-3-methylphenylamine. ¹H NMR (DMSO-d₆) δ 0.90 (s, 9H), 1.18 (d, J=7 Hz, 3H), 4.02 (m, 1H), 7.38 (m, 1H), 7.42 (m, 2H), 7.88 (m, 1H), 7.95 (d, J=8 Hz, 1H), 8.35 (d, J=6 Hz, 1H), 9.58 (s, 1H), 10.23 (s, 1H).

Example 40

This example as the trifluoroacetate salt was prepared as described in EXAMPLE 20 using 3-chloro-4-fluorophenylamine in place of 4-fluoro-3-methylphenylamine. ¹H NMR (DMSO-d₆) δ 0.90 (s, 9H), 1.15 (d, J=7 Hz, 3H), 4.00 (m, 1H), 7.32 (t, J=8 Hz, 1H), 7.40 (d, J=6 Hz, 1H), 7.68 (m, 1H), 7.92 (m, 2H), 8.35 (d, J=6 Hz, 1H), 9.43 (s, 1H), 10.20 (s, 1H).

Example 41

This example as the trifluoroacetate salt was prepared as described in EXAMPLE 20 using 3-trifluoromethylphenylamine in place of 4-fluoro-3-methylphenylamine. ¹H NMR (DMSO-d₆) δ 0.90 (s, 9H), 1.15 (d, J=7 Hz, 3H), 4.00 (m, 1H), 7.28 (d, J=8 Hz, 1H), 7.39 (d, J=6 Hz, 1H), 7.55 (t, J=8 Hz, 1H), 7.98 (m, 2H), 8.08 (d, J=8 Hz, 1H), 8.38 (d, J=6 Hz, 1H), 9.56 (s, 1H), 10.25 (s, 1H).

Example 42

This example as the trifluoroacetate salt was prepared as described in EXAMPLE 20 using 9H-fluoren-2-ylamine in place of 4-fluoro-3-methylphenylamine. ¹H NMR (DMSO-d₆) δ 0.90 (s, 9H), 1.15 (d, J=7 Hz, 3H), 3.90 (s, 2H), 4.00 (m, 1H), 7.25 (t, J=8 Hz, 1H), 7.35 (m, 2H), 7.55 (d, J=8 Hz, 1H), 7.70 (d, J=8 Hz, 1H), 7.80 (d, J=8 Hz, 2H), 7.98 (m, 2H), 8.35 (d, J=6 Hz, 1H), 9.42 (s, 1H), 10.25 (s, 1H).

Example 43

A mixture of EXAMPLE 3 (30 mg), 4'-aminobiphenyl-4-carbonitrile (20 mg), tetrahydrofuran (2 mL), and trifluoroacetic acid (50 µL) was heated to 70° C. and stirred overnight. The mixture was cooled, concentrated, and the residue purified as described in EXAMPLE 12D to give 6 mg of the title compound as the trifluoroacetate salt. ¹H NMR (DMSO-d₆) δ 0.89 (s, 9H), 1.15 (d, J=7 Hz, 3H), 4.00 (m, 1H), 7.43 (d, J=6 Hz, 1H), 7.73 (d, J=8 Hz, 2H), 7.86 (m, 6H), 8.00 (d, J=8 Hz, 1H), 8.38 (d, J=6 Hz, 1H), 9.65 (s, 1H), 10.35 (s, 1H).

Example 44

This example as the trifluoroacetate salt was prepared as described in EXAMPLE 43 using 2'-methoxybiphenyl-4-ylamine in place of 4'-aminobiphenyl-4-carbonitrile. ¹H NMR (DMSO-d₆) δ 0.89 (s, 9H), 1.15 (d, J=7 Hz, 3H), 3.78 (s, 3H), 4.00 (m, 1H), 7.02 (m, 1H), 7.11 (d, J=8 Hz, 1H), 7.32 (m, 2H), 7.41 (d, J=6 Hz, 1H), 7.45 (d, J=8 Hz, 2H), 7.70 (d, J=8 Hz, 2H), 8.00 (d, J=8 Hz, 1H), 8.32 (d, J=6 Hz, 1H), 9.50 (s, 1H), 10.32 (s, 1H).

Example 45

This example as the trifluoroacetate salt was prepared as described in EXAMPLE 43 using 4-imidazol-1-ylphenylamine in place of 4'-aminobiphenyl-4-carbonitrile. ¹H NMR (DMSO-d₆) δ 0.90 (s, 9H), 1.15 (d, J=7 Hz, 3H), 4.02 (m, 1H), 6.75 (d, J=8 Hz, 2H), 7.52 (d, J=8 Hz, 2H), 7.62 (d, J=6 Hz, 1H), 7.78 (m, 1H), 8.00 (d, J=8 Hz, 1H), 8.36 (s, 1H), 8.62 (s, 1H), 8.75 (d, J=6 Hz, 1H), 10.38 (s, 1H), 11.12 (s, 1H).

Example 46

This example as the trifluoroacetate salt was prepared as described in EXAMPLE 43 using 4'-methoxybiphenyl-4-ylamine in place of 4'-aminobiphenyl-4-carbonitrile. ¹H NMR (DMSO-d₆) δ 0.89 (s, 9H), 1.15 (d, J=7 Hz, 3H), 3.78 (s, 3H), 4.01 (m, 1H), 6.99 (d, J=8 Hz, 2H), 7.38 (d, J=6 Hz, 1H), 7.48 (dd, J=8 Hz, 4H), 7.73 (d, J=8 Hz, 2H), 8.00 (d, J=8 Hz, 1H), 8.35 (d, J=6 Hz, 1H), 9.48 (s, 1H), 10.28 (s, 1H).

Example 47

This example as the trifluoroacetate salt was prepared as described in EXAMPLE 43 using 4-dimethylaminophenylamine in place of 4'-aminobiphenyl-4-carbonitrile. ¹H NMR (DMSO-d₆) δ 0.91 (s, 9H), 1.15 (d, J=7 Hz, 3H), 3.00 (s, 6H), 3.99 (m, 1H), 7.15 (d, J=8 Hz, 2H), 7.45 (d, J=6 Hz, 2H), 7.55 (d, J=8 Hz, 2H), 8.06 (d, J=8 Hz, 1H), 8.30 (d, J=6 Hz, 1H), 9.79 (s, 1H), 10.52 (s, 1H).

Example 48

This example as the trifluoroacetate salt was prepared as described in EXAMPLE 43 using 4-methoxyphenylmethylamine in place of 4'-aminobiphenyl-4-carbonitrile. $^1$H NMR (DMSO-d$_6$) δ 0.89 (s, 9H), 1.15 (d, J=7 Hz, 3H), 3.77 (s, 3H), 3.41 (s, 3H), 4.01 (m, 1H), 6.97 (m, 2H), 7.24 (m, 3H), 7.85 (m, 1H), 7.99 (m, 1H), 8.20 (d, J=6 Hz, 1H).

Example 49

This example as the trifluoroacetate salt was prepared as described in EXAMPLE 43 using 4'-chlorobiphenyl-4-ylamine in place of 4'-aminobiphenyl-4-carbonitrile. $^1$H NMR (DMSO-d$_6$) δ 0.89 (s, 9H), 1.15 (d, J=7 Hz, 3H), 4.01 (m, 1H), 7.40 (d, J=6 Hz, 1H), 7.48 (d, J=8 Hz, 2H), 7.65 (d, J=8 Hz, 2H), 7.70 (d, J=8 Hz, 2H), 7.79 (d, J=8 Hz, 2H), 8.00 (d, J=8 Hz, 1H), 8.35 (d, J=6 Hz, 1H), 9.53 (s, 1H), 10.31 (s, 1H).

Example 50

This example as the trifluoroacetate salt was prepared as described in EXAMPLE 43 using 4-[1,2,3]thiadiazol-4-ylphenylamine in place of 4'-aminobiphenyl-4-carbonitrile. $^1$H NMR (DMSO-d$_6$) δ 0.89 (s, 9H), 1.15 (d, J=7 Hz, 3H), 4.01 (m, 1H), 7.25 (d, J=6 Hz, 1H), 7.86 (d, J=8 Hz, 2H), 8.02 (d, J=8 Hz, 1H), 8.09 (d, J=8 Hz, 2H), 8.35 (d, J=6 Hz, 1H), 9.43 (s, 1H), 9.69 (s, 1H), 10.36 (s, 1H).

Example 51

This example as the trifluoroacetate salt was prepared as described in EXAMPLE 43 using 4-thiophen-2-ylphenylamine in place of 4'-aminobiphenyl-4-carbonitrile. $^1$H NMR (DMSO-d$_6$) δ 0.90 (s, 9H), 1.15 (d, J=7 Hz, 3H), 4.01 (m, 1H), 7.15 (m, 1H), 7.42 (m, 2H), 7.48 (d, J=6 Hz, 1H), 7.58 (d, J=8 Hz, 2H), 7.75 (d, J=8 Hz, 2H), 7.98 (d, J=8 Hz, 1H), 8.35 (d, J=6 Hz, 1H), 9.42 (s, 1H), 10.26 (s, 1H).

Example 52

This example as the trifluoroacetate salt was prepared as described in EXAMPLE 43 using 6-aminobenzothiazole in place of 4'-aminobiphenyl-4-carbonitrile. $^1$H NMR (DMSO-d$_6$) δ 0.90 (s, 9H), 1.12 (d, J=7 Hz, 3H), 3.98 (m, 1H), 7.42 (d, J=6 Hz, 1H), 7.71 (d, J=8 Hz, 1H), 8.00 (d, J=8 Hz, 1H), 8.05 (d, J=8 Hz, 1H), 8.35 (d, J=6 Hz, 1H), 8.58 (s, 1H), 9.22 (s, 1H), 9.86 (s, 1H), 10.46 (s, 1H).

Example 53A

This example was prepared as described in EXAMPLE 12B using EXAMPLE 6 in place of EXAMPLE 3. $^1$H NMR (DMSO-d$_6$) δ 1.46 (s, 9H), 2.52 (s, 3H), 7.25 (d, J=10 Hz, 1H), 8.42 (d, J=10 Hz, 1H), 8.69 (s, 1H), 10.96 (s, 1H).

Example 53B

This example was prepared as described in EXAMPLE 12C using EXAMPLE 53A in place of EXAMPLE 12B. $^1$H NMR (DMSO-d$_6$) δ 1.46 (s, 9H), 3.40 (s, 3H), 7.25 (d, J=10 Hz, 1H), 8.40 (d, J=10 Hz, 1H), 8.60 (s, 1H), 11.40 (s, 1H).

Example 53C

A mixture of EXAMPLE 53B (30 mg), 9H-fluoren-2-ylamine (18 mg, 0.11 mmol), tetrahydrofuran (2 mL), and trifluoroacetic acid (50 uL) was heated to 70° C. and stirred overnight. The mixture was cooled, concentrated and the residue purified as described in EXAMPLE 12D to give 2 mg of the title compound as the trifluoroacetate salt. $^1$H NMR (DMSO-d$_6$) δ 1.35 (s, 9H), 3.88 (s, 2H), 7.19 (m, 2H), 7.32 (t, J=8 Hz, 1H), 7.55 (d, J=8 Hz, 1H), 7.70 (d, J=8 Hz, 1H), 7.70 (d, J=8 Hz, 2H), 7.92 (s, 1H), 8.30 (s, 1H), 8.35 (d, J=6 Hz, 1H), 9.42 (s, 1H), 10.48 (s, 1H).

Example 54

3-tert-butylamino-4-(2-(4-fluoro-3-methylphenylamino)pyrimidin-4-ylamino)cyclobut-3-ene-1,2-dione This example as the trifluoroacetate salt was prepared as described in EXAMPLE 53C using 4-fluoro-3-methylphenylamine in place of 9H-fluoren-2-ylamine. $^1$H NMR (DMSO-d$_6$) δ 1.36 (s, 9H), 2.21 (s, 3H), 7.08 (t, J=8 Hz, 1H), 7.16 (d, J=6 Hz, 1H), 7.50 (m, 2H), 8.22 (m, 2H), 9.38 (s, 1H), 10.53 (s, 1H).

Example 55

This example as the trifluoroacetate salt was prepared as described in EXAMPLE 53C using 6-aminobenzthiazole in place of 9H-fluoren-2-ylamine. $^1$H NMR (DMSO-d$_6$) δ 1.36 (s, 9H), 7.26 (d, J=6 Hz, 1H), 7.71 (d, J=8 Hz, 1H), 8.00 (d, J=8 Hz, 1H), 8.25 (s, 1H), 8.35 (d, J=6 Hz, 1H), 8.60 (s, 1H), 9.20 (s, 1H), 9.68 (s, 1H), 10.49 (s, 1H).

Example 56

This example as the trifluoroacetate salt was prepared as described in EXAMPLE 53C using 4-[1,2,3]thiadiazol-4-ylphenylamine in place of 9H-fluoren-2-ylamine. $^1$H NMR (DMSO-d$_6$) δ 1.38 (s, 9H), 7.26 (d, J=6 Hz, 1H), 7.88 (d, J=8 Hz, 2H), 8.08 (d, J=8 Hz, 2H), 8.28 (s, 1H), 8.36 (d, J=6 Hz, 1H), 9.63 (s, 1H), 10.48 (s, 1H).

Example 57

This example as the trifluoroacetate salt was prepared as described in EXAMPLE 53C using 4-methylpiperazin-1-ylphenylamine in place of 9H-fluoren-2-ylamine. $^1$H NMR (DMSO-d$_6$) δ 1.35 (s, 9H), 2.88 (s, 3H), 2.93 (m, 2H), 3.25 (m, 2H), 3.52 (m, 2H), 3.75 (m, 2H), 6.95 (d, J=8 Hz, 2H), 7.09 (d, J=6 Hz, 1H), 7.52 (d, J=8 Hz, 2H), 8.25 (d, J=6 Hz, 2H), 9.25 (s, 1H), 10.52 (s, 1H).

Example 58

This example as the trifluoroacetate salt was prepared as described in EXAMPLE 53C using 4-hydroxy-3-methylphenylamine in place of 9H-fluoren-2-ylamine. $^1$H NMR (DMSO-d$_6$) δ 1.35 (s, 9H), 2.10 (s, 3H), 6.76 (d, J=8 Hz, 1H), 7.16 (m, 3H), 8.18 (d, J=8 Hz, 1H), 8.29 (s, 1H), 9.11 (s, 1H), 9.25 (br s, 1H), 10.63 (br s, 1H).

Example 59

This example as the trifluoroacetate salt was prepared as described in EXAMPLE 53C using 5-aminoindane in place of 9H-fluoren-2-ylamine. ¹H NMR (DMSO-d₆) δ 1.35 (s, 9H), 2.00 (t, J=8 Hz, 2H), 2.83 (m, 4H), 7.13 (m, 2H), 7.36 (d, J=8 Hz, 1H), 8.28 (m, 2H), 9.11 (s, 1H), 9.33 (s, 1H), 10.53 (s, 1H).

Example 60

This example as the trifluoroacetate salt was prepared as described in EXAMPLE 53C using 4-morpholin-4-ylphenylamine in place of 9H-fluoren-2-ylamine. ¹H NMR (DMSO-d₆) δ 1.35 (s, 9H), 3.03 (t, J=5 Hz, 4H), 3.72 (t, J=5 Hz, 4H), 6.88 (d, J=8 Hz, 2H), 7.18 (d, J=6 Hz, 1H), 7.49 (d, J=8 Hz, 2H), 8.25 (d, J=6 Hz, 1H), 8.32 (s, 1H), 9.11 (s, 1H), 10.41 (s, 1H).

Example 61

This example as the trifluoroacetate salt was prepared as described in EXAMPLE 53C using 4-morpholin-4-ylmethylphenylamine in place of 9H-fluoren-2-ylamine. ¹H NMR (DMSO-d₆) δ 1.38 (s, 9H), 3.06 (m, 2H), 3.25 (m, 2H), 3.62 (m, 2H), 3.98 (m, 2H), 4.28 (s, 2H), 7.25 (d, J=6 Hz, 1H), 7.20 (d, J=8 Hz, 2H), 7.79 (d, J=8 Hz, 2H), 8.30 (s, 1H), 8.32 (d, J=6 Hz, 1H), 9.59 (s, 1H), 10.49 (s, 1H).

Example 62

This example as the trifluoroacetate salt was prepared as described in EXAMPLE 53C using 2-naphthylamine in place of 9H-fluoren-2-ylamine. ¹H NMR (DMSO-d₆) δ 1.31 (s, 9H), 7.23 (d, J=6 Hz, 1H), 7.39 (t, J=7 Hz, 1H), 7.45 (t, J=7 Hz, 1H), 7.75 (d, J=8 Hz, 1H), 7.83 (m, 3H), 8.28 (s, 1H), 8.38 (d, J=6 Hz, 1H), 9.63 (s, 1H), 10.55 (s, 1H).

Example 63

This example as the trifluoroacetate salt was prepared as described in EXAMPLE 53C using 5-aminobenzo[b]thiophene in place of 9H-fluoren-2-ylamine. ¹H NMR (DMSO-d₆) δ 1.32 (s, 9H), 7.20 (d, J=6 Hz, 1H), 7.38 (d, J=6 Hz, 1H), 7.58 (d, J=8 Hz, 1H), 7.75 (d, J=6 Hz, 1H), 7.92 (d, J=8 Hz, 1H), 8.23 (s, 1H), 8.28 (s, 1H), 8.32 (d, J=6 Hz, 1H), 9.55 (s, 1H), 10.53 (s, 1H).

Example 64

This example as the trifluoroacetate salt was prepared as described in EXAMPLE 53C using 5-amino-2,3-dihydrobenzofuran in place of 9H-fluoren-2-ylamine. ¹H NMR (DMSO-d₆) δ 1.38 (s, 9H), 3.26 (t, J=8 Hz, 2H), 4.50 (t, J=8 Hz, 2H), 6.73 (d, J=6 Hz, 1H), 7.20 (m, 1H), 7.28 (d, J=6 Hz, 1H), 7.42 (s, 1H), 8.22 (d, J=6 Hz, 1H), 8.32 (s, 1H), 9.32 (s, 1H), 10.54 (s, 1H).

Example 65

This example as the trifluoroacetate salt was prepared as described in EXAMPLE 53C using 5-aminobenzofuran in place of 9H-fluoren-2-ylamine. ¹H NMR (DMSO-d₆) δ 1.32 (s, 9H), 6.92 (s, 1H), 7.22 (d, J=6 Hz, 1H), 7.48 (d, J=6 Hz, 1H), 7.55 (d, J=6 Hz, 1H), 7.95 (s, 1H), 7.99 (s, 1H), 8.28 (m, 2H), 9.62 (s, 1H), 10.64 (s, 1H).

Example 66

This example as the trifluoroacetate salt was prepared as described in EXAMPLE 53C using 5-amino-1H-indole in place of 9H-fluoren-2-ylamine. ¹H NMR (DMSO-d₆) δ 1.32 (s, 9H), 6.41 (s, 1H), 7.20 (m, 2H), 7.38 (m, 2H), 7.75 (s, 1H), 8.21 (d, J=6 Hz, 1H), 8.35 (s, 1H), 9.45 (s, 1H), 10.64 (s, 1H), 11.05 (s, 1H).

Example 67

This example as the trifluoroacetate salt was prepared as described in EXAMPLE 53C using 5-amino-1H-indazole in place of 9H-fluoren-2-ylamine. ¹H NMR (DMSO-d₆) δ 1.28 (s, 9H), 7.15 (d, J=6 Hz, 1H), 7.26 (d, J=8 Hz, 1H), 7.65 (d, J=8 Hz, 1H), 7.93 (s, 1H), 8.03 (s, 1H), 8.24 (s, 1H), 8.33 (d, J=6 Hz, 1H), 9.55 (s, 1H), 10.64 (s, 1H), 12.78 (s, 1H).

Example 68

This example as the trifluoroacetate salt was prepared as described in EXAMPLE 53C using 5-amino-1-methyl-1H-indazole in place of 9H-fluoren-2-ylamine. ¹H NMR (DMSO-d₆) δ 1.28 (s, 9H), 4.05 (s, 3H), 7.25 (d, J=6 Hz, 1H), 7.52 (d, J=8 Hz, 1H), 7.65 (d, J=8 Hz, 1H), 7.99 (s, 1H), 8.05 (s, 1H), 8.28 (d, J=6 Hz, 1H), 8.31 (s, 1H), 9.60 (s, 1H), 10.60 (s, 1H).

Example 69

This example as the trifluoroacetate salt was prepared as described in EXAMPLE 53C using 4-pyrrol-1-ylphenylamine in place of 9H-fluoren-2-ylamine. ¹H NMR (DMSO-d₆) δ 1.38 (s, 9H), 6.22 (d, J=5 Hz, 2H), 7.23 (d, J=6 Hz, 1H), 7.28 (d, J=5 Hz, 2H), 7.48 (d, J=8 Hz, 2H), 7.78 (d, J=8 Hz, 2H), 8.28 (s, 1H), 8.33 (d, J=6 Hz, 1H), 9.49 (s, 1H), 10.48 (s, 1H).

Example 70

This example as the trifluoroacetate salt was prepared as described in EXAMPLE 53C using 4-pyrazol-1-ylphenylamine in place of 9H-fluoren-2-ylamine. ¹H NMR (DMSO-d₆) δ 1.36 (s, 9H), 6.62 (s, 1H), 7.35 (d, J=6 Hz, 1H), 7.72 (s, 1H), 7.75 (d, J=8 Hz, 1H), 7.80 (d, J=8 Hz, 2H), 8.28 (s, 1H), 8.33 (d, J=6 Hz, 2H), 8.39 (s, 1H), 9.58 (s, 1H), 10.48 (s, 1H).

Example 71

This example as the trifluoroacetate salt was prepared as described in EXAMPLE 53C using 4,6-dimethoxypyrimidin-2-ylphenylamine in place of 9H-fluoren-2-ylamine. ¹H NMR (DMSO-d₆) δ 1.39 (s, 9H), 4.00 (s, 6H), 7.28 (d, J=6 Hz, 1H), 7.83 (d, J=8 Hz, 2H), 8.35 (m, 5H), 9.71 (s, 1H), 10.45 (s, 1H).

Example 72

This example as the trifluoroacetate salt was prepared as described in EXAMPLE 53C using 1-acetyl-5-amino-2,3-dihydro-1H-indole in place of 9H-fluoren-2-ylamine. ¹H NMR (DMSO-d₆) δ 1.38 (s, 9H), 2.13 (s, 3H), 3.12 (t, J=9 Hz, 2H), 4.06 (t, J=9 Hz, 2H), 7.20 (d, J=7 Hz, 1H), 7.38 (d, J=7 Hz, 1H), 7.52 (s, 1H), 7.96 (d, J=7 Hz, 1H), 8.28 (m, 2H), 9.38 (s, 1H), 10.52 (s, 1H).

Example 73

This example as the trifluoroacetate salt was prepared as described in EXAMPLE 53C using 5-amino-2,3-dihydro-1H-indole in place of 9H-fluoren-2-ylamine. ¹H NMR (DMSO-d$_6$) δ 1.39 (s, 9H), 3.15 (t, J=9 Hz, 2H), 3.66 (t, J=9 Hz, 2H), 7.22 (d, J=7 Hz, 2H), 7.58 (d, J=7 Hz, 1H), 7.56 (s, 1H), 8.30 (d, J=7 Hz, 2H), 9.48 (s, 1H), 10.52 (s, 1H).

Example 74

This example as the trifluoroacetate salt was prepared as described in EXAMPLE 53C using 9H-carbazol-2-ylamine in place of 9H-fluoren-2-ylamine. $^1$H NMR (DMSO-d$_6$) δ 1.32 (s, 9H), 7.15 (t, J=8 Hz, 1H), 7.22 (m, 1H), 7.32 (t, J=8 Hz, 1H), 7.50 (m, 3H), 8.05 (d, J=8 Hz, 2H), 8.28 (m, 3H), 9.52 (s, 1H), 10.62 (s, 1H), 11.18 (s, 1H).

Example 75

This example as the trifluoroacetate salt was prepared as described in EXAMPLE 53C using 9-ethyl-9H-carbazol-2-ylamine in place of 9H-fluoren-2-ylamine. $^1$H NMR (DMSO-d$_6$) δ 1.30 (s, 9H), 1.32 (t, J=8 Hz, 3H), 4.43 (q, J=8 Hz, 2H), 7.17 (s, 1H), 7.18 (t, J=8 Hz, 1H), 7.45 (t, J=8 Hz, 1H), 7.48 (m, 3H), 8.08 (d, J=8 Hz, 1H), 8.23 (d, J=8 Hz, 1H), 9.30 (m, 2H), 9.58 (s, 1H), 10.65 (s, 1H).

Example 76

This example as the trifluoroacetate salt was prepared as described in EXAMPLE 53C using 5-aminobenzthiazole in place of 9H-fluoren-2-ylamine. $^1$H NMR (DMSO-d$_6$) δ 1.35 (s, 9H), 7.28 (d, J=6 Hz, 1H), 7.75 (d, J=8 Hz, 1H), 8.05 (d, J=8 Hz, 1H), 7.35 (m, 2H), 8.58 (s, 1H), 9.35 (s, 1H), 9.62 (s, 1H), 10.52 (s, 1H).

Example 77

To 2-amino-4-phenylthiazole (35 mg), in 1:1 THF/toluene (0.5 mL) was added 0.1 mL of 2M trimethylaluminum in hexane, and the mixture stirred at 55° C. for 2 hours. EXAMPLE 12C (40 mg) in tetrahydrofuran (0.5 mL) was added and the mixture stirred at 110° C. overnight. The mixture was cooled, quenched with water and the crude product purified as described in EXAMPLE 12D to give 4 mg of the title compound as the trifluoroacetate salt. $^1$H NMR (DMSO-d$_6$) δ 0.85 (s, 9H), 1.17 (d, J=8 Hz, 3H), 4.03 (m, 1H), 7.20 (d, J=7 Hz, 2H), 7.26 (s, 1H), 7.38 (m, 4H), 7.58 (br s, 1H), 7.82 (m, 1H), 8.54 (s, 1H), 11.39 (s, 1H).

Example 78

This example as the trifluoroacetate salt was prepared as described in EXAMPLE 77 using EXAMPLE 53B in place of EXAMPLE 12C. $^1$H NMR (DMSO-d$_6$) δ 1.38 (s, 9H), 7.20 (d, J=7 Hz, 2H), 7.27 (s, 1H), 7.38 (m, 4H), 7.68 (br s, 1H), 8.38 (s, 1H), 8.58 (d, J=6 Hz, 1H), 11.29 (s, 1H).

Example 79A

A mixture of 4-aminobiphenyl (1.7 g), EXAMPLE 12A (0.62 g) and concentrated hydrochloric acid (0.06 mL) was heated at 178° C. overnight. After cooling, the crude product was purified by flash chromatography on silica gel using ethyl acetate to provide 0.36 g of the title compound as a yellow solid. $^1$H NMR (DMSO-d$_6$) δ 5.87 (d, J=6 Hz, 1H), 6.55 (br s, 2H), 7.28 (m, 1H), 7.42 (t, J=7 Hz, 2H), 7.52 (d, J=8 Hz, 2H), 7.62 (d, J=8 Hz, 2H), 7.88 (m, 3H), 8.99 (s, 1H).

Example 79B

A mixture of EXAMPLE 79A (30 mg), EXAMPLE 6 (60 mg), sodium ethoxide (0.1 mL, 21% (w/w) in ethanol) and dimethylsulfoxide (1.2 mL) was heated at 155° C. overnight. After cooling, the mixture was purified as described in EXAMPLE 12D to give 15 mg of the title compound as the trifluoroacetate salt. $^1$H NMR (DMSO-d$_6$) δ 1.38 (s, 9H), 7.22 (d, J=6 Hz, 1H), 7.32 (m, 1H), 7.42 (t, J=8 Hz, 2H), 7.63 (m, 4H), 7.77 (d, J=8 Hz, 2H), 8.30 (s, 1H), 8.33 (d, J=6 Hz, 1H), 9.58 (s, 1H), 10.57 (s, 1H).

Example 80

This example as the trifluoroacetate salt was prepared as described in EXAMPLE 79B using EXAMPLE 11 in place of EXAMPLE 6. $^1$H NMR (DMSO-d$_6$) δ 7.00 (br s, 1H), 7.30 (m, 5H), 7.40 (t, J=8 Hz, 2H), 7.56 (m, 4H), 7.72 (d, J=8 Hz, 2H), 8.37 (d, J=6 Hz, 1H), 9.70 (s, 1H), 10.20 (br s, 1H), 10.96 (s, 1H).

Example 81

This example as the trifluoroacetate salt was prepared as described in EXAMPLE 79B using EXAMPLE 7 in place of EXAMPLE 6. $^1$H NMR (DMSO-d$_6$) δ 0.89 (s, 9H), 3.30 (m, 2H), 6.96 (br s, 1H), 7.34 (m, 1H), 7.42 (t, J=8 Hz, 2H), 7.66 (m, 6H), 8.20 (m, 1H), 8.29 (d, J=6 Hz, 1H), 9.67 (s, 1H), 10.82 (s, 1H).

Example 82

This example as the trifluoroacetate salt was prepared as described in EXAMPLE 79B using EXAMPLE 8 in place of EXAMPLE 6. $^1$H NMR (DMSO-d$_6$) δ 0.17 (m, 2H), 0.39 (m, 2H), 0.95 (m, 1H), 3.38 (m, 2H), 6.90 (m, 1H), 7.32 (m, 1H), 7.42 (t, J=8 Hz, 2H), 7.62 (m, 4H), 7.73 (d, J=8 Hz, 2H), 8.10 (m, 1H), 8.28 (d, J=6 Hz, 1H), 9.65 (s, 1H), 10.82 (s, 1H).

Example 83

This example as the trifluoroacetate salt was prepared as described in EXAMPLE 79B using EXAMPLE 9 in place of EXAMPLE 6. $^1$H NMR (DMSO-d$_6$) δ 3.10 (m, 2H), 3.32 (m, 2H), 3.42 (m, 2H), 3.70 (m, 2H), 3.93 (m, 4H), 6.78 (d, J=6 Hz, 1H), 7.36 (m, 1H), 7.42 (t, J=8 Hz, 2H), 7.62 (m, 4H), 7.75 (d, J=8 Hz, 2H), 7.98 (m, 1H), 8.28 (d, J=6 Hz, 1H), 9.61 (s, 1H), 11.02 (s, 1H).

Example 84

This example as the trifluoroacetate salt was prepared as described in EXAMPLE 79B using EXAMPLE 2 in place of EXAMPLE 6. $^1$H NMR (DMSO-d$_6$) δ 0.81 (d, J=7 Hz, 3H), 0.82 (d, J=7 Hz, 3H), 1.16 (d, J=7 Hz, 3H), 1.23 (m, 1H), 1.40 (m, 1H), 1.59 (m, 1H), 4.15 (m, 1H), 7.16 (m, 1H), 7.32 (m, 1H), 7.42 (t, J=8 Hz, 2H), 7.62 (m, 4H), 7.77 (d, J=8 Hz, 2H), 7.98 (d, J=10 Hz, 1H), 8.31 (d, J=6 Hz, 1H), 9.57 (s, 1H), 10.47 (s, 1H).

Example 85

This example as the trifluoroacetate salt was prepared as described in EXAMPLE 79B using EXAMPLE 1 in place of EXAMPLE 6. $^1$H NMR (DMSO-d$_6$) δ 0.81 (d, J=7 Hz, 3H), 0.82 (d, J=7 Hz, 3H), 1.16 (d, J=7 Hz, 3H), 1.69 (m, 1H), 3.96 (m, 1H), 7.30 (m, 2H), 7.42 (t, J=8 Hz, 2H), 7.62 (m, 4H), 7.77 (d, J=8 Hz, 2H), 7.99 (d, J=10 Hz, 1H), 8.33 (d, J=6 Hz, 1H), 9.58 (s, 1H), 10.42 (s, 1H).

Example 86

This example as the trifluoroacetate salt was prepared as described in EXAMPLE 79B using EXAMPLE 10 in place of EXAMPLE 6. $^1$H NMR (DMSO-d$_6$) δ 1.52 (d, J=8 Hz, 3H), 5.28 (m, 1H), 7.20 (m, 1H), 7.35 9M, 6H), 7.45 (t, J=8 Hz, 2H), 7.62 (m, 4H), 7.77 (d, J=8 Hz, 2H), 8.32 (d, J=6 Hz, 1H).

Example 87

This example as the trifluoroacetate salt was prepared as described in EXAMPLE 79B using EXAMPLE 4 in place of EXAMPLE 6. $^1$H NMR (DMSO-d$_6$) δ 0.88 (s, 9H), 1.35 (d, J=8 Hz, 3H), 3.99 (m, 1H), 7.30 (m, 1H), 7.39 (d, J=7 Hz, 1H), 7.42 (t, J=8 Hz, 2H), 7.62 (m, 4H), 7.79 (d, J=8 Hz, 2H), 8.00 (d, J=10 Hz, 1H), 8.35 (d, J=6 Hz, 1H), 9.57 (s, 1H), 10.32 (s, 1H).

Example 88

This example as the trifluoroacetate salt was prepared as described in EXAMPLE 79B using EXAMPLE 5 in place of EXAMPLE 6. $^1$H NMR (DMSO-d$_6$) δ 0.80 (t, J=7 Hz, 3H), 1.32 (s, 6H), 1.67 (q, J=7 Hz, 2H), 7.30 (m, 2H), 7.42 (t, J=8 Hz, 2H), 7.62 (m, 4H), 7.78 (d, J=8 Hz, 2H), 8.20 (s, 1H), 8.35 (d, J=6 Hz, 1H), 9.60 (s, 1H), 10.52 (s, 1H).

Example 89

This example was prepared as described in EXAMPLE 79A using 3,4,5-trimethoxyphenylamine in place of 4-aminobiphenyl. $^1$H NMR (DMSO-d$_6$) δ 3.61 (s, 3H), 3.77 (s, 6H), 5.87 (d, J=6 Hz, 1H), 6.50 (br s, 2H), 7.20 (s, 2H), 7.82 (d, J=6 Hz, 1H), 8.69 (s, 1H).

Example 90

To 3,5-dichloro-[1,2,4]thiadiazole (0.66 g) was added 0.5 M ammonia in dioxane (20 mL) at 0° C. and the mixture stirred at ambient temperature overnight. The mixture was concentrated, 4-aminobiphenyl (1.6 g) added and the mixture heated neat at 150° C. overnight. Purification as described in EXAMPLE 12D gave 56 mg of the title compound as the trifluoroacetate salt. $^1$H NMR (DMSO-d$_6$) δ 7.23 (m, 1H), 7.41 (m, 4H), 7.52 (t, J=8 Hz, 2H), 7.62 (m, 2H), 7.75 (d, J=8 Hz, 2H), 9.55 (s, 1H).

Example 91

A mixture of 9H-fluoren-2-ylamine (122 mg), 4-amino-2-chloro-5-fluoropyrimidine (54 mg) in n-butanol (1 mL) was heated at 120° C. overnight. The mixture was concentrated and the residue purified as described in EXAMPLE 12D to give 98 mg of the title compound as the trifluoroacetate salt. $^1$H NMR (DMSO-d$_6$) δ 3.90 (s, 2H), 7.30 (t, J=7 Hz, 1H), 7.39 (t, J=7 Hz, 1H), 7.58 (m, 2H), 7.82 (m, 3H), 8.10 (d, J=4 Hz, 1H), 8.20 (br s, 2H), 9.82 (s, 1H).

Example 92

A mixture of 4-iodophenylamine (660 mg), 4-amino-2-chloropyrimidine (400 mg) in n-butanol (4 mL) was heated at 115° C. overnight. The mixture was concentrated and the residue purified by flash chromatography on silica gel using 5:1 ethyl acetate/hexane followed by 5:1:0.01 ethyl acetate/hexane/triethylamine to provide 0.43 g of the title compound as a solid. $^1$H NMR (DMSO-d$_6$) δ 5.92 (d, J=6 Hz, 1H), 6.55 (br s, 2H), 7.50 (d, J=8 Hz, 2H), 7.63 (d, J=8 Hz, 2H), 7.82 (d, J=6 Hz, 1H), 9.00 (s, 1H).

Example 93

N-(3,4,5-trimethoxyphenyl)-(1,3,5)triazine-2,4-diamine

This compound was purchased from Ryan Scientific, Inc. (U.S.A.)

Example 94

A mixture of 2-chloro-5-cyano-6-amino pyrimidine (0.1 g), 3,4,5-trimethoxy aniline (0.71 mmol), palladium(II) acetate (1 mol %), 9,9-dimethyl-4,5-bis(diphenylphosphino) xanthene (1.5 mol %) and cesium carbonate (1.29 mmol) in dioxane (2 mL) was heated in a microwave at 150° C. for 20 minutes, cooled, filtered through diatomaceous earth (Celite®) and concentrated. The concentrate was purified by HPLC on a C18 column with acetonitrile/water/0.1% trifluoroacetic acid. $^1$H NMR (DMSO-d$_6$) δ 9.35 (br s, 1H), 8.15 (s, 1H), 6.45 (s, 2H), 5.5 (s, 2H), 3.73 (s, 6H), 3.70 (s, 3H).

Example 95

(R)-3-(4-(3,4,5-trimethoxyphenylamino)-(1,3,5)triazin-2-ylamino)-4-(1,2,2-trimethylpropylamino) cyclobut-3-ene-1,2-dione This example as the trifluoroacetate salt was prepared as described in EXAMPLE 79B using EXAMPLE 3 in place of EXAMPLE 6 and EXAMPLE 93 in place of EXAMPLE 79A. $^1$H NMR (DMSO-d$_6$) δ 0.87 (s, 9H), 1.19 (d, J=8 Hz, 3H), 3.62 (s, 3H), 3.79 (s, 6H), 4.08 (m, 1H), 7.10 (s, 2H), 8.08 (s, 1H), 8.63 (s, 1H), 10.04 (s, 1H), 11.22 (s, 1H).

Example 96

This example as the trifluoroacetate salt was prepared as described in EXAMPLE 79B using EXAMPLE 10 in place of EXAMPLE 6 and EXAMPLE 94 in place of EXAMPLE 79A. $^1$H NMR (DMSO-d$_6$) δ 1.30 (m, 3H), 3.61 (s, 3H), 3.64 (s, 6H), 5.22 (m, 1H), 7.02 (s, 2H), 7.23 (m, 1H), 7.30 (m, 4H), 8.06 (d, J=10 Hz, 1H), 8.63 (s, 1H), 10.00 (s, 1H), 11.21 (s, 1H).

Example 97

This example as the trifluoroacetate salt was prepared as described in EXAMPLE 79B using EXAMPLE 4 in place of EXAMPLE 6 and EXAMPLE 94 in place of EXAMPLE 79A. $^1$H NMR (DMSO-d$_6$) δ 0.85 (s, 9H), 1.09 (d, J=8 Hz, 3H), 3.60 (s, 3H), 3.64 (s, 6H), 3.98 (m, 1H), 7.01 (s, 2H), 7.72 (d, J=10 Hz, 1H), 8.64 (s, 1H), 9.98 (s, 1H), 10.55 (s, 1H).

Example 98

This example as the trifluoroacetate salt was prepared as described in EXAMPLE 79B using EXAMPLE 1 in place of EXAMPLE 6 and EXAMPLE 94 in place of EXAMPLE 79A. $^1$H NMR (DMSO-d$_6$) δ 0.80 (m, 6H), 0.98 (m, 3H), 1.60 (m, 1H), 3.60 (s, 3H), 3.64 (s, 6H), 3.92 (m, 1H), 7.00 (s, 2H), 7.63 (d, J=10 Hz, 1H), 8.63 (s, 1H), 9.98 (s, 1H), 10.80 (s, 1H).

Example 99

This example as the trifluoroacetate salt was prepared as described in EXAMPLE 79B using EXAMPLE 91 in place of EXAMPLE 79A. ¹H NMR (DMSO-d₆) δ 1.30 (s, 9H), 3.82 (s, 2H), 7.22 (t, J=7 Hz, 1H), 7.32 (t, J=7 Hz, 1H), 7.53 (d, J=7 Hz, 1H), 7.61 (d, J=7 Hz, 1H), 7.71 (m, 2H), 7.84 (s, 1H), 8.01 (s, 1H), 8.39 (s, 1H), 9.52 (s, 1H), 10.78 (s, 1H).

Example 100

This example as the trifluoroacetate salt was prepared as described in EXAMPLE 79B using EXAMPLE 3 in place of EXAMPLE 6 and EXAMPLE 90 in place of EXAMPLE 79A. ¹H NMR (DMSO-d₆) δ 0.88 (s, 9H), 1.21 (d, J=8 Hz, 3H), 4.02 (m, 1H), 7.31 (m, 1H), 7.42 (t, J=8 Hz, 2H), 7.62 (m, 4H), 7.71 (d, J=8 Hz, 2H), 7.91 (d, J=10 Hz, 1H), 9.77 (s, 1H), 11.82 (s, 1H).

Example 101

This example as the trifluoroacetate salt was prepared as described in EXAMPLE 79B using EXAMPLE 4 in place of EXAMPLE 6 and EXAMPLE 90 in place of EXAMPLE 79A. ¹H NMR (DMSO-d₆) δ 0.88 (s, 9H), 1.21 (d, J=8 Hz, 3H), 4.02 (m, 1H), 7.31 (m, 1H), 7.42 (t, J=8 Hz, 2H), 7.62 (m, 4H), 7.71 (d, J=8 Hz, 2H), 7.91 (d, J=10 Hz, 1H), 9.77 (s, 1H), 11.82 (s, 1H).

Example 102

This example as the trifluoroacetate salt was prepared as described in EXAMPLE 79B using EXAMPLE 92 in place of EXAMPLE 79A. ¹H NMR (DMSO-d₆) δ 1.37 (s, 9H), 7.22 (d, J=6 Hz, 1H), 7.52 (t, J=8 Hz, 2H), 7.61 (d, J=8 Hz, 2H), 8.23 (s, 1H), 8.31 (d, J=6 Hz, 1H), 9.55 (s, 1H), 10.47 (s, 1H).

Example 103

A mixture of EXAMPLE 102 (14 mg), pyridine-4-boronic acid (5 mg), tetrakis(triphenylphosphine)palladium(0) (5 mg), potassium carbonate (26 mg), ethanol (1 mL), benzene (1 mL) and water (100 μL) was heated to reflux for 2 hours. The mixture was cooled and concentrated and the residue purified as described in EXAMPLE 12D to give 2.1 mg of the title compound as the trifluoroacetate salt. ¹H NMR (DMSO-d₆) δ 1.38 (s, 9H), 7.31 (d, J=6 Hz, 1H), 7.96 (d, J=8 Hz, 2H), 8.03 (d, J=8 Hz, 2H), 8.25 (d, J=6 Hz, 2H), 8.27 (s, 1H), 8.40 (d, J=6 Hz, 1H), 8.82 (d, J=6 Hz, 2H), 9.89 (s, 1H), 10.56 (s, 1H).

Example 104

This example as the trifluoroacetate salt was prepared as described in EXAMPLE 103 using pyridine-3-boronic acid in place of pyridine-4-boronic acid. ¹H NMR (DMSO-d₆) δ 1.38 (s, 9H), 7.25 (d, J=6 Hz, 1H), 7.65 (m, 1H), 7.72 (d, J=8 Hz, 2H), 7.86 (d, J=8 Hz, 2H), 8.28 (m, 2H), 8.35 (d, J=6 Hz, 1H), 8.62 (d, J=6 Hz, 1H), 8.98 (s, 1H), 9.62 (s, 1H), 10.52 (s, 1H).

Example 105

This example as the trifluoroacetate salt was prepared as described in EXAMPLE 103 using 1H-pyrazole-4-boronic acid in place of pyridine-4-boronic acid. ¹H NMR (DMSO-d₆) δ 1.36 (s, 9H), 7.12 (d, J=6 Hz, 1H), 7.53 (d, J=8 Hz, 2H), 7.68 (d, J=8 Hz, 2H), 7.98 (s, 2H), 8.28 (m, 2H), 9.48 (s, 1H), 10.56 (s, 1H).

Example 106

This example as the trifluoroacetate salt was prepared as described in EXAMPLE 103 using pyrimidine-5-boronic acid in place of pyridine-4-boronic acid. ¹H NMR (DMSO-d₆) δ 1.39 (s, 9H), 7.29 (d, J=6 Hz, 1H), 7.78 (d, J=8 Hz, 2H), 7.88 (d, J=8 Hz, 2H), 8.32 (s, 1H), 8.35 (d, J=6 Hz, 1H), 9.13 (m, 2H), 9.65 (s, 1H), 10.56 (s, 1H).

Example 107

This example as the trifluoroacetate salt was prepared as described in EXAMPLE 103 using 2,4-dimethoxypyrimidine-5-boronic acid in place of pyridine-4-boronic acid. ¹H NMR (DMSO-d₆) δ 1.39 (s, 9H), 3.93 (s, 3H), 3.93 (s, 3H), 7.23 (d, J=6 Hz, 1H), 7.50 (d, J=8 Hz, 2H), 7.73 (d, J=8 Hz, 2H), 8.32 (s, 1H), 8.35 (d, J=6 Hz, 1H), 8.37 (s, 1H), 9.56 (s, 1H), 10.49 (s, 1H).

Example 108

This example as the trifluoroacetate salt was prepared as described in EXAMPLE 103 using 2-methoxypyrimidine-5-boronic acid in place of pyridine-4-boronic acid. ¹H NMR (DMSO-d₆) δ 1.39 (s, 9H), 3.93 (s, 3H), 7.25 (d, J=6 Hz, 1H), 7.46 (d, J=8 Hz, 2H), 7.63 (d, J=8 Hz, 2H), 8.30 (s, 1H), 8.35 (d, J=6 Hz, 1H), 8.91 (s, 2H), 9.56 (s, 1H), 10.49 (s, 1H).

Example 109

A mixture of 4-amino-2-chloro-5-fluoropyrimidine (147 mg), EXAMPLE 6 (280 mg), sodium ethoxide (0.38 mL, 21% (w/w) in ethanol) and dimethylsulfoxide (4 mL) was heated at 75° C. overnight. After cooling, the mixture was purified by flash chromatography on silica gel using ethyl acetate to provide 0.126 g of the title compound as a solid. ¹H NMR (DMSO-d₆) δ 1.42 (s, 9H), 8.20 (s, 1H), 8.53 (s, 1H), 11.52 (s, 1H).

Example 110

A mixture of 4-[1,2,3]thiadiazol-4-ylphenylamine (10.7 mg), EXAMPLE 109 (14.8 mg) and n-butanol (0.6 mL) was heated at 110° C. overnight. The mixture was cooled and concentrated and the residue purified as described in EXAMPLE 12D to give 3 mg of the title compound as the trifluoroacetate salt. ¹H NMR (DMSO-d₆) δ 1.31 (s, 9H), 7.81 (s, 1H), 7.82 (d, J=8 Hz, 2H), 8.01 (d, J=8 Hz, 2H), 8.40 (s, 1H), 9.45 (s, 1H), 9.66 (s, 1H), 10.80 (s, 1H).

Example 111A

To EXAMPLE 6 (4.9 g) was slowly added 7N ammonia in methanol (120 mL) and the mixture stirred at ambient temperature overnight. The solid was filtered, washed with ether, and dried. ¹H NMR (DMSO-d₆) δ 1.38 (s, 9H), 7.52 (s, 1H).

Example 111B

A mixture of EXAMPLE 111A (1.85 g), 2,4-dichloropyrimidine (1.64 g), 60% oily sodium hydride (0.88 g) and N,N'-dimethylformamide (50 mL) was stirred at ambient temperature for 3 hours. The mixture was quenched with saturated ammonium chloride and concentrated. The residue was dissolved in 1:2 methanol/chloroform and the insoluble solid removed. The filtrate was concentrated and the resulting solid again dissolved in 1:2 methanol/chloroform and the insoluble product removed. The filtrate was concentrated and the residue purified by flash chromatography on silica gel using 100:100:0.5 to 100:100:2 chloroform/dichloromethane/methanol to provide 0.7 g of the title compound as a solid. $^1$H NMR (DMSO-d$_6$) δ 1.42 (s, 9H), 7.47 (s, 1H), 8.47 (d, J=7 Hz, 1H), 8.56 (m, 1H), 11.28 (br s, 1H).

Example 111 Alternate

EXAMPLE 111 was also prepared by the following alternate procedure:

To a cooled solution of 3,4-diethoxycyclobut-3-ene-1,2-dione (3.07 g) and sodium hydride (60% in mineral oil, 0.57 g) in 100 mL tetrahydrofuran was added 4-amino-2-chloropyrimidine (1.84 g) and the mixture stirred at 0° C. for 1 hour and at ambient temperature for 3 days. The mixture was concentrated, water added and the solution washed with 1:9 ethyl acetate/hexane. To the aqueous mixture was added tert-butylamine (1.06 g) in 10 mL cold water and the mixture stirred at ambient temperature overnight. The precipitate was filtered, washed with water and dried.

Example 112

A mixture of 4-[1,2,4]triazol-1-ylphenylamine (24 mg), EXAMPLE 111 (21 mg), trifluoroacetic acid (0.06 mL) and 2,2,2-trifluoroethanol (0.6 mL) was heated at 75° C. overnight. The mixture was concentrated and the residue purified as described in EXAMPLE 12D to give 22 mg of the title compound as the trifluoroacetate salt. $^1$H NMR (DMSO-d$_6$) δ 1.38 (s, 9H), 7.29 (d, J=6 Hz, 1H), 7.77 (t, J=8 Hz, 2H), 7.84 (d, J=8 Hz, 2H), 8.20 (s, 1H), 8.30 (br s, 1H), 8.37 (d, J=6 Hz, 1H), 9.18 (s, 1H), 9.69 (s, 1H), 10.52 (s, 1H).

Example 113

This example as the trifluoroacetate salt was prepared as described in EXAMPLE 112 using cyclohexylamine in place of 4-[1,2,4]triazol-1-ylphenylamine. $^1$H NMR (DMSO-d$_6$) δ 1.19 (m, 1H), 1.29 (m, 4H), 1.42 (s, 9H), 1.60 (m, 1H), 1.72 (m, 2H), 1.87 (m, 2H), 3.80 (m, 1H), 7.10 (m, 1H), 8.17 (d, J=6 Hz, 1H), 8.39 (br s, 1H), 10.82 (br s, 1H).

Example 114

This example as the trifluoroacetate salt was prepared as described in EXAMPLE 112 using 4-(pyrazol-3-yl)phenylamine in place of 4-[1,2,4]triazol-1-ylphenylamine. $^1$H NMR (DMSO-d$_6$) δ 1.36 (s, 9H), 6.66 (s, 1H), 7.80 (m, 1H), 7.69 (m, 3H), 7.76 (d, J=8 Hz, 2H), 8.28 (s, 1H), 8.33 (d, J=6 Hz, 2H), 9.82 (s, 1H), 10.68 (s, 1H).

Example 115

This example as the trifluoroacetate salt was prepared as described in EXAMPLE 112 using 5-aminobenzotriazole in place of 4-[1,2,4]triazol-1-ylphenylamine. $^1$H NMR (DMSO-d$_6$) δ 1.35 (s, 9H), 7.25 (d, J=6 Hz, 1H), 7.55 (d, J=8 Hz, 1H), 7.88 (d, J=8 Hz, 1H), 8.26 (s, 1H), 8.32 (s, 1H), 8.36 (d, J=6 Hz, 1H), 9.70 (s, 1H), 10.58 (s, 1H).

Example 116

This example as the trifluoroacetate salt was prepared as described in EXAMPLE 112 using 4-thiophen-3-ylphenylamine in place of 4-[1,2,4]triazol-1-ylphenylamine. $^1$H NMR (DMSO-d$_6$) δ 1.38 (s, 9H), 7.21 (d, J=6 Hz, 1H), 7.52 (d, J=6 Hz, 1H), 7.62 (m, 1H), 7.67 (d, J=8 Hz, 2H), 7.76 (d, J=8 Hz, 2H), 7.77 (s, 1H), 8.30 (s, 1H), 8.33 (d, J=6 Hz, 1H), 9.42 (s, 1H), 10.43 (s, 1H).

Example 117

This example as the trifluoroacetate salt was prepared as described in EXAMPLE 112 using 5-aminobenzimidazole in place of 4-[1,2,4]triazol-1-ylphenylamine. $^1$H NMR (DMSO-d$_6$) δ 1.34 (s, 9H), 7.22 (d, J=6 Hz, 1H), 7.76 (m, 2H), 8.23 (s, 1H), 8.36 (s, 1H), 8.37 (d, J=6 Hz, 1H), 9.38 (s, 1H), 9.78 (s, 1H), 10.60 (s, 1H).

Example 118

This example as the trifluoroacetate salt was prepared as described in EXAMPLE 112 using 1-acetyl-2,3-dihydro-1H-indol-6-ylamine in place of 4-[1,2,4]triazol-1-ylphenylamine. $^1$H NMR (DMSO-d$_6$) δ 1.34 (s, 9H), 2.13 (s, 3H), 3.09 (t, J=7 Hz, 2H), 4.09 (t, J=7 Hz, 2H), 7.13 (m, 2H), 7.32 (d, J=6 Hz, 1H), 8.23 (m, 3H), 9.53 (s, 1H), 10.62 (s, 1H).

Example 119

This example as the trifluoroacetate salt was prepared as described in EXAMPLE 112 using N-(3-aminophenyl)methanesulfonamide in place of 4-[1,2,4]triazol-1-ylphenylamine. $^1$H NMR (DMSO-d$_6$) δ 1.34 (s, 9H), 2.99 (s, 3H), 6.82 (d, J=6 Hz, 1H), 7.15 (m, 1H), 7.22 (t, J=6 Hz, 1H), 7.42 (m, 2H), 8.23 (s, 1H), 8.25 (d, J=6 Hz, 1H), 9.53 (s, 1H), 9.73 (s, 1H), 10.60 (s, 1H).

Example 120

This example as the trifluoroacetate salt was prepared as described in EXAMPLE 112 using 5-amino-2-trifluoromethylbenzimidazole in place of 4-[1,2,4]triazol-1-ylphenylamine. $^1$H NMR (DMSO-d$_6$) δ 1.34 (s, 9H), 7.22 (m, 1H), 7.50 (d, J=8 Hz, 1H), 7.63 (d, J=8 Hz, 1H), 8.17 (s, 1H), 8.23 (s, 1H), 8.34 (d, J=6 Hz, 1H), 9.72 (s, 1H), 10.62 (s, 1H).

Example 121

This example as the trifluoroacetate salt was prepared as described in EXAMPLE 112 using N-(4-aminophenyl)-4-methylbenzenesulfonamide in place of 4-[1,2,4]triazol-1-ylphenylamine. $^1$H NMR (DMSO-d$_6$) δ 1.34 (s, 9H), 2.37 (s, 3H), 7.00 (d, J=8 Hz, 2H), 7.21 (m, 1H), 7.37 (t, J=8 Hz, 2H), 7.50 (t, J=8 Hz, 2H), 7.61 (t, J=8 Hz, 2H), 8.23 (m, 2H), 9.39 (s, 1H), 9.99 (s, 1H), 10.41 (s, 1H).

Example 122

This example as the trifluoroacetate salt was prepared as described in EXAMPLE 112 using 5-amino-2-methylbenzthiazole in place of 4-[1,2,4]triazol-1-ylphenylamine. $^1$H NMR (DMSO-d$_6$) δ 1.35 (s, 9H), 2.79 (s, 3H), 7.30 (m, 1H), 7.61 (d, J=8 Hz, 1H), 7.91 (d, J=8 Hz, 1H), 8.27 (m, 2H), 8.29 (s, 1H), 9.72 (s, 1H), 10.58 (s, 1H).

Example 123

This example as the trifluoroacetate salt was prepared as described in EXAMPLE 112 using 4-(morpholine-4-sulfonyl)phenylamine in place of 4-[1,2,4]triazol-1-ylphenylamine. $^1$H NMR (DMSO-d$_6$) δ 1.39 (s, 9H), 2.82 (m, 4H), 3.62 (m, 4H), 7.32 (m, 1H), 7.62 (d, J=8 Hz, 2H), 7.97 (d, J=8 Hz, 2H), 8.27 (s, 1H), 8.40 (d, J=6 Hz, 1H), 9.96 (s, 1H), 10.57 (s, 1H).

Example 124

This example as the trifluoroacetate salt was prepared as described in EXAMPLE 112 using 3-(morpholine-4-sulfonyl)phenylamine in place of 4-[1,2,4]triazol-1-ylphenylamine. $^1$H NMR (DMSO-d$_6$) δ 1.39 (s, 9H), 2.84 (m, 4H), 3.63 (m, 4H), 7.28 (m, 1H), 7.30 (d, J=7 Hz, 1H), 7.59 (t, J=7 Hz, 1H), 7.99 (s, 1H), 8.19 (d, J=6 Hz, 1H), 8.27 (s, 1H), 8.38 (d, J=6 Hz, 1H), 9.72 (s, 1H), 10.56 (s, 1H).

Example 125

This example as the trifluoroacetate salt was prepared as described in EXAMPLE 112 using 5-amino-2-methylbenzimidazole in place of 4-[1,2,4]triazol-1-ylphenylamine. $^1$H NMR (DMSO-d$_6$) δ 1.38 (s, 9H), 2.78 (s, 3H), 7.22 (d, J=6 Hz, 1H), 7.70 (m, 2H), 8.24 (m, 2H), 8.38 (d, J=6 Hz, 1H), 9.70 (s, 1H), 10.58 (s, 1H), 14.42 (bs, 1H).

Example 126

This example as the trifluoroacetate salt was prepared as described in EXAMPLE 112 using 1-(toluene-4-sulfonyl)-1H-indol-5-ylamine in place of 4-[1,2,4]triazol-1-ylphenylamine. $^1$H NMR (DMSO-d$_6$) δ 1.21 (s, 9H), 2.32 (s, 3H), 6.78 (d, J=6 Hz, 1H), 7.10 (d, J=6 Hz, 1H), 7.38 (d, J=8 Hz, 2H), 7.47 (d, J=8 Hz, 1H), 7.72 (d, J=6 Hz, 1H), 7.84 (m, 3H), 7.91 (s, 1H), 8.17 (s, 1H), 8.27 (d, J=8 Hz, 1H), 9.39 (s, 1H), 10.50 (s, 1H).

Example 127

This example as the trifluoroacetate salt was prepared as described in EXAMPLE 112 using 1-methanesulfonyl-2,3-dihydro-1H-indol-5-ylamine in place of 4-[1,2,4]triazol-1-ylphenylamine. $^1$H NMR (DMSO-d$_6$) δ 1.38 (s, 9H), 2.92 (s, 3H), 3.08 (t, J=8 Hz, 2H), 3.92 (t, J=8 Hz, 2H), 7.18 (m, 2H), 7.42 (d, J=8 Hz, 1H), 7.57 (s, 1H), 8.28 (m, 2H), 9.36 (s, 1H), 10.49 (s, 1H).

Example 128

This example as the trifluoroacetate salt was prepared as described in EXAMPLE 112 using 4-pyridin-2-ylphenylamine in place of 4-[1,2,4]triazol-1-ylphenylamine. $^1$H NMR (DMSO-d$_6$) δ 1.32 (s, 9H), 7.20 (d, J=6 Hz, 1H), 7.38 (t, J=6 Hz, 1H), 7.42 (t, J=6 Hz, 1H), 7.58 (d, J=8 Hz, 1H), 7.83 (d, J=8 Hz, 1H), 7.92 (m, 2H), 8.26 (d, J=8 Hz, 2H), 8.32 (d, J=6 Hz, 1H), 8.65 (d, J=6 Hz, 1H), 9.55 (s, 1H), 10.58 (s, 1H).

Example 129

This example as the trifluoroacetate salt was prepared as described in EXAMPLE 112 using 4-(4-methanesulfonylpiperazin-1-yl)phenylamine in place of 4-[1,2,4]triazol-1-ylphenylamine. $^1$H NMR (DMSO-d$_6$) δ 1.36 (s, 9H), 2.92 (s, 3H), 3.18 (t, J=6 Hz, 4H), 3.26 (t, J=6 Hz, 4H), 6.95 (d, J=8 Hz, 2H), 7.25 (d, J=6 Hz, 1H), 7.48 (d, J=8 Hz, 2H), 8.23 (d, J=6 Hz, 1H), 8.28 (s, 1H), 9.28 (s, 1H), 10.52 (s, 1H).

Example 130

This example was prepared as described in EXAMPLE 112 using 7-amino-4H-benzo[1,4]oxazin-3-one in place of 4-[1,2,4]triazol-1-ylphenylamine. Instead of HPLC purification, crude material was washed with methanol and dried. $^1$H NMR (DMSO-d$_6$) δ 1.33 (s, 9H), 4.50 (s, 2H), 6.90 (d, J=8 Hz, 1H), 7.08 (d, J=8 Hz, 1H), 7.25 (d, J=6 Hz, 1H), 7.48 (s, 1H), 8.26 (d, J=6 Hz, 1H), 8.50 (s, 1H), 9.75 (s, 1H), 10.68 (s, 1H), 10.98 (s, 1H).

Example 131

This example as the trifluoroacetate salt was prepared as described in EXAMPLE 112 using 3-pyrrol-1-ylphenylamine in place of 4-[1,2,4]triazol-1-ylphenylamine. $^1$H NMR (DMSO-d$_6$) δ 1.36 (s, 9H), 6.25 (s, 2H), 7.15 (d, J=8 Hz, 1H), 7.22 (d, J=6 Hz, 1H), 7.26 (s, 2H), 7.38 (t, J=8 Hz, 1H), 7.58 (d, J=8 Hz, 1H), 7.82 (s, 1H), 8.28 (s, 1H), 8.34 (d, J=6 Hz, 1H), 9.55 (s, 1H), 10.52 (s, 1H).

Example 132

This example as the trifluoroacetate salt was prepared as described in EXAMPLE 112 using 6-amino-2-methylbenzthiazole in place of 4-[1,2,4]triazol-1-ylphenylamine. $^1$H NMR (DMSO-d$_6$) δ 1.37 (s, 9H), 2.78 (s, 3H), 7.26 (d, J=6 Hz, 1H), 7.66 (d, J=8 Hz, 1H), 7.81 (d, J=8 Hz, 1H), 8.28 (s, 1H), 8.33 (d, J=6 Hz, 1H), 8.46 (s, 1H), 9.62 (s, 1H), 10.48 (s, 1H).

Example 133

This example as the trifluoroacetate salt was prepared as described in EXAMPLE 112 using 4-oxazol-5-ylphenylamine in place of 4-[1,2,4]triazol-1-ylphenylamine. $^1$H NMR (DMSO-d$_6$) δ 1.38 (s, 9H), 7.26 (d, J=6 Hz, 1H), 7.35 (s, 1H), 7.65 (d, J=8 Hz, 2H), 7.81 (d, J=8 Hz, 2H), 8.25 (s, 1H), 8.34 (d, J=6 Hz, 1H), 8.38 (s, 1H), 9.59 (s, 1H), 10.46 (s, 1H).

Example 134

This example as the trifluoroacetate salt was prepared as described in EXAMPLE 112 using 4-aminopyridine in place of 4-[1,2,4]triazol-1-ylphenylamine. $^1$H NMR (DMSO-d$_6$) δ 1.42 (s, 9H), 7.00 (d, J=8 Hz, 2H), 7.55 (br.s, 1H), 8.18 (s, 1H), 8.71 (d, J=6 Hz, 1H), 8.95 (s, 2H), 9.25 (d, J=8 Hz, 2H), 11.08 (s, 1H).

Example 135

This example as the trifluoroacetate salt was prepared as described in EXAMPLE 112 using 4-(dimethylaminomethyl)phenylamine in place of 4-[1,2,4]triazol-1-ylphenylamine. $^1$H NMR (DMSO-d$_6$) δ 1.39 (s, 9H), 2.73 (s, 6H), 4.20 (s, 2H), 7.23 (d, J=6 Hz, 1H), 7.39 (d, J=8 Hz, 2H), 7.78 (d, J=8 Hz, 2H), 8.25 (s, 1H), 8.33 (d, J=6 Hz, 1H), 9.58 (s, 1H), 10.48 (s, 1H).

Example 136

This example as the trifluoroacetate salt was prepared as described in EXAMPLE 112 using 5-amino-2-methylisoindole-1,3-dione in place of 4-[1,2,4]triazol-1-ylphenylamine. $^1$H NMR (DMSO-d$_6$) δ 1.40 (s, 9H), 3.02 (s, 3H), 7.38 (d, J=6 Hz, 1H), 7.78 (d, J=8 Hz, 1H), 8.10 (d, J=8 Hz, 1H), 8.23 (s, 1H), 8.30 (s, 1H), 8.42 (d, J=6 Hz, 1H), 10.08 (s, 1H), 10.53 (s, 1H).

Example 137

A mixture of EXAMPLE 111A (168 mg), 4,6-dichloropyrimidine (157 g), 60% oily sodium hydride (0.80 g) and N,N'-dimethylformamide (7 mL) was stirred at ambient temperature for 4 hours. The mixture was quenched with ice and the mixture concentrated. The residue was purified by flash chromatography on silica gel using 100:100:1 chloroform/ dichloromethane/methanol to provide 160 mg of the title compound as a solid. $^1$H NMR (DMSO-d$_6$) δ 1.42 (s, 9H), 7.78 (s, 1H), 8.69 (s, 1H), 8.78 (br s, 1H), 11.10 (s, 1H).

Example 138

This example as the trifluoroacetate salt was prepared as described in EXAMPLE 112 using 4-iodoaniline in place of 4-[1,2,4]triazol-1-ylphenylamine and EXAMPLE 137 in place of EXAMPLE 111B. $^1$H NMR (DMSO-d$_6$) δ 1.42 (s, 9H), 6.71 (s, 1H), 7.47 (t, J=8 Hz, 2H), 7.62 (d, J=8 Hz, 2H), 8.40 (s, 1H), 9.48 (s, 1H), 9.80 (s, 1H), 10.82 (s, 1H).

Example 139

This example was prepared as described in EXAMPLE 111-2 using cyclopropylamine in place of tert-butylamine. MS (ESI): m/z 265 (M+H)$^+$.

Example 140

3-(2-chloropyrimidin-4-ylamino)-4-cyclobutylaminocyclobut-3-ene-1,2-dione

This example was prepared as described in EXAMPLE 111-2 using cyclobutylamine in place of tert-butylamine.

Example 141

This example as the trifluoroacetate salt was prepared as described in EXAMPLE 112 using 4-iodoaniline in place of 4-[1,2,4]triazol-1-ylphenylamine and EXAMPLE 139 in place of EXAMPLE 111. $^1$H NMR (DMSO-d$_6$) δ 0.49 (m, 2H), 0.65 (m, 2H), 2.98 (m, 1H), 6.88 (d, J=6 Hz, 1H), 7.48 (d, J=8 Hz, 2H), 7.61 (d, J=8 Hz, 2H), 6.89 (d, J=6 Hz, 1H), 8.25 (d, J=6 Hz, 1H), 9.58 (s, 1H), 10.60 (s, 1H).

Example 142

This example as the trifluoroacetate salt was prepared as described in EXAMPLE 112 using 4-iodoaniline in place of 4-[1,2,4]triazol-1-ylphenylamine and EXAMPLE 140 in place of EXAMPLE 111. $^1$H NMR (DMSO-d$_6$) δ 1.59 (m, 2H), 1.90 (m, 2H), 2.18 (m, 2H), 4.42 (m, 1H), 6.95 (d, J=6 Hz, 1H), 7.48 (d, J=8 Hz, 2H), 7.61 (d, J=8 Hz, 2H), 8.08 (d, J=6 Hz, 1H), 8.28 (d, J=6 Hz, 1H), 9.55 (s, 1H), 10.60 (s, 1H).

Example 143

This example as the trifluoroacetate salt was prepared as described in EXAMPLE 112 using 4-pyridin-4-ylphenylamine in place of 4-[1,2,4]triazol-1-ylphenylamine and EXAMPLE 140 in place of EXAMPLE 111. $^1$H NMR (DMSO-d$_6$) δ 1.55 (m, 2H), 1.85 (m, 2H), 2.38 (m, 2H), 4.55 (m, 1H), 7.01 (d, J=6 Hz, 1H), 7.82 (d, J=8 Hz, 2H), 7.92 (d, J=8 Hz, 2H), 8.30 (d, J=6 Hz, 1H), 8.33 (d, J=6 Hz, 2H), 8.46 (d, J=6 Hz, 1H), 8.75 (d, J=6 Hz, 1H), 9.82 (s, 1H), 10.63 (s, 1H).

Example 144

This example as the trifluoroacetate salt was prepared as described in EXAMPLE 103 using 4-(N,N-dimethylaminocarbonyl)phenylboronic acid in place of pyridine-4-boronic acid. $^1$H NMR (DMSO-d$_6$) δ 1.38 (s, 9H), 2.98 (s, 6H), 7.23 (d, J=6 Hz, 1H), 7.48 (d, J=8 Hz, 2H), 7.66 (m, 4H), 7.82 (d, J=8 Hz, 2H), 8.29 (s, 1H), 8.33 (d, J=6 Hz, 1H), 9.60 (s, 1H), 10.53 (s, 1H).

Example 145A

This example was prepared as described in EXAMPLE 111-2 using 4-amino-2-chloro-6-methylpyrimidine in place of 4-amino-2-chloropyrimidine. $^1$H NMR (DMSO-d$_6$) δ 1.43 (s, 9H), 2.37 (s, 3H), 7.27 (s, 1H), 8.60 (s, 1H), 11.28 (br s, 1H).

Example 145B

This example as the trifluoroacetate salt was prepared as described in EXAMPLE 112 using 4-thiophen-3-ylphenylamine in place of 4-[1,2,4]triazol-1-ylphenylamine and EXAMPLE 145A in place of EXAMPLE 111. $^1$H NMR (DMSO-d$_6$) δ 1.38 (s, 9H), 2.31 (s, 3H), 7.03 (s, 1H), 7.52 (d, J=4 Hz, 1H), 7.61 (m, 1H), 7.63 (d, J=8 Hz, 2H), 7.76 (d, J=8 Hz, 2H), 7.77 (s, 1H), 8.27 (s, 1H), 9.46 (s, 1H), 10.45 (s, 1H).

Example 146

EXAMPLE 53B (141 mg), 3-aminobenzenesulfonamide (157 mg), and trifluoroacetic acid (0.016 mL) were heated in 1 mL 2,2,2-trifluoroethanol for 6 hours. The mixture was cooled and concentrated and the residue purified by HPLC using a gradient of 10/90 to 90/10 acetonitrile/0.1% trifluoroacetic acid in water to provide the title compound as the trifluoroacetate salt. $^1$H NMR (DMSO-d$_6$) δ 10.50 (br s, 1H), 9.64 (br s, 1H), 8.33 (m, 2H), 8.10 (br t, 1H), 7.98 (m, 2H), 7.43 (m, 2H), 7.28 (m, 3H), 1.39 (s, 9H).

Example 147

This example was prepared as described in EXAMPLE 146 using m-anisidine (188 mg) in place of 3-aminobenzenesulfonamide to give a yellow solid. $^1$H NMR (DMSO-d$_6$) δ 10.48 (br, 1H), 9.35 (br s, 1H), 8.30 (d, 1H), 8.27 (br s, 1H), 7.32 (t, 1H), 7.21 (m, 3H), 6.53 (m, 1H), 3.72 (s, 3H), 1.34 (s, 9H).

Example 148

This example as the trifluoroacetate salt was prepared as described in EXAMPLE 146 using 4-(4-benzylpiperazin-1yl)phenylamine (326 mg) in place of 3-aminobenzenesulfonamide to give a yellow solid. $^1$H NMR (DMSO-d$_6$) δ 10.52 (br s, 1H), 9.27 (br s, 1H), 8.25 (s, 1H), 8.23 (s, 1H), 7.52 (m, 7H), 7.08 (br d, 1H), 6.93 (d, 2H), 4.41 (br s, 2H), 3.71 (m, 2H), 3.41 (m, 2H), 3.19 (m, 2H), 2.91 (m, 2H), 1.33 (s, 9H).

Example 149

This example as the trifluoroacetate salt was prepared as described in EXAMPLE 146 using 4-nitroaniline (167 mg) in place of 3-aminobenzenesulfonamide to give a yellow solid. $^1$H NMR (DMSO-d$_6$) δ 10.52 (s, 1H), 10.19 (s, 1H), 8.42 (d, 1H), 8.26 (br s, 1H), 8.18 (d, 2H), 7.95 (d, 2H), 7.40 (d, 1H), 1.39 (s, 9H).

Example 150

This example as the trifluoroacetate salt was prepared as described in EXAMPLE 146 using 5-amino-2-chloro-picoline (209 mg) in place of 3-aminobenzenesulfonamide to give a yellow solid. $^1$H NMR (DMSO-d$_6$) δ 10.43 (br s, 1H), 9.64 (s, 1H), 8.63 (d, 1H), 8.36 (d, 1H), 8.25 (br s, 1H), 8.04 (d, 1H), 7.34 (d, 1H), 2.32 (s, 3H), 1.39 (s, 9H).

Example 151A 4-amino-3-methoxybenzoic acid (250 mg) and 1,1'-carbonyldiimidazole (248 mg) were stirred in 5 mL acetonitrile for 1 hour. 4-Amino-1-methylpiperidine (205 mg) in 4 mL acetonitrile was added and the mixture refluxed for 4 hours. The mixture was cooled, concentrated, and partitioned between dichloromethane and water. The organic phase was washed with 10% aqueous sodium hydroxide and brine, dried over magnesium sulfate and concentrated. $^1$H NMR (DMSO-d$_6$) δ 7.75 (br d, 1H), 7.29 (m, 2H), 6.58 (d, 1H), 5.19 (s, 2H), 3.80 (s, 3H), 3.68 (m, 1H), 2.74 (m, 2H), 2.15 (s, 3H), 1.91 (m, 2H), 1.71 (m, 2H), 1.54 (m, 2H).

Example 151B

EXAMPLE 111 (161 mg), EXAMPLE 151A (150 mg), palladium (II) acetate (6 mg), 4,5-bis(diphenylphosphino)-9,9-dimethylxanthene (5 mg), and cesium carbonate (372 mg) in 2.5 mL dioxane were heated at 160° C. for 40 minutes in a microwave. The mixture was concentrated and the residue purified HPLC using a gradient of 10/90 to 90/10 acetonitrile/0.1% trifluoroacetic acid in water to give the title compound as a trifluoracetate salt. $^1$H NMR (DMSO-d$_6$) δ 10.70 (br s, 1H), 8.27 (br s, 1H), 8.21 (d, 1H), 7.94 (d, 1H), 7.35 (s, 1H), 7.32 (s, 1H), 7.20 (br s, 1H), 6.74 (d, 1H), 4.51 (m, 2H), 4.11 (m, 1H), 3.83 (s, 3H), 3.16 (br t, 2H), 1.90 (m, 2H), 1.53 (m, 2H), 1.42 (s, 9H), 1.35 (m, 2H).

Example 152

A mixture of 4-aminopyrimidine (101.5 mg) and EXAMPLE 6 (101.6 mg) in N,N'-dimethylformamide (4 mL) was treated with a solution of 21% sodium ethoxide in ethanol (0.2 mL) and heated at 140° C. overnight. The solvent was removed and the residue purified by flash chromatography on silica gel using 20:1 to 10:1 dichloromethane/methanol to provide the title compound (57.8 mg, 46%). $^1$H NMR (DMSO-d$_6$) δ 11.00 (s, 1H), 9.01 (s, 1H), 8.80 (s, 1H), 8.57 (d, J=6 Hz, 1H), 7.54 (d, J=6 Hz, 1H), 1.45 (s, 9H).

Example 153

A solution of 3,4-diethoxy-3-cyclobutene-1,2-dione (3.07 g) in tetrahydrofuran (50 mL) was treated with sodium hydride (60% in mineral oil, 570 mg). The mixture was cooled to 0° C., and 4-amino-2-chloropyrimidine (1.84 g) was added in small portions. After 1 hour the reaction was warmed to ambient temperature and stirred overnight. The solvent was removed and the residue taken up in water and washed with 9:1 hexane/ethyl acetate. The aqueous solution was cooled to 0° C. and treated dropwise with neat S-α-methylbenzylamine (2.1 mL). After 1 hour the reaction was warmed to ambient temperature and stirred for 3 days. The precipitate was collected, washed with methanol, and dried to provide the title compound as a tan solid (3.14 g, 66%). $^1$H NMR (DMSO-d$_6$) δ 11.37 (bs, 1H), 8.42 (d, J=5.8 Hz, 1H), 8.03 (d, J=9.5 Hz, 1H), 7.27 (bs, 1H), 4.05-4.09 (m, 1H), 1.60-1.82 (m, 6H), 1.38-1.45 (m, 1H), 1.23 (d, J=6.8 Hz, 3H), 0.95-1.16 (m, 4H).

Example 154

This example was prepared as described in EXAMPLE 153 using R-α-methylbenzylamine in place of S-α-methylbenzylamine. $^1$H NMR (DMSO-d$_6$) δ 11.37 (bs, 1H), 8.42 (d, J=5.8 Hz, 1H), 8.03 (d, J=9.5 Hz, 1H), 7.27 (bs, 1H), 4.05-4.09 (m, 1H), 1.60-1.82 (m, 6H), 1.38-1.45 (m, 1H), 1.23 (d, J=6.8 Hz, 3H), 0.95-1.16 (m, 4H).

Example 155

A mixture of 4-(Thiophen-3-yl)aniline (55.3 mg) and EXAMPLE 153 (99.6 mg) were heated at 100° C. in n-butanol (3 mL) overnight. The precipitate was collected and rinsed with hot n-butanol followed by hexane to provide the title compound (78.4 mg, 53%). $^1$H NMR (DMSO-d$_6$) δ 10.73 (s, 1H), 9.80 (s, 1H), 8.31 (d, J=6 Hz, 1H), 8.20 (d, J=9 Hz, 1H), 7.75-7.80 (m, 1H), 7.68-7.71 (m, 4H), 7.53-7.64 (m, 2H), 7.34 (d, J=5.4 Hz, 1H), 1.65-1.70 (m, 6H), 1.18-1.33 (m, 2H), 1.14 (d, J=6.4 Hz, 3H), 0.86-1.00 (m, 4H).

Example 156

This example was prepared as described in EXAMPLE 155 using EXAMPLE 154 in place of EXAMPLE 153. $^1$H NMR (DMSO-d$_6$) δ 10.73 (s, 1H), 9.80 (s, 1H), 8.31 (d, J=6 Hz, 1H), 8.20 (d, J=9 Hz, 1H), 7.75-7.80 (m, 1H), 7.68-7.71 (m, 4H), 7.53-7.64 (m, 2H), 7.34 (d, J=5.4 Hz, 1H), 1.65-1.70 (m, 6H), 1.18-1.33 (m, 2H), 1.14 (d, J=6.4 Hz, 3H), 0.86-1.00 (m, 4H).

Example 157

This example was prepared as described in EXAMPLE 155 using 4-(4,6-dimethoxypyrimidin-2-yl)phenylamine in place of 4-(thiophen-3-yl)aniline. $^1$H NMR (DMSO-d$_6$) δ 10.57 (s, 1H), 9.83 (s, 1H), 8.36 (d, J=5.8 Hz, 1H), 8.33 (d, J=8.8 Hz, 2H), 8.15 (d, J=6.1 Hz, 1H), 7.85 (d, J=8.8 Hz, 2H), 7.36 (d, J=5.8 Hz, 1H), 6.11 (s, 1H), 3.99 (s, 6H), 1.54-1.75 (m, 6H), 1.21-1.34 (m, 2H), 1.16 (d, J=6.8 Hz, 3H), 0.88-1.10 (m, 4H).

Example 158

This example was prepared as described in EXAMPLE 156 using 4-(4,6-dimethoxypyrimidin-2-yl)phenylamine in place of 4-(thiophen-3-yl)aniline. $^1$H NMR (DMSO-d$_6$) δ 10.57 (s, 1H), 9.83 (s, 1H), 8.36 (d, J=5.8 Hz, 1H), 8.33 (d, J=8.8 Hz, 2H), 8.15 (d, J=6.1 Hz, 1H), 7.85 (d, J=8.8 Hz, 2H), 7.36 (d, J=5.8 Hz, 1H), 6.11 (s, 1H), 3.99 (s, 6H), 1.54-1.75 (m, 6H), 1.21-1.34 (m, 2H), 1.16 (d, J=6.8 Hz, 3H), 0.88-1.10 (m, 4H).

Example 159

A mixture of EXAMPLE 153 (69.2 mg), 4-pyridin-4-ylphenylamine (37.8 mg), palladium (II) acetate (3.0 mg), 4,5-bis(diphenylphosphino)-9,9-dimethylxanthene (9.6 mg), cesium carbonate (141.6 mg) and dioxane (2.5 ml) were heated in a microwave at 160° C. for 40 minutes. The solvent was removed and the residue purified by flash chromatography using 20:1 dichloromethane/methanol. Further purification by reverse phase HPLC afforded the title compound (12.8 mg, 13%). $^1$H NMR (DMSO-d$_6$) δ 10.40 (s, 1H), 9.84 (s, 1H), 8.81 (d, J=6.8 Hz, 2H), 8.38 (d, J=5.8 Hz, 1H), 8.24 (d, J=6.8 Hz, 2H), 7.94-8.04 (m, 5H), 7.34 (d, J=5.8 Hz, 1H), 1.55-1.75 (m, 6H), 1.27-1.36 (m, 2H), 1.17 (d, J=6.8 Hz, 3H), 0.87-1.12 (m, 4H).

Example 160

This example was prepared as described in EXAMPLE 159 using EXAMPLE 154 in place of EXAMPLE 153. $^1$H NMR (DMSO-d$_6$) δ 10.40 (s, 1H), 9.84 (s, 1H), 8.81 (d, J=6.8 Hz, 2H), 8.38 (d, J=5.8 Hz, 1H), 8.24 (d, J=6.8 Hz, 2H), 7.94-8.04 (m, 5H), 7.34 (d, J=5.8 Hz, 1H), 1.55-1.75 (m, 6H), 1.27-1.36 (m, 2H), 1.17 (d, J=6.8 Hz, 3H), 0.87-1.12 (m, 4H).

Example 161A

A solution of 3,4-diethoxy-3-cyclobutene-1,2-dione (10.3 mL) in tetrahydrofuran (200 mL) was treated with sodium hydride (60% dispersion in mineral oil, 2.16 g). The mixture was cooled to 0° C., and 4-amino-2-chloropyrimidine (7.00 g) was added in small portions. After 1 hour the reaction was warmed to ambient temperature and stirred for 3 days. The solvent was removed and the residue was taken up in water and washed with 9:1 hexane/ethyl acetate. The aqueous solution was cooled to 0° C. and treated dropwise with neat t-butylamine (5.8 mL). The mixture was warmed to ambient temperature and after 1 day, additional t-butylamine (1.2 mL) was added. The mixture was stirred at ambient temperature for another 2 days and the precipitate was collected and washed with water, triturated in methanol, filtered, and rinsed with methanol. The solid was collected, vigorously shaken in water for 10 minutes, filtered, washed with additional water, and dried to provide the title compound (6.09 g, 40%).

Example 161B

A mixture of 4-(4-aminopiperidino)pyridine dihydrochloride (90.1 mg), EXAMPLE 161A (100.0 mg), potassium carbonate (147.1 mg), and n-butanol (3.0 mL) was heated at 100° C. overnight. The solvent was removed and the residue purified by reverse phase HPLC to provide the title compound (54.6 mg, 36%). $^1$H NMR (DMSO-d$_6$) δ 11.12 (s, 1H), 9.37 (d, J=8.1 Hz, 2H), 8.72 (d, J=5.8 Hz, 1H), 8.24 (s, 1H), 7.97 (bs, 2H), 7.48 (d, J=8.1 Hz, 2H), 4.41-4.49 (m, 2H), 3.37-3.45 (m, 4H), 2.07-2.20 (m, 2H), 1.57-1.62 (m, 1H), 1.44 (s, 9H).

Example 162

A mixture of EXAMPLE 161A (101.4 mg), 4-(1-methylpiperidin-4-yl)-phenylamine (76.1 mg), palladium(II) acetate (3.6 mg), 4,5-bis(diphenylphosphino)-9,9-dimethylxanthene (13.0 mg), cesium carbonate (238.2 mg), and dioxane (4.5 ml) were heated in a microwave at 160° C. for 40 minutes. The solvent was removed and the residue purified by reverse phase HPLC to provide the title compound as the trifluoroacetate salt. $^1$H NMR (DMSO-d$_6$) δ 9.28 (s, 1H), 8.27 (d, J=8.5 Hz, 2H), 7.56 (d, J=8.5 Hz, 2H), 7.11-7.16 (m, 4H), 2.88-2.95 (m, 2H), 2.26 (s, 3H), 2.02-2.10 (m, 2H), 1.60-1.73 (m, 3H), 1.33 (s, 9H), 1.13-1.20 (m, 2H).

Example 163A

A solution of 3,4-diethoxy-3-cyclobutene-1,2-dione (2.21 g) in tetrahydrofuran (35 mL) was treated with sodium hydride (60% in mineral oil, 0.040 g). The mixture was cooled to 0° C. and 4-amino-2-chloropyrimidine (1.29 g) was added in portions. The reaction was warmed to ambient temperature, stirred for 3 days and concentrated. The residue was taken up in water and washed with 9:1 hexane/ethyl acetate. The aqueous solution was cooled to 0° C. and t-butyl 4-aminopiperidine-1-carboxylate (2.01 g) added in portions. The mixture was warmed to ambient temperature, stirred for 3 days, and the resulting precipitate collected, washed with water and dried.

Example 163B

A mixture of EXAMPLE 163A (298.8 mg), 4-pyridin-4-yl-phenylamine (124.9 mg), palladium(II) acetate (7.7 mg), 4,5-bis(diphenylphosphino)-9,9-dimethylxanthene (25.6 mg), cesium carbonate (0.46 g), and dioxane (5 mL) were heated in a microwave at 160° C. for 40 minutes. The solvent was removed and the residue purified by flash chromatography on silica gel using 15% methanol/dichloromethane to provide the title compound (141.6 mg, 36%) as a tan powder.

Example 163C

A suspension of EXAMPLE 163B (140.9 mg) in dichloromethane (5 mL) and methanol (0.2 mL) was treated with trifluoroacetic acid (5 mL) and stirred at ambient temperature overnight. The solvent was removed and the residue triturated with methanol/dichloromethane and purified by reverse phase HPLC to provide the title compound (45.2 mg). $^1$H NMR (DMSO-d$_6$) δ 9.61 (s, 1H), 8.59 (d, J=4.5 Hz, 2H), 8.32 (d, J=5.4 Hz, 1H), 8.10-8.20 (bs, 1H), 7.87 (d, J=8.8 Hz, 2H), 7.77 (d, J=8.8 Hz, 2H), 7.68 (d, J=4.5 Hz, 2H), 7.18 (d, J=5.4 Hz, 1H), 3.85-3.94 (bs, 1H), 2.87-2.97 (m, 4H), 1.77-1.84 (m, 2H), 1.29-1.42 (m, 2H).

Example 164A

A mixture of EXAMPLE 161A (400 mg) and 3-aminobenzoic acid (201 mg) in n-butanol (10 mL) was heated at 100-115° C. overnight. The precipitate was collected, washed with hexane and dried.

Example 164B

A solution of EXAMPLE 164A (75.0 mg), 4-amino-1-methylpiperidine (25.7 mg) and 4-dimethylaminopyridine (27.7 mg) in N,N'-dimethylformamide (2 mL) was treated with 1-methyl-4-aminopiperidine (0.25 mL) and 1-ethyl-3-(3'-dimethylaminopropyl)carbodiimide (41.9 mg). The mixture was stirred at ambient temperature for 1 day, additional 1-methyl-4-aminopiperidine was added and the mixture stirred overnight. The solvent was removed and the residue purified by reverse phase HPLC to provide the title compound (50.9 mg). $^1$H NMR (DMSO-d$_6$) δ 10.54 (s, 1H), 9.50 (s, 1H), 8.40 (d, J=7.5 Hz, 1H), 8.32 (d, J=5.7 Hz, 1H), 8.26 (s, 1H), 8.05 (s, 1H), 7.85 (d, J=8.8 Hz, 1H), 7.35-7.46 (m, 2H), 7.18 (d, J=5.7 Hz, 1H), 3.42-3.51 (m, 2H), 3.04-3.15 (m, 2H), 2.78 (s, 3H), 1.94-2.05 (m, 3H), 1.67-1.82 (m, 2H), 1.34 (s, 9H).

Example 165

This example was prepared as described in EXAMPLE 164B using cycloheptylamine in place of 1-methyl-4-aminopiperidine. $^1$H NMR (DMSO-d$_6$) δ 10.55 (s, 1H), 9.51 (s, 1H), 8.31 (d, J=5.4 Hz, 1H), 8.26 (s, 1H), 8.12 (d, J=8.1 Hz, 1H), 8.01 (s, 1H), 7.80 (d, J=8.1 Hz, 1H), 7.44 (d, J=7.8 Hz, 1H), 7.33-7.38 (m, 1H), 7.20 (d, J=5.8 Hz, 1H), 1.77-1.88 (m, 4H), 1.37-1.70 (m, 9H), 1.33 (s, 9H).

Example 166

This example was prepared as described in EXAMPLE 164B using cyclohexylamine in place of 1-methyl-4-aminopiperidine. $^1$H NMR (DMSO-d$_6$) δ 10.56 (s, 1H), 9.54 (s, 1H), 8.31 (d, J=5.8 Hz, 1H), 8.26 (s, 1H), 8.09 (d, J=7.8 Hz, 1H), 8.01 (s, 1H), 7.82 (d, J=7.8 Hz, 1H), 7.45 (d, J=7.8 Hz, 1H), 7.33-7.38 (m, 1H), 7.21 (d, J=5.8 Hz, 1H), 1.68-1.85 (m, 4H), 1.56-1.65 (m, 1H), 1.33 (s, 9H) 1.10-1.30 (m, 6H).

Example 167

This example was prepared as described in EXAMPLE 164B using cyclopentylamine in place of 1-methyl-4-aminopiperidine. $^1$H NMR (DMSO-d$_6$) δ 10.53 (s, 1H), 9.49 (s, 1H), 8.31 (d, J=5.4 Hz, 1H), 8.26 (s, 1H), 8.17 (d, J=7.1 Hz, 1H), 8.02 (s, 1H), 7.82 (d, J=8.8 Hz, 1H), 7.44 (d, J=7.5 Hz, 1H), 7.21-7.38 (m, 1H), 7.20 (d, J=5.8 Hz, 1H), 4.16-4.25 (m, 1H) 1.81-1.91 (m, 2H), 1.64-1.70 (m, 2H), 1.47-1.57 (m, 4H) 1.33 (s, 9H).

Example 168

This example was prepared as described in EXAMPLE 164B using cyclobutylamine in place of 1-methyl-4-aminopiperidine. $^1$H NMR (DMSO-d$_6$) δ 10.54 (s, 1H), 9.51 (s, 1H), 8.50 (d, J=7.8 Hz, 1H), 8.31 (d, J=5.8 Hz, 1H), 8.27 (s, 1H), 8.02 (s, 1H), 7.83 (d, J=8.1 Hz, 1H), 7.46 (d, J=7.8 Hz, 1H), 7.34-7.39 (m, 1H), 7.22 (d, J=5.8 Hz, 1H), 4.34-4.44 (m, 1H), 2.15-2.25 (m, 2H), 1.99-2.09 (m, 2H), 1.62-1.71 (m, 2H) 1.34 (s, 9H).

Example 169A

This example was prepared as described in EXAMPLE 164A using 3-amino-4-methoxybenzoic acid in place of 3-aminobenzoic acid.

Example 169B

A mixture of EXAMPLE 169A (41.1 mg) and O-(benzotriazol-1-yl)-N,N,N',N'-tetramethyluronium tetrafluoroborate (33.8 mg) in dichloromethane (1 mL) was treated with N,N-diisopropylethylamine (0.04 mL) and stirred for 30 minutes. Cyclohexylamine (0.03 mL) was added and the mixture stirred at ambient temperature overnight. The solvent was removed and the residue purified by reverse phase HPLC to provide the title compound (5.9 mg). $^1$H NMR (DMSO-d$_6$) δ 10.62 (s, 1H), 8.47 (d, J=2.0 Hz, 1H), 8.42 (s, 1H), 8.29 (d, J=5.8 Hz, 1H), 7.96-8.03 (m, 2H), 7.58 (dd, J=8.5, 2.0 Hz, 1H), 7.05-7.10 (m, 2H), 3.87 (s, 3H), 3.68-3.77 (m, 1H), 1.67-1.85 (m, 4H), 1.55-1.65 (m, 2H), 1.40 (s, 9H), 1.24-1.37 (m, 4H).

Example 170

A mixture of 6-aminoquinoline (29 mg), EXAMPLE 111 (56 mg), cesium carbonate (130 mg), palladium (II) acetate (2 mg), 4,5-bis(diphenylphosphino)-9,9-dimethylxanthene (9 mg) and dioxane (1.2 mL) was heated at 160° C. for 40 minutes by microwave. The residue was purified as described in EXAMPLE 12D to give 75 mg of the title compound as the trifluoroacetate salt: $^1$H NMR (DMSO-d$_6$) δ 1.38 (s, 9H), 7.31 (d, J=6 Hz, 1H), 7.76 (dd, J=6, 8 Hz, 1H), 8.08 (d, J=8 Hz, 1H), 8.15 (d, J=8 Hz, 1H), 8.24 (s, 1H), 8.42 (d, J=6 Hz, 1H), 8.60 (s, 1H), 8.63 (d, J=8 Hz, 1H), 8.92 (d, J=4 Hz, 1H), 10.00 (s, 1H), 10.57 (s, 1H).

Example 171

A mixture of EXAMPLE 3 (30 mg), 4-fluoro-3-methylphenylamine (12.5 mg), toluene (2 mL), and p-toluenesulfonic acid (1.5 mg) was heated to 86° C. and stirred overnight. The mixture was cooled, concentrated and the residue purified as described in EXAMPLE 12D to give 10.3 mg of the title compound as the trifluoroacetate salt. $^1$H NMR (DMSO-d$_6$) δ 0.90 (s, 9H), 1.15 (d, J=7 Hz, 3H), 2.21 (s, 3H), 4.00 (m, 1H), 7.08 (t, J=8 Hz, 1H), 7.32 (d, J=6 Hz, 1H), 7.45 (d, J=8 Hz, 1H), 7.55 (t, J=8 Hz, 1H), 7.95 (d, J=8 Hz, 1H), 8.30 (d, J=6 Hz, 1H), 9.18 (s, 1H), 10.18 (s, 1H).

Example 172

This example as the trifluoroacetate salt was prepared as described in EXAMPLE 109 using 2'-methoxybiphenyl-4-ylamine in place of 4-[1,2,3]thiadiazol-4-ylphenylamine. $^1$H NMR (DMSO-d$_6$) δ 1.30 (s, 9H), 3.76 (s, 3H), 7.00 (t, J=7 Hz, 1H), 7.12 (d, J=7 Hz, 1H), 7.24 (d, J=7 Hz, 1H), 7.31 (t, J=7 Hz, 1H), 7.35 (d, J=8 Hz, 2H), 7.66 (d, J=8 Hz, 2H), 7.81 (s, 1H), 8.38 (s, 1H), 9.48 (s, 1H), 10.82 (s, 1H).

Example 173A

This example was prepared as described in EXAMPLE 161A by substituting 2-amino-2-methylpropan-1-ol for tert-butylamine.

Example 173B

A mixture of EXAMPLE 173A (27 mg), 4-amino-N-cyclobutyl-3-methoxybenzamide (20 mg) and para-toluenesulfonic acid monohydrate in THF was stirred at 72° C. overnight, cooled and concentrated. The concentrate was purified by reverse phase HPLC. $^1$H NMR (DMSO-d$_6$) δ 1.40 (s, 6H), 1.59-1.76 (m, 2H), 1.96-2.14 (m, 2H), 2.16-2.31 (m, 2H), 3.50 (s, 2H), 3.90 (s, 3H), 4.43 (m, 1H), 5.64 (s, brd, 1H), 6.90 (d, J=5.1 Hz, 1H), 7.41-7.54 (m, 2H), 8.13 (m, 1H), 8.27 (d, J=5.8 Hz, 1H), 8.41 (s, 1H), 8.49 (d, J=7.5 Hz, 1H), 9.10 (s, 1H), 10.91 (s, 1H).

Example 174A

This example was prepared as described in EXAMPLE 161A by substituting 2-phenylpropan-2-amine for tert-butylamine.

Example 174B

This example was prepared as described in EXAMPLE 173B by substituting EXAMPLE 174A for EXAMPLE 173A. $^1$H NMR (DMSO-d$_6$) δ 1.59-1.75 (m, 2H), 1.81 (s, 6H), 1.98-2.31 (m, 4H), 3.85 (s, 3H), 4.42 (m, 1H), 7.11-7.29 (m, 2H), 7.35 (t, J=7.6 Hz, 2H), 7.42-7.56 (m, 4H), 7.89 (s, 1H), 8.30-8.41 (m, 2H), 8.46 (d, J=7.5 Hz, 1H), 8.75 (s, 1H), 10.75 (s, 1H).

Example 175A

This example was prepared as described in EXAMPLE 161A by substituting 2-methylbut-3-yn-2-amine for tert-butylamine.

Example 175B

This example was prepared as described in EXAMPLE 173B by substituting EXAMPLE 175A for EXAMPLE 173A. $^1$H NMR (DMSO-d$_6$) δ 1.61-1.71 (m, 2H), 1.73 (s, 6H), 1.98-2.30 (m, 4H), 3.93 (s, 3H), 4.43 (m, 1H), 7.16 (d, J=5.4 Hz, 1H), 7.44-7.53 (m, 3H), 7.98 (s, 1H), 8.26-8.40 (m, 2H), 8.47 (d, J=7.1 Hz, 1H), 8.67 (s, 1H), 10.71 (s, 1H).

Example 176A

This example was prepared as described in EXAMPLE 161A by substituting 2-amino-2-methylpropanenitrile for tert-butylamine.

Example 176B

This example was prepared as described in EXAMPLE 173B by substituting EXAMPLE 176A for EXAMPLE

Example 177A

This example was prepared as described in EXAMPLE 161A by substituting 2-cyclopropylpropan-2-amine for tert-butylamine.

Example 177B

This example was prepared as described in EXAMPLE 173B by substituting EXAMPLE 177A for EXAMPLE 173A. $^1$H NMR (DMSO-$d_6$) δ 0.34-0.48 (m, 3H), 1.32 (s, 6H), 1.31-1.40 (m, 2H), 1.59-1.75 (m, 2H), 1.99-2.29 (m, 4H), 3.91 (s, 3H), 4.42 (m, 1H), 7.20 (d, J=5.8 Hz, 1H), 7.46-7.55 (m, 2H), 7.89 (s, 1H), 8.30-8.40 (m, 2H), 8.42-8.52 (m, 2H), 10.73 (s, 1H).

Example 178A

This example was prepared as described in EXAMPLE 161A by substituting 2-methyl-1-morpholinopropan-2-amine for tert-butylamine.

Example 178B

This example was prepared as described in EXAMPLE 162 by substituting EXAMPLE 178A for EXAMPLE 161A and 4-amino-N-cyclobutyl-3-methoxybenzamide for 4-(1-methylpiperidin-4-yl)phenylamine $^1$H NMR (CD$_3$OD) δ 1.62 (s, 6H), 1.73-1.85 (m, 2H, 2.07-2.19 (m, 2H), 2.29-2.41 (m, 2H), 3.36 (brs, 4H), 3.72 (brs, 2H), 3.88 (brs, 4H), 3.99 (s, 3H), 4.50 (m, 1H), 6.93 (brs, 1H), 7.47-7.55 (m, 2H), 8.33 (d, J=5.8 Hz, 1H), 8.44 (d, J=8.5 Hz, 1H).

Example 179A

This example was prepared as described in EXAMPLE 161A by substituting morpholine for tert-butylamine.

Example 179B

This example was prepared as described in EXAMPLE 162 by substituting EXAMPLE 179A for EXAMPLE 161A and 4-amino-N-cyclobutyl-3-methoxybenzamide for 4-(1-methylpiperidin-4-yl)phenylamine. $^1$H NMR (CD$_3$OD) δ 1.70-1.88 (m, 2H), 2.04-2.23 (m, 2H), 2.28-2.46 (m, 2H), 3.43-3.88 (m, 8H, brd), 4.00 (s, 3H), 4.50 (m, 1H), 6.62 (d, J=6.8 Hz, 1H), 7.47 (dd, J=8.5, 1.7 Hz, 1H), 7.57 (d, J=1.7 Hz, 1H), 8.04-8.20 (m, 2H).

Example 180A

This example was prepared as described in EXAMPLE 161A by substituting 4-amino-4-methylpentan-2-one hydrogenoxylate and sodium bicarbonate (2.1 equiv) for tert-butylamine.

Example 180B

This example was prepared as described in EXAMPLE 173B by substituting EXAMPLE 180A for EXAMPLE 173A. $^1$H NMR (DMSO-$d_6$) δ 1.49 (s, 6H), 1.62-1.76 (m, 2H), 2.00-2.15 (m, 5H), 2.17-2.28 (m, 2H), 3.04 (s, 2H), 3.90 (s, 3H), 4.43 (m, 1H), 7.07 (s, 1H), 7.44-7.56 (m, 2H), 8.13 (s, 1H), 8.31-8.43 (m, 2H), 8.48 (d, J=7.3 Hz, 1H), 8.62 (s, 1H), 10.85 (s, 1H).

Example 181A

This example was prepared as described in EXAMPLE 161A by substituting propylamine for tert-butylamine.

Example 181B

This example was prepared as described in EXAMPLE 173B by substituting EXAMPLE 181A for EXAMPLE 173A. $^1$H NMR (DMSO-$d_6$) δ 0.88 (t, J=7.3 Hz, 3H), 1.45-1.58 (m, 2H), 1.61-1.71 (m, 2H), 1.99-2.13 (m, 2H), 2.18-2.29 (m, 2H), 3.43-3.52 (m, 2H), 3.90 (s, 3H), 4.42 (m, 1H), 6.79 (d, J=5.2 Hz, 1H), 7.46-7.54 (m, 2H), 7.99 (t, J=6.4 Hz, 1H), 8.13 (d, J=8.2 Hz, 1H), 8.26 (d, J=5.5 Hz, 1H), 8.32 (s, 1H), 8.51 (d, J=7.6 Hz, 1H), 10.84 (s, 1H).

Example 182A

This example was prepared as described in EXAMPLE 161A by substituting aniline for tert-butylamine.

Example 182B

This example was prepared as described in EXAMPLE 173B by substituting EXAMPLE 182A for EXAMPLE 173A. $^1$H NMR (DMSO-$d_6$) δ 1.59-1.78 (m, 2H), 2.01-2.14 (m, 2H), 2.16-2.29 (m, 2H), 3.91 (s, 3H), 4.41 (m, 1H), 7.04 (s, 1H), 7.12 (t, J=7.2 Hz, 1H), 7.33-7.44 (m, 4H), 7.45-7.51 (m, 2H), 8.18 (s, 1H), 8.29 (d, J=8.5 Hz, 1H), 8.38 (d, J=5.5 Hz, 1H), 8.44 (d, J=7.3 Hz, 1H), 10.28 (s, 1H), 10.98 (s, 1H).

Example 183A

A mixture of EXAMPLE 161A (0.63 mmol), sodium sulfide hydrate (70 mg) and propylbromide (227 mg) in water (2 mL) and THF (1 mL) was stirred at ambient temperature for 1 day, diluted with ethyl acetate, washed with brine and dried, filtered and concentrated.

Example 183B

This example was prepared as described in EXAMPLE 162 by substituting EXAMPLE 183A for EXAMPLE 161A and 4-amino-N-cyclobutyl-3-methoxybenzamide for 4-(1-methylpiperidin-4-yl)phenylamine $^1$H NMR (DMSO-$d_6$) δ 1.05 (t, J=7.4 Hz, 3H), 1.61-1.72 (m, 2H), 1.72-1.79 (m, 2H), 2.02-2.14 (m, 2H), 2.17-2.28 (m, 2H), 3.47 (t, J=7.2 Hz, 2H), 3.96 (s, 3H), 4.42 (m, 1H), 6.69 (d, J=5.5 Hz, 1H), 7.49-7.55 (m, 2H), 8.03 (s, 1H), 8.42 (d, J=5.5 Hz, 1H), 8.46 (d, J=8.9 Hz, 1H), 8.50 (d, J=7.7 Hz, 1H), 11.76 (s, 1H).

Example 184A

A mixture of 4-amino-2-bromo-pyridine (213 mg), EXAMPLE 6 (100 mg) and 21 wt % sodium ethoxide in ethanol (0.3 mL) in dimethylsulfoxide (3 mL) was heated at 155° C. under microwave conditions for 20 minutes and concentrated. The concentrate was purified by reverse phase HPLC on a RP18 prep cartridge with 0.1% trifluoroacetic acid/water/acetonitrile. $^1$H NMR (DMSO-$d_6$) δ 1.43 (s, 9H), 7.33 (dd, J=5.7, 2.0 Hz, 1H), 7.86 (d, J=1.8 Hz, 1H), 8.04 (s, 1H), 8.20 (d, J=5.8 Hz, 1H), 10.03 (s, 1H).

Example 184B

A mixture of EXAMPLE 184A (50 mg), biphenyl-4-amine (31.3 mg), palladium(II) acetate (2 mg), 4,5-bis(diphenylphosphino)-9,9-dimethylxanthene (7.8 mg) and cesium carbonate (98 mg) in dioxane (2 mL) at 160° C. was stirred for 80 minutes under microwave conditions and concentrated. The concentrate was purified by reverse phase HPLC. $^1$H NMR (DMSO-$d_6$) δ 1.43 (s, 9H), 7.01 (s, 1H), 7.13 (d, J=5.2 Hz, 1H), 7.35 (t, J=7.3 Hz, 1H), 7.47 (t, J=7.6 Hz, 2H), 7.57 (d, J=8.2 Hz, 2H), 7.68 (d, J=7.0 Hz, 2H), 7.71 (d, J=8.5 Hz, 2H), 8.00 (d, J=6.4 Hz, 1H), 8.12 (s, 1H), 9.88 (s, 1H), 10.22 (s, 1H).

Example 185

This example was prepared as described in EXAMPLE 184 by substituting 4-(pyridin-4-yl)aniline for biphenyl-4-amine. $^1$H NMR (DMSO-$d_6$) δ 1.11-1.61 (m, 9H), 7.04 (s, 1H), 7.06-7.12 (m, 1H), 7.85 (d, J=7.9 Hz, 2H), 8.01 (d, J=8.8 Hz, 2H), 8.08 (s, 1H), 8.11 (d, J=6.1 Hz, 1H), 8.19 (d, J=4.9 Hz, 2H), 8.78 (d, J=6.1 Hz, 2H), 9.75 (s, 1H), 9.99 (s, 1H).

Example 186

This example was prepared as described in EXAMPLE 184 by substituting 4-amino-N-cyclohexyl-3-methoxybenzamide for biphenyl-4-amine. $^1$H NMR (DMSO-$d_6$) δ 1.06-1.21 (m, 1H), 1.24-1.39 (m, 4H), 1.43 (s, 9H), 1.58-1.67 (m, 1H), 1.69-1.80 (m, 2H), 1.80-1.91 (m, 2H), 3.70-3.85 (m, 1H), 3.89 (s, 3H), 7.04 (d, J=0.9 Hz, 1H), 7.12 (dd, J=6.3, 1.1 Hz, 1H), 7.54 (d, J=8.0 Hz, 1H), 7.58 (m, 1H), 7.57-7.60 (m, 1H), 7.95 (d, J=6.7 Hz, 1H), 8.16 (s, 1H), 8.18 (d, J=7.7 Hz, 1H), 9.55 (s, 1H), 10.31 (s, 1H).

Example 187A

A mixture of 4-amino-3-methoxybenzoic acid (0.93 g), cyclopentylamine (0.64 mL), HATU (2.5 g) and TEA (0.90 mL) in DMF (20 mL) was stirred at ambient temperature for 3 days and diluted with water and ethyl acetate. The extract was washed with brine and dried ($Na_2SO_4$), filtered and concentrated. The concentrate was purified by flash column chromatography on silica gel with 45:55 hexanes/ethyl acetate. $^1$H NMR (DMSO-$d_6$) δ 1.51 (m, 4H), 1.68 (m, 2H), 1.85 (m, 2H), 3.80 (s, 3H), 4.18 (m, 1H), 5.18 (s, 2H), 6.59 (d, J=8 Hz, 1H), 7.28 (m, 2H), 7.81 (br d, J=7 Hz, 1H).

Example 187B

To a solution of 2-amino-4-chloropyrimidine (0.23 g) and 3,4-diethoxycyclobut-3-ene-1,2-dione (0.35 g) in THF (5 mL) at ambient temperature was added 95% oily sodium hydride (55 mg). The mixture was stirred overnight, treated with diethylamine (0.14 g), stirred overnight, and concentrated. The concentrate was purified by flash column chromatography on silica gel with 15:85 hexane/ethyl acetate. $^1$H NMR (DMSO-$d_6$) δ 1.18 (m, 6H), 3.55 (m, 2H), 3.75 (m, 2H), 7.05 (d, J=6 Hz, 1H), 8.40 (d, J=6 Hz, 1H), 10.75 (brs, 1H).

Example 187C

To a solution of EXAMPLE 187A (34 mg) and EXAMPLE 187B (40 mg) in dioxane (0.5 mL) was added para-toluenesulfonic acid monohydrate (25 mg). The mixture was stirred at 70° C. overnight and concentrated. The concentrate was purified by reverse phase HPLC. $^1$H NMR (DMSO-$d_6$) δ 1.16 (m, 6H), 1.64 (m, 4H), 1.71 (m, 2H), 1.90 (m, 2H), 3.83 (s, 3H), 4.23 (m, 1H), 6.61 (d, J=6 Hz, 1H), 7.45 (dd, J=8 Hz, 2 Hz, 1H), 7.51 (d, J=2 Hz, 1H), 8.18 (d, J=7 Hz, 1H), 8.24 (d, J=7 Hz, 1H), 8.26 (d, J=7 Hz, 1H), 8.46 (brs, 1H), 10.49 (brs, 1H).

Example 188A

To a solution of 3,4-diethoxycyclobut-3-ene-1,2-dione (1.2 g) in THF (20 mL) at 0° C. was added 1M solution neopentylmagnesium bromide in diethyl ether (9 mL). The mixture was stirred at 0° C. for 10 minutes and at ambient temperature for 20 minutes, treated with 6M hydrochloric acid (25 mL) and extracted with diethyl ether. The extract was washed with brine and dried ($Na_2SO_4$), filtered and concentrated. The concentrate was flash chromatographed in silica gel with 93:7 hexane/ethyl acetate. $^1$H NMR (CDCl$_3$) δ 1.02 (s, 9H), 1.48 (t, J=7 Hz, 3H), 2.49 (s, 2H), 4.81 (q, J=7 Hz, 2H).

Example 188B

To a solution of 2-amino-4-chloropyrimidine (0.13 g) and EXAMPLE 188A (0.19 g) in THF (2.5 mL) was added 95% sodium hydride (28 mg). The mixture was stirred at ambient temperature overnight and concentrated. The concentrate was flash chromatographed in silica gel with 6:4 hexanes/ethyl acetate. $^1$H NMR (DMSO-$d_6$) δ 0.94 (s, 9H), 2.97 (s, 2H), 7.53 (d, J=6 Hz, 1H), 8.63 (d, J=6 Hz, 1H), 11.98 (brs, 1H).

Example 188C

This example was prepared as described in EXAMPLE 187C by substituting EXAMPLE 188B for EXAMPLE 187B. $^1$H NMR (DMSO-$d_6$) δ 0.92 (s, 9H), 1.54 (m, 4H), 1.71 (m, 2H), 1.90 (m, 2H), 2.86 (s, 2H), 3.83 (s, 3H), 4.23 (m, 1H), 6.97 (d, J=6 Hz, 1H), 7.51 (m, 2H), 8.07 (s, 1H), 8.16 (d, J=7 Hz, 1H), 8.28 (d, J=9 Hz, 1H), 8.44 (d, J=6 Hz, 1H), 11.44 (s, 1H).

Example 189A

This example was prepared as described in EXAMPLE 188A by substituting pentyl-3-magnesium bromide for neopentylmagnesium bromide. $^1$H NMR (DMSO-$d_6$) δ 0.85 (t, J=7 Hz, 6H), 1.38 (t, J=7 Hz, 3H), 1.62 (m, 4H), 2.82 (m, 1H), 4.73 (q, J=7 Hz, 2H).

Example 189B

This example was prepared as described in EXAMPLE 188B, by substituting EXAMPLE 189A for EXAMPLE 188A.

Example 189C

This example was prepared as described in EXAMPLE 187C by substituting EXAMPLE 189B for EXAMPLE 187B. This example precipitated out of the reaction mixture and was isolated by filtration. $^1$H NMR (DMSO-$d_6$) δ 0.86 (t, J=7 Hz, 6H), 1.54 (m, 4H), 1.71 (m, 6H), 1.91 (m, 2H), 2.29 (s, 3H), 3.29 (m, 1H), 4.24 (m, 1H), 7.03 (d, J=6 Hz, 1H), 7.11

(d, J=8 Hz, 2H), 7.47 (d, J=8 Hz, 2H), 7.54 (m, 2H), 8.19 (d, J=7 Hz, 1H), 8.27 (d, J=9 Hz, 1H), 8.28 (brs, 1H), 8.45 (d, J=6 Hz, 1H), 11.52 (s, 1H).

Example 190A

A solution of 1.7M tert-butyl lithium in pentane (4.6 mL) was added to THF (20 mL) at −78° C., followed by 1-bromo-2-methyl-1-propene (0.53 g). The mixture was stirred for 30 minutes, treated with 3,4-diethoxycyclobut-3-ene-1,2-dione (0.52 g) in THF (30 mL), stirred for 40 minutes, treated with trifluoroacetic anhydride (1.4 g), stirred for 10 minutes, treated with water (10 mL) and extracted with diethyl ether. The extract was washed with brine and dried ($Na_2SO_4$), filtered and concentrated. The concentrate was flash chromatographed in silica gel with 93:7 hexane/ethyl acetate. $^1$H NMR (DMSO-$d_6$) δ 1.40 (t, J=7 Hz, 3H), 1.99 (d, J=1 Hz, 3H), 2.14 (s, 3H), 4.77 (q, J=7 Hz, 2H), 6.05 (m, 1H).

Example 190B

This example was prepared as described in EXAMPLE 188B by substituting EXAMPLE 190A for EXAMPLE 188A. $^1$H NMR (DMSO-$d_6$) δ 2.02 (s, 3H), 2.18 (s, 3H), 6.73 (s, 1H), 7.65 (d, J=6 Hz, 1H), 8.63 (d, J=6 Hz, 1H), 11.92 (brs, 1H).

Example 190C

A mixture of EXAMPLE 190B (30 mg), EXAMPLE 187A (26 mg), palladium(II) acetate (3.8 mg), 9,9-dimethyl-4,5-bis (diphenylphosphino)xanthene (13.7 mg) and cesium carbonate (85 mg) in dioxane (1.8 mL) was heated in a microwave reactor at 150° C. for 10 minutes, filtered through diatomaceous earth (Celite®) and concentrated. The concentrate was purified by reverse phase HPLC. $^1$H NMR (DMSO-$d_6$) δ 1.54 (m, 4H), 1.71 (m, 2H), 1.91 (m, 2H), 1.99 (s, 3H), 2.18 (s, 3H), 3.95 (s, 3H), 4.23 (m, 1H), 6.62 (s, 1H), 7.06 (d, J=6 Hz, 1H), 7.51 (m, 2H), 7.98 (s, 1H), 8.15 (d, J=7 Hz, 1H), 8.41 (d, J=9 Hz, 1H), 8.45 (d, J=6 Hz, 1H), 11.40 (s, 1H).

Example 191A

This example was prepared as described in EXAMPLE 12D by substituting methyl 2-(4-aminophenyl)acetate for 3,4,5-trimethoxyphenylamine and EXAMPLE 161A for EXAMPLE 12C. $^1$H NMR (DMSO-$d_6$) δ 10.46 (s, 1H), 9.32 (s, 1H), 8.25-8.31 (m, 2H), 7.67 (dd, J=8.1, 1.4 Hz, 1H), 7.46 (t, J=1.5 Hz, 1H), 7.24 (t, J=8.0 Hz, 1H), 7.17 (bs, 1H), 6.87 (d, J=7.8 Hz, 1H), 3.63 (s, 2H), 3.61 (s, 3H), 1.36 (s, 9H).

Example 191B

To a solution of EXAMPLE 191A (417 mg) in THF/water (15 mL) was added lithium hydroxide (85 mg). The mixture was stirred at ambient temperature for 30 minutes, neutralized with 1M hydrochloric acid and partitioned between ethyl acetate and water. The extract was washed with brine and dried (MgSO$_4$), filtered and concentrated. $^1$H NMR (DMSO-$d_6$) δ 10.38 (bs, 1H), 9.30 (s, 1H), 8.29-8.35 (m, 2H), 7.65 (dd, J=8.0, 1.2 Hz, 1H), 7.46 (t, J=1.7 Hz, 1H), 7.17-7.25 (m, 2H), 6.84-6.88 (m, 1H), 3.50 (s, 2H), 1.37 (s, 9H).

Example 191C

This example was prepared as described in EXAMPLE 187A by substituting EXAMPLE 191B for 4-amino-3-methoxybenzoic acid and 1-methylpiperidin-4-amine for cyclopentylamine. $^1$H NMR (DMSO-$d_6$) δ 10.55 (s, 1H), 9.42 (s, 1H), 8.29 (m, 2H), 8.22 (d, J=7.3 Hz, 1H), 7.59 (d, J=7.9 Hz, 1H), 7.45 (m, 1H), 7.17-7.24 (m, 2H), 6.88 (d, J=7.6 Hz, 1H), 3.71-3.77 (m, 1H), 3.36-3.43 (m, 4H), 2.99-3.12 (m, 2H), 2.75 (d, J=4.6 Hz, 2H), 1.84-1.97 (m, 3H), 1.54-1.62 (m, 2H), 1.35 (s, 9H).

Example 192

This example was prepared as described in EXAMPLE 191C by substituting pyridin-3-ylmethanamine for 1-methylpiperidin-4-amine. $^1$H NMR (DMSO-$d_6$) δ 10.52 (s, 1H), 9.40 (s, 1H), 8.66 (t, J=6.1 Hz, 1H), 8.60 (s, 2H), 8.29 (m, 2H), 7.97 (d, J=7.9 Hz, 1H), 7.59-7.63 (m, 2H), 7.48 (s, 1H), 7.23 (t, J=7.8 Hz, 1H), 7.18 (m, 1H), 6.91 (d, J=7.6 Hz, 1H), 4.36 (d, J=6.1 Hz, 2H), 3.17 (s, 2H), 1.35 (s, 9H).

Example 193A

This example was prepared as described in EXAMPLE 12D by substituting methyl 2-(3-aminophenyl)acetate for 3,4,5-trimethoxyphenylamine and EXAMPLE 161A for EXAMPLE 12C.

Example 193B

This example was prepared as described in EXAMPLE 191C by substituting EXAMPLE 193A for EXAMPLE 191B. $^1$H NMR (DMSO-$d_6$) δ 10.51 (s, 1H), 9.34 (s, 1H), 8.29 (m, 2H), 8.21 (d, J=7.5 Hz, 1H), 7.59 (d, J=8.1 Hz, 1H), 7.46 (m, 1H), 7.16-7.24 (m, 2H), 6.86-6.91 (m, 1H), 3.69-3.76 (m, 1H), 3.40-3.44 (m, 2H), 3.36 (s, 3H), 2.97-3.08 (m, 2H), 2.75 (d, J=4.7 Hz, 2H), 1.82-1.98 (m, 2H), 1.50-1.65 (m, 2H), 1.36 (s, 9H).

Example 194

This example was prepared as described in EXAMPLE 191C by substituting cyclobutylamine for 1-methylpiperidin-4-amine and EXAMPLE 193A for EXAMPLE 191B. $^1$H NMR (DMSO-$d_6$) δ 10.48 (s, 1H), 9.33 (s, 1H), 8.26-8.30 (m, 3H), 7.59 (dd, J=8.0, 1.5 Hz, 1H), 7.42 (m, 1H), 7.16-7.23 (m, 2H), 6.87 (d, J=7.5 Hz, 1H), 4.08-4.22 (m, 1H), 3.17 (s, 2H), 2.07-2.17 (m, 2H), 1.81-1.94 (m, 2H), 1.54-1.66 (m, 2H), 1.36 (s, 9H).

Example 195

A mixture of EXAMPLE 102 (30 mg), 2-ethynylpyridine (19.6 mg), copper(I) iodide (1.2 mg), TEA (45 μL), and 1,1′-bis(diphenylphosphino)ferrocene]dichloropalladium (II) (5.3 mg) in DMF (1.5 mL) was heated at 90° C. for 4 hours, cooled, treated with water and extracted with ethyl acetate. The extract was dried (MgSO$_4$), filtered and concentrated. The concentrate was purified by reverse phase HPLC with acetonitrile/water/0.1% trifluoroacetic acid. $^1$H NMR (DMSO-$d_6$) δ 10.49 (s, 1H), 9.7 (s, 1H), 9.34 (s, 1H), 8.56 (s, 1H), 8.36 (d, J=5.4 Hz, 1H), 8.3 (s, 1H), 7.94-7.98 (m, 1H), 7.81 (d, J=8.8 Hz, 2H), 7.52 (d, J=8.8 Hz, 2H), 7.46 (dd, J=7.6 Hz, 4.9 Hz, 1H), 7.31 (d, J=5.8 Hz, 1H), 1.40 (s, 9H).

Example 196

This example was prepared as described in EXAMPLE 195 by substituting pent-1-yne for 2-ethynylpyridine. $^1$H NMR (CD$_3$OD) δ 8.19 (d, J=6.1 Hz, 1H), 7.52 (d, J=8.54 Hz, 2H), 7.34 (d, J=8.5 Hz, 2H), 7.1 (s, 1H), 2.38 (t, J=6.9 Hz, 2H), 1.59-1.64 (m, 2H), 1.38 (s, 9H), 1.05 (t, J=7.5 Hz, 3H).

Example 197

A mixture of EXAMPLE 102 (60 mg), N,N-diethylprop-2-yn-1-amine (90 µL), copper(I) iodide (1.2 mg), dichlorobis(triphenylphosphine) palladium(II) (9.1 mg) and triphenylphosphine (1.7 mg) in THF (2 mL) was heated at 90° C. for 4 hours, cooled and concentrated. The concentrate was purified by reverse phase HPLC. $^1$H NMR (DMSO-d$_6$) δ 10.55 (s, 1H), 9.83 (s, 1H), 9.7 (s, 1H), 9.35 (d, J=5.5 Hz, 1H), 8.29 (s, 1H), 7.79 (d, J=8.6 Hz, 2H), 7.46 (d, J=8.9 Hz, 2H), 7.26 (d, J=5.5 Hz, 1H), 4.36 (d, J=4.6 Hz, 2H), 3.23-3.28 (m, 4H), 1.37 (s, 9H), 1.26 (t, J=7.2 Hz, 6H).

Example 198

A mixture of EXAMPLE 102 (60 mg), but-3-en-1-ol (13 µL), palladium(II) acetate (1.5 mg), tris-ortho-tolylphosphine (4 mg) and TEA (22 µL) in DMF (2 mL) was heated in a microwave at 110° C. for 10 minutes, cooled, treated with water and extracted with ethyl acetate. The extract was washed with brine and dried (MgSO$_4$), filtered and concentrated. The concentrate was purified by HPLC. $^1$H NMR (DMSO-d$_6$) δ 10.48 (s, 1H), 9.46 (s, 1H), 8.31 (s, 1H), 8.29-8.30 (m, 2H), 7.6 (d, J=8.5 Hz, 2H), 7.31 (d, J=8.5 Hz, 2H), 7.22 (d, J=5.8 Hz, 1H), 6.37 (d, J=15.9 Hz, 1H), 6.13-6.19 (m, 1H), 3.49-3.53 (m, 2H), 2.30-2.34 (m, 2H), 1.37 (s, 1H).

Example 199

This example was prepared as described in EXAMPLE 198 by substituting 2-vinylpyridine for but-3-en-1-ol and triturating the product with methanol. $^1$H NMR (DMSO-d$_6$) δ 10.8 (s, 1H), 9.58 (s, 1H), 8.54 (dd, J=4.9 Hz, 1.5 Hz, 1H), 8.33 (d, J=5.4 Hz, 1H), 8.29 (s, 1H), 7.73-7.76 (m, 3H), 7.58-7.61 (m, 3H), 7.49 (d, J=7.8 Hz, 1H), 7.21 (m, 3H), 1.37 (s, 9H).

Example 200

This example was prepared as described in EXAMPLE 199 by substituting pent-1-ene for 2-vinylpyridine and purifying the product by HPLC. $^1$H NMR (DMSO-d$_6$) δ 10.46 (s, 1H), 9.39 (s, 1H), 8.29-8.30 (m, 2H), 7.62 (d, J=8.6 Hz, 2H), 7.31 (d, J=8.6 Hz, 2H), 7.19 (d, J=5.8 Hz, 1H), 6.34 (d, J=16.0 Hz, 1H), 6.12-6.19 (m, 1H), 2.12-2.19 (m, 2H), 1.42-1.48 (m, 2H), 1.36 (s, 9H), 0.92 (t, J=7.4 Hz, 3H).

Example 201A

A mixture of EXAMPLE 161A (140 mg), 2-methoxy-4-nitroaniline (93 mg), palladium(II) acetate (8.9 mg), 4,5-bis(diphenylphosphino)-9,9-dimethylxanthene (34.7 mg) and cesium carbonate (325.8 mg) in dioxane (3.5 mL) was heated in a microwave at 160° C. for 40 minutes, cooled and filtered. The filtrate was suspended in 5% methanol in dichloromethane/water and filtered.

Example 201B

A mixture of EXAMPLE 201A (800 mg) and tin(II) chloride dihydrate (2.1 mg) in 15:1 DMF/water was stirred at 50° C. for 6.5 hours, treated with sodium bicarbonate and brine, and extracted with ethyl acetate. The extract was washed with water and dried (MgSO$_4$), filtered and concentrated. The concentrate was triturated with methanol. $^1$H NMR (DMSO-d$_6$) δ 10.40 (s, 1H), 8.48 (s, 1H), 8.15 (d, J=5.4 Hz, 1H), 7.66 (s, 1H), 7.34 (d, J=8.1 Hz, 1H), 7.0 (d, J=5.1 Hz, 1H), 6.29 (d, J=2.4 Hz, 1H), 6.14 (dd, J=8.5 Hz, 2.4 Hz, 1H), 4.95 (s, 2H), 3.68 (s, 3H).

Example 201C

A mixture of EXAMPLE 201B (60 mg), HATU (71.6 mg), TEA (26 µL) and cyclopentanecarboxamide (20.4 µL) in DMF was stirred at ambient temperature for 4.3 hours and extracted with ethyl acetate. The concentrate was washed with water and brine and dried (MgSO$_4$), filtered and concentrated. The concentrate was triturated with methanol and purified by HPLC. $^1$H NMR (DMSO-d$_6$) δ 10.58 (s, 1H), 9.85 (s, 1H), 8.46 (s, 1H), 8.25 (d, J=5.4 Hz, 1H), 7.87 (d, J=8.1 Hz, 1H), 7.51 (d, J=2.0 Hz, 1H), 7.10 (dd, J=8.6 Hz, 2.2 Hz, 2H), 3.78 (s, 3H), 2.70-2.81 (m, 1H), 1.80-1.87 (m, 2H), 1.63-1.75 (m, 4H), 1.53-1.58 (m, 2H), 1.43 (s, 9H).

Example 202A

A mixture of 6-aminonicotinic acid (1.0 g) in DMF (43 mL), cyclopentanamine (1.07 mL), HOBt.hydrate (1.46 g), EDCI (2.07 g) and TEA (1.5 mL) in dichloromethane (43 mL) was stirred at ambient temperature for 20 hours and filtered. The filtrate was washed with aqueous sodium bicarbonate and water.

Example 202B

A mixture of EXAMPLE 161A (35 mg), EXAMPLE 202A (28 mg), palladium(II) acetate (2.2 mg), 4,5-bis(diphenylphosphino)-9,9-dimethylxanthene (8.7 mg), and cesium carbonate (81.3 mg) in dioxane (1.5 mL) was heated in a microwave at 160° C. for 40 minutes and purified by reverse phase HPLC with acetonitrile/water/0.1% trifluoroacetic acid. $^1$H NMR (DMSO-d$_6$) δ 10.71 (s, 1H), 8.76 (d, J=2.4 Hz, 1H), 8.45 (d, J=5.8 Hz, 1H), 8.42 (s, 1H), 8.37 (d, J=7.1 Hz, 1H), 8.26 (dd, J=8.8 Hz, 2.03 Hz, 1H), 8.04 (d, J=9.2 Hz, 1H), 7.35 (d, J=9.2 Hz, 1H), 4.2-4.27 (m, 1H), 1.86-1.93 (m, 2H), 1.68-1.72 (m, 2H), 1.53-1.59 (m, 4H), 1.41 (s, 9H).

Example 203A

To a solution of 4-amino-3-fluorobenzoic acid (0.50 g) in THF (40 mL) was added cyclopentanamine (0.478 ml), HOBt.hydrate (0.653), EDCI (0.926 g) and TEA (0.673 mL). The mixture was stirred at ambient temperature for 6 hours and concentrated. The concentrate was treated with water and extracted with ethyl acetate. The extract was washed with aqueous sodium bicarbonate and brine and dried (MgSO$_4$), filtered and concentrated. The concentrate was triturated with ethyl acetate/hexane.

Example 203B

This example was prepared as described in EXAMPLE 202B by substituting EXAMPLE 203A for EXAMPLE 202A. $^1$H NMR (DMSO-d$_6$) δ 10.51 (s, 1H), 9.08 (s, 1H), 8.37 (s, 1H), 8.32 (d, J=5.8 Hz, 1H), 8.25 (d, J=7.1 Hz, 1H), 7.94 (t, J=8.1 Hz, 1H), 7.67-7.76 (m, 2H), 7.28 (d, J=5.8 Hz, 1H), 4.18-4.25 (m, 1H), 1.84-1.93 (m, 2H), 1.66-1.71 (m, 2H), 1.49-1.58 (m, 4H), 1.39 (s, 9H).

Example 204

EXAMPLE 161A (2 g) and 4-aminobenzoic acid (1.5 g) were refluxed in 2,2,2-trifluoroethanol (30 mL) for 24 hours.

The mixture was cooled and filtered. The filtrate was washed with methanol and diethyl ether. $^1$H NMR (DMSO-d$_6$) δ 10.52 (brs, 1H), 9.79 (s, 1H), 8.37 (d, 1H), 8.31 (s, 1H), 7.85 (dd, 4H), 7.30 (d, 1H), 1.68 (s, 9H).

Example 205

A solution of 0.07M EXAMPLE 204 in DMA (0.7 mL) was treated with 0.07M O-(benzotriazol-1-yl)-N,N,N',N'-tetramethyluronium tetrafluoroborate in DMA (0.7 mL), 0.2M (R)-2-amino-2-methyl-pentan-1-ol in DMA (0.3 mL) and 0.2M DIEA in DMA 0.7 mL), shaken at 80° C. for 4 hours, passed through a 1 g Si-Carbonate cartridge with methanol and concentrated. The concentrate was purified by reverse phase HPLC. $^1$H NMR (DMSO-d$_6$) δ 8.33 (d, 1H), 7.83 (d, 2H), 7.71 (d, 2H), 7.27 (br d, 1H), 4.06 (m, 1H), 3.40 (m, 2H), 1.61 (m, 1H), 1.39 (m, 2H), 1.35 (s, 9H), 0.87 (m, 6H).

Example 206

This example was prepared as described in EXAMPLE 205 by substituting (S)-2-amino-4-methylpentanamide for (R)-2-amino-2-methyl-pentan-1-ol. $^1$H NMR (DMSO-d$_6$) δ 8.34 (d, 1H), 7.88 (d, 2H), 7.75 (d, 2H), 7.28 (br d, 1H), 4.45 (m, 1H), 1.66 (m, 2H), 1.56 (m, 1H), 1.35 (s, 9H), 0.90 (dd, 6H).

Example 207

This example was prepared as described in EXAMPLE 205 by substituting (S)-2-amino-2-phenylethanol for (R)-2-amino-2-methyl-pentan-1-ol. $^1$H NMR (DMSO-d$_6$) δ 8.34 (d, 1H), 7.88 (d, 2H), 7.75 (d, 2H), 7.33 (m, 6H), 5.07 (m, 1H), 3.71 (m, 2H), 1.35 (s, 9H).

Example 208

This example was prepared as described in EXAMPLE 205 by substituting 3-ethoxypropan-1-amine for (R)-2-amino-2-methyl-pentan-1-ol. $^1$H NMR (DMSO-d$_6$) δ 8.34 (d, 1H), 7.82 (d, 2H), 7.73 (d, 2H), 7.28 (br d, 1H), 3.42 (m, 4H), 3.31 (t, 2H), 1.76 (m, 2H), 1.35 (s, 9H), 1.11 (t, 3H).

Example 209

This example was prepared as described in EXAMPLE 205 by substituting 3-(methylthio)propan-1-amine for (R)-2-amino-2-methyl-pentan-1-ol. $^1$H NMR (DMSO-d$_6$) δ 8.34 (d, 1H), 7.82 (d, 2H), 7.74 (d, 2H), 7.27 (br d, 1H), 3.34 (t, 2H), 2.51 (t, 2H), 2.06 (s, 3H), 1.79 (m, 2H), 1.35 (s, 9H).

Example 210

This example was prepared as described in EXAMPLE 205 by substituting. N$^1$,N$^1$-dimethylbutane-1,4-diamine for (R)-2-amino-2-methyl-pentan-1-ol. $^1$H NMR (DMSO-d$_6$) δ 8.34 (d, 1H), 7.78 (dd, 4H), 7.24 (br d, 1H), 3.30 (t, 2H), 3.08 (t, 2H), 2.78 (s, 3H), 1.65 (m, 2H), 1.57 (m, 2H), 1.36 (s, 9H).

Example 211

This example was prepared as described in EXAMPLE 205 by substituting 2-phenoxyethanamine for (R)-2-amino-2-methyl-pentan-1-ol. $^1$H NMR (DMSO-d$_6$) δ 8.34 (d, 1H), 7.85 (d, 2H), 7.74 (d, 2H), 7.30 (m, 3H), 6.96 (m, 3H), 4.11 (t, 2H), 3.64 (t, 2H), 1.35 (s, 9H).

Example 212

This example was prepared as described in EXAMPLE 205 by substituting 1-(3-aminopropyl)pyrrolidin-2-one for (R)-2-amino-2-methyl-pentan-1-ol. $^1$H NMR (DMSO-d$_6$) δ 8.34 (d, 1H), 7.82 (d, 2H), 7.75 (d, 2H), 7.29 (br d, 1H), 3.37 (t, 2H), 3.34 (m, 4H), 2.26 (t, 2H), 1.94 (m, 2H), 1.71 (m, 2H), 1.36 (s, 9H).

Example 213

This example was prepared as described in EXAMPLE 205 by substituting 2-(5-methoxy-1H-indol-3-yl)ethanamine for (R)-2-amino-2-methyl-pentan-1-ol. $^1$H NMR (DMSO-d$_6$) δ 8.34 (d, 1H), 7.78 (dd, 4H), 7.25 (d, 2H), 7.14 (s, 1H), 7.07 (d, 1H), 6.73 (dd, 1H), 3.53 (t, 2H), 2.93 (t, 2H), 1.37 (s, 9H).

Example 214

This example was prepared as described in EXAMPLE 205 by substituting (3,4-difluorophenyl)methanamine for (R)-2-amino-2-methyl-pentan-1-ol. $^1$H NMR (DMSO-d$_6$) δ 8.34 (d, 1H), 7.86 (d, 2H), 7.76 (d, 2H), 7.27 (m, 4H), 4.45 (s, 2H), 1.35 (s, 9H).

Example 215

This example was prepared as described in EXAMPLE 205 by substituting (S)-1-(naphthalen-1-yl)ethanamine for (R)-2-amino-2-methyl-pentan-1-ol. $^1$H NMR (DMSO-d$_6$) δ 8.34 (d, 1H), 8.20 (d, 1H), 7.95 (d, 1H), 7.87 (d, 2H), 7.84 (d, 1H), 7.75 (d, 2H), 7.57 (m, 4H), 7.22 (br d, 1H), 5.95 (m, 1H), 1.62 (d, 3H), 1.35 (s, 9H).

Example 216

This example was prepared as described in EXAMPLE 205 by substituting 4-(2-aminoethyl)benzenesulfonamide for (R)-2-amino-2-methyl-pentan-1-ol. $^1$H NMR (DMSO-d$_6$) δ 8.34 (d, 1H), 7.76 (m, 6H), 7.45 (d, 2H), 7.26 (br d, 1H), 3.53 (t, 2H), 2.94 (t, 2H), 1.36 (s, 9H).

Example 217

A solution of 0.06M EXAMPLE 204 in DMA (0.8 mL) was treated with 0.06M O-(benzotriazol-1-yl)-N,N,N',N'-tetramethyluronium tetrafluoroborate in DMA (0.8 mL), 0.2M pyridin-2-ylmethanamine in DMA (0.3 mL), and 0.2M DIEA in DMA (0.8 mL), shaken at 80° C. for 4 hours, passed through a 1 g Si-Carbonate cartridge with methanol and concentrated. The concentrate was purified by reverse phase HPLC. $^1$H NMR (DMSO-d$_6$) δ 8.7 (d, 1H), 8.40 (td, 1H), 8.35 (d, 1H), 7.87 (m, 6H), 7.25 (br d, 1H), 4.78 (s, 2H), 1.37 (s, 9H).

Example 218

This example was prepared as described in EXAMPLE 217 by substituting 2-(1H-imidazol-4-yl)ethanamine for pyridin-2-ylmethanamine. $^1$H NMR (DMSO-d$_6$) δ 8.93 (d, 1H), 8.34 (d, 1H), 7.76 (m, 4H), 7.41 (s, 1H), 7.22 (br d, 1H), 3.57 (t, 2H), 2.93 (t, 2H), 1.35 (s, 9H).

Example 219

This example was prepared as described in EXAMPLE 217 by substituting 2-morpholinoethanamine for pyridin-2- ylmethanamine. ¹H NMR (DMSO-d₆) δ 8.35 (d, 1H), 7.81 (m, 4H), 7.24 (br d, 1H), 4.00 (m, 2H), 3.66 (m, 4H), 3.54 (m, 2H), 3.32 (t, 2H), 3.15 (m, 2H), 1.37 (s, 9H).

Example 220

EXAMPLE 161A (3.02 g) and 4-amino-3-methoxybenzoic acid (2.7 g) were refluxed in 2,2,2-trifluoroethanol (30 mL) for 24 hours. The mixture was cooled and filtered, and the filtrate was washed with methanol and diethyl ether. ¹H NMR (DMSO-d₆) δ 10.70 (brs, 1H), 8.44 (d, 1H), 8.42 (s, 1H), 8.37 (d, 1H), 7.98 (s, 1H), 7.59 (dd, 1H), 7.52 (d, 1H), 7.19 (d, 1H), 3.93 (s, 3H), 1.45 (s, 9H).

Example 221

A solution of EXAMPLE 220 (99 mg), HATU (119 mg) and diisopropylethylamine (0.08 mL) in DMF (1 mL) was stirred at ambient temperature for 0.5 hours. $N^1,N^1$-dimethylcyclohexane-1,4-diamine (44 mg) was added, and the mixture was stirred for 24 hours and concentrated. The concentrate was purified by reverse phase HPLC with acetonitrile/water/0.1% trifluoroacetic acid. ¹H NMR (DMSO-d₆) δ 10.80 (brs, 1H), 9.45 (brs, 1H), 8.32 (m, 4H), 7.50 (m, 2H), 7.18 (br d, 1H), 3.93 (d, 3H), 3.18 (m, 1H), 2.76 (d, 6H), 2.02 (m, 3H), 1.81 (m, 3H), 1.59 (m, 3H), 1.43 (s, 9H).

Example 222

This example was prepared as described in EXAMPLE 221 by substituting 2-methyl-1-morpholinopropan-2-amine for $N^1,N^1$-dimethylcyclohexane-1,4-diamine. ¹H NMR (DMSO-d₆) δ 10.78 (brs, 1H), 8.36 (m, 3H), 8.14 (d, 1H), 8.06 (d, 1H), 7.53 (m, 2H), 7.16 (br d, 1H), 3.93 (m, 5H), 3.80 (m, 2H), 3.67 (m, 2H), 3.48 (m, 2H), 3.20 (m, 2H), 1.50 (s, 6H), 1.44 (s, 9H).

Example 223

This example was prepared as described in EXAMPLE 221 by substituting 1-ethylpiperidin-3-amine for $N^1,N^1$-dimethylcyclohexane-1,4-diamine. ¹H NMR (DMSO-d₆) δ 10.82 (brs, 1H), 9.58 (brs, 1H), 8.46 (m, 2H), 8.38 (m, 2H), 8.10 (brs, 1H), 7.52 (m, 1H), 7.18 (m, 1H), 3.93 (s, 3H), 3.51 (m, 2H), 3.17 (m, 2H), 2.74 (m, 2H), 1.96 (m, 2H), 1.71 (m, 3H), 1.44 (s, 9H), 1.24 (t, 3H).

Example 224

A mixture of EXAMPLE 161A (511 mg) and 4-amino-3-(trifluoromethoxy)benzoic acid (610 mg) in 2,2,2-trifluoroethanol (20 mL) was refluxed for 24 hours, cooled and chromatographed by reverse phase HPLC with acetonitrile/water/0.1% trifluoroacetic acid. ¹H NMR (DMSO-d₆) δ 10.62 (brs, 1H), 9.20 (brs, 1H), 8.38 (d, 1H), 8.28 (brs, 1H), 8.22 (d, 1H), 7.91 (dd, 1H), 7.84 (m, 1H), 7.36 (br d, 1H), 1.36 (s, 9H).

Example 225

This example was prepared as described in EXAMPLE 221 by substituting EXAMPLE 224 (21 mg) for EXAMPLE 220 and cyclobutylamine (8 mg) for $N^1,N^1$-dimethylcyclohexane-1,4-diamine. ¹H NMR (DMSO-d₆) δ 10.61 (brs, 1H), 9.17 (s, 1H), 8.69 (d, 1H), 8.34 (m, 2H), 8.08 (d, 1H), 7.90 (m, 2H), 7.35 (br d, 1H), 4.42 (m, 1H), 2.23 (m, 2H), 2.06 (m, 2H), 1.68 (m, 2H), 1.36 (s, 9H).

Example 226A

A mixture of 2,6-dichloro-9H-purine (0.567 g), benzyl bromide (1.03 g) and potassium carbonate (1.38 g) in DMF (10 mL) at ambient temperature was stirred overnight and partitioned between ethyl acetate and water. The extract was washed with brine and dried (MgSO₄), filtered, and concentrated. The concentrate was purified by flash chromatography on silica gel with 2:3 ethyl acetate/hexane. ¹H NMR (DMSO-d₆) δ 8.86 (s, 1H), 7.31-7.37 (m, 5H), 5.51 (s, 2H).

Example 226B

A mixture of EXAMPLE 226A (0.280 g), 3-amino-4-(tert-butylamino)cyclobut-3-ene-1,2-dione (0.170 g) and potassium carbonate (0.138 g) in 2-propanol (10 mL) was heated at reflux for 2 hours, cooled and concentrated. The concentrate was partitioned between ethyl acetate and water, and the extract was separated, washed with brine and dried (MgSO₄), filtered, and concentrated. The concentrate was purified by flash chromatography on silica gel with 2:3 ethyl acetate/hexane. ¹H NMR (DMSO-d₆) δ 11.71 (s, 1H), 8.60 (s, 1H), 8.56 (s, 1H), 7.39-7.39 (m, 5H), 5.44 (s, 2H), 1.47 (s, 9H).

Example 226C

A mixture of EXAMPLE 226B (0.082 g), 4-amino-N-cyclobutyl-3-methoxybenzamide (0.049 g), palladium(II) acetate (4.5 mg), 9,9-dimethyl-4,5-bis(diphenylphosphino)xanthene (17.4 mg) and cesium carbonate (0.078 g) in dioxane (2 mL) was heated under microwave conditions at 150° C. for 10 minutes. The mixture was flash chromatographed on silica gel with 100:1 ethyl acetate/methanol. ¹H NMR (DMSO-d₆) δ 11.11 (s, 1H), 8.56 (d, J=8.2 Hz, 1H), 8.48 (d, J=7.3 Hz, 1H), 8.38 (s, 1H), 8.31 (s, 1H), 7.79 (s, 1H), 7.49-7.54 (m, 2H), 7.38-7.44 (m, 4H), 7.30-7.33 (m, 1H), 5.43 (s, 2H), 4.41-4.44 (m, 1H), 3.94 (s, 3H), 2.21-2.25 (m, 2H), 2.06-2.12 (m, 2H), 1.66-1.71 (m, 2H), 1.45 (s, 9H).

Example 226D

A mixture of EXAMPLE 226C (45 mg), 10% palladium on carbon (10 mg) and palladium(II) chloride (10 mg) in 37% hydrochloric acid (0.5 mL) and methanol (5 mL) was stirred overnight under 1 atmosphere of hydrogen, filtered and concentrated. The concentrate was purified by reverse phase HPLC on a $C_{18}$ column with acetonitrile/water/0.1% trifluoroacetic acid. ¹H NMR (DMSO-d₆) δ 11.06 (s, 1H), 8.61 (d, J=8.9 Hz, 1H), 8.47 (d, J=7.7 Hz, 1H), 8.43 (s, 1H), 8.24 (s, 1H), 7.76 (s, 1H), 7.50-7.52 (m, 2H), 2.19-2.28 (m, 2H), 2.06-2.11 (m, 2H), 1.63-1.72 (m, 2H), 1.47 (s, 9H).

The foregoing is meant to illustrate the invention but not to limit it. Variations and changes obvious to one skilled in the art are intended to be within the scope of the invention as defined in the claims.

We claim:
1. A compound having formula (I)

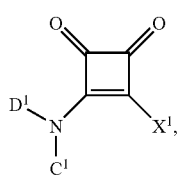

(I)

or a therapeutically acceptable salt thereof, wherein
$X^1$ is $N(A^1)(B^1)$;
$A^1$ is $R^1$;
$B^1$ is H;
$R^1$ is $R^2$, $R^4$ or $R^5$;
$R^2$ is phenyl;

R⁴ is cycloalkyl, cycloalkenyl, heterocycloalkyl or heterocycloalkenyl;

R⁵ is alkyl, alkenyl or alkynyl, each of which is unsubstituted or substituted with one, two or three of independently selected R⁶, OR⁶, C(O)OR⁶, C(O)NH₂, C(O) NHR⁶, C(O)N(R⁶)₂, NHC(O)R⁶, NR⁶C(O)R⁶, OH, (O), CN, NH₂, NHR⁶, N(R⁶)₂, F, Cl, Br or I;

R⁶ is R⁷ or R⁹;

R⁷ is phenyl;

R⁹ cycloalkyl or heterocycloalkyl;

C¹ is H;

D¹ is R¹⁸ or R²⁰;

R¹⁸ is pyrimidinyl which is substituted with NHR²¹ or N(CH₃)R²¹; and optionally substituted with one or two of CN, NO₂, F, Cl, Br, or I;

R²⁰ is furanyl, imidazolyl, isothiazolyl, isoxazolyl, 1,2,3-oxadiazoyl, 1,2,5-oxadiazoyl, oxazolyl, pyrazinyl, pyrazolyl, pyridazinyl, pyrrolyl, 1,2,4-thiadiazolyl, thiazolyl, thiophenyl, triazinyl or 1,2,3-triazolyl, each of which is substituted with NHR²¹ or N(CH₃)R²¹;

R²¹ is R²² or R²³;

R²² is phenyl which is unfused or fused with benzene or R²²ᴬ; R²²ᴬ is cycloalkyl or heterocycloalkyl;

R²³ is heteroaryl;

wherein R²² and R²³ are independently unsubstituted or substituted with one, two, three, four or five of independently selected R³⁰, OR³⁰, SR³⁰, S(O)R³⁰, SO₂R³⁰, C(O)R³⁰, CO(O)R³⁰, OC(O)R³⁰, OC(O)OR³⁰, NH₂, NHR³⁰, N(R³⁰)₂, C(O)NH₂, C(O)NHR³⁰, C(O)N (R³⁰)₂, SO₂NH₂, SO₂NHR³⁰, NHSO₂R³⁰, N(R³⁰) SO₂R³⁰, SO₂N(R³⁰)₂, CF₃, CF₂CF₃, C(O)H, CN, C(O) OH, (O), OH, NO₂, CF₃, CF₂CF₃, OCF₃, OCF₂CF₃, F, Cl, Br or I;

R³¹ is R³¹, R³², R³³ or R³⁴;

R³¹ is phenyl;

R³² is heteroaryl;

R³³ is cycloalkyl, cycloalkenyl, heterocycloalkyl or heterocloalkenyl;

R³⁴ is alkyl, alkenyl or alkynyl, each of which is unsubstituted or substituted with one, two or three of independently selected R³⁵, OR³⁵, SR³⁵, C(O)OR³⁵, NH₂, NHR³⁵, OH, N(R³⁵)₂, C(O)NH₂, C(O)NHR³⁵, C(O)N (R³⁵)₂, NHC(O)R³⁵, N(R³⁵)C(O)R³⁵, F, Cl, Br or I;

R³⁵ is R³⁶, R³⁷, R³⁸ or R³⁹;

R³⁶ is phenyl;

R³⁷ is heteroaryl;

R³⁸ is cycloalkyl, cycloalkenyl, heterocycloalkyl or heterocloalkenyl;

the moieties represented by R³¹, R³², R³³, R³⁶, R³⁷, and R³⁸ are independently unsubstituted or substituted with one, two, three, four or five of independently substituted R³⁹, OR³⁹, C(O)OR³⁹, NH₂, NHR³⁹, N(R³⁹)₂, C(O) NH₂, C(O)NHR³⁹, C(O)N(R³⁹)₂, NHC(O)R³⁹, N(R³⁹) C(O)R³⁹, SO₂NH₂, SO₂NHR³⁹, SO₂N(R³⁹)₂, (O), CN, F, Cl, Br or I; and R³⁹ is alkyl.

2. The compound of claim 1 wherein

A¹ is R¹;

B¹ is H;

R¹ is R², R⁴ or R⁵;

R² is phenyl;

R⁴ is cycloalkyl or heterocycloalkyl;

R⁵ is alkyl, which is unsubstituted or substituted with one, two or three of independently selected R⁶, OH, (O), CN, NH₂, NHR⁶, N(R⁶)₂, F, Cl, Br or I;

R⁶ is R⁷ or R⁹;

R⁷ is phenyl;

R⁹ is cycloalkyl;

D¹ is R¹⁸;

R¹⁸ is pyrimidinyl which is substituted with NHR²¹ or N(CH₃)R²¹;

R²¹ is R²²; and

R²² is phenyl.

3. A compound of claim 2 wherein

X¹ is N(A¹)(B¹);

A¹ is R¹;

R¹ is R⁵; and

R⁵ is alkyl, which is unsubstituted.

4. A composition comprising an excipient and a therapeutically effective amount of a compound of claim 1.

5. The compound of claim 1 selected from the group consisting of 3-({2-[(3,4,5-trimethoxyphenyl)amino]pyrimidin-4-yl}amino)-4-{[(1R)-1,2,2-trimethylpropyl]amino}cyclobut-3-ene-1,2-dione;

3-[(2-{[4-(trifluoromethoxy)phenyl]amino}pyrimidin-4-yl)amino]-4-{[(1R)-1,2,2-trimethylpropyl]amino}cyclobut-3-ene-1,2-dione;

3-({2-[(3-methylphenyl)amino]pyrimidin-4-yl}amino)-4-{[(1R)-1,2,2-trimethylpropyl]amino}cyclobut-3-ene-1,2-dione;

3-({2-[(4-fluorophenyl)amino]pyrimidin-4-yl}amino)-4-{[(1R)-1,2,2-trimethylpropyl]amino}cyclobut-3-ene-1,2-dione;

3-({2-[(2-isopropylphenyl)amino]pyrimidin-4-yl}amino)-4-{[(1R)-1,2,2-trimethylpropyl]amino}cyclobut-3-ene-1,2-dione;

3-({2-[(4-chlorophenyl)amino]pyrimidin-4-yl}amino)-4-{[(1R)-1,2,2-trimethylpropyl]amino}cyclobut-3-ene-1,2-dione;

3-{[2-(2-naphthylamino)pyrimidin-4-yl]amino}-4-{[(1R)-1,2,2-trimethylpropyl]amino}cyclobut-3-ene-1,2-dione;

3-({2-[(3-bromo-4-methylphenyl)amino]pyrimidin-4-yl}amino)-4-{[(1R)-1,2,2-trimethylpropyl]amino}cyclobut-3-ene-1,2-dione;

3-{[2-(1,1'-biphenyl-4-ylamino)pyrimidin-4-yl]amino}-4-{[(1R)-1,2,2-trimethylpropyl]amino}cyclobut-3-ene-1,2-dione;

3-({2-[(4-phenoxyphenyl)amino]pyrimidin-4-yl}amino)-4-{[(1R)-1,2,2-trimethylpropyl]amino}cyclobut-3-ene-1,2-dione;

3-({2-[(3-phenoxyphenyl)amino]pyrimidin-4-yl}amino)-4-{[(1R)-1,2,2-trimethylpropyl]amino}cyclobut-3-ene-1,2-dione;

3-({2-[(2,3-dimethoxyphenyl)amino]pyrimidin-4-yl}amino)-4-{[(1R)-1,2,2-trimethylpropyl]amino}cyclobut-3-ene-1,2-dione;

3-{[2-(2,3-dihydro-1,4-benzodioxin-6-ylamino)pyrimidin-4-yl]amino}-4-{[(1R)-1,2,2-trimethylpropyl]amino}cyclobut-3-ene-1,2-dione;

3-{[2-(1-naphthylamino)pyrimidin-4-yl]amino}-4-{[(1R)-1,2,2-trimethylpropyl]amino}cyclobut-3-ene-1,2-dione;

3-({2-[(2,4-dimethoxyphenyl)amino]pyrimidin-4-yl}amino)-4-{[(1R)-1,2,2-trimethylpropyl]amino}cyclobut-3-ene-1,2-dione;

3-({2-[(2,5-dimethoxyphenyl)amino]pyrimidin-4-yl}amino)-4-{[(1R)-1,2,2-trimethylpropyl]amino}cyclobut-3-ene-1,2-dione;

3-{[2-(1,1'-biphenyl-3-ylamino)pyrimidin-4-yl]amino}-4-{[(1R)-1,2,2-trimethylpropyl]amino}cyclobut-3-ene-1,2-dione;

3-({2-[(4-methoxyphenyl)amino]pyrimidin-4-yl}amino)-4-{[(1R)-1,2,2-trimethylpropyl]amino}cyclobut-3-ene-1,2-dione;

3-({2-[(3-chlorophenyl)amino]pyrimidin-4-yl}amino)-4-{[(1R)-1,2,2-trimethylpropyl]amino}cyclobut-3-ene-1,2-dione;

3-({2-[(3-bromophenyl)amino]pyrimidin-4-yl}amino)-4-{[(1R)-1,2,2-trimethylpropyl]amino}cyclobut-3-ene-1,2-dione;

3-({2-[(3-isopropoxyphenyl)amino]pyrimidin-4-yl}amino)-4-{[(1R)-1,2,2-trimethylpropyl]amino}cyclobut-3-ene-1,2-dione;

3-({2-[(4-morpholin-4-ylphenyl)amino]pyrimidin-4-yl}amino)-4-{[(1R)-1,2,2-trimethylpropyl]amino}cyclobut-3-ene-1,2-dione;

3-({2-[(3-ethynylphenyl)amino]pyrimidin-4-yl}amino)-4-{[(1R)-1,2,2-trimethylpropyl]amino}cyclobut-3-ene-1,2-dione;

3-({2-[(3,4-difluorophenyl)amino]pyrimidin-4-yl}amino)-4-{[(1R)-1,2,2-trimethylpropyl]amino}cyclobut-3-ene-1,2-dione;

3-({2-[(3-chloro-4-fluorophenyl)amino]pyrimidin-4-yl}amino)-4-{[(1R)-1,2,2-trimethylpropyl]amino}cyclobut-3-ene-1,2-dione;

3-[(2-{[3-(trifluoromethyl)phenyl]amino}pyrimidin-4-yl)amino]-4-{[(1R)-1,2,2-trimethylpropyl]amino}cyclobut-3-ene-1,2-dione;

4'-({4-[(3,4-dioxo-2-{[(1R)-1,2,2-trimethylpropyl]amino}cyclobut-1-en-1-yl)amino]pyrimidin-2-yl}amino)-1,1'-biphenyl-4-carbonitrile;

3-({2-[(2'-methoxy-1,1'-biphenyl-4-yl)amino]pyrimidin-4-yl}amino)-4-{[(1R)-1,2,2-trimethylpropyl]amino}cyclobut-3-ene-1,2-dione;

3-[(2-{[4-(1H-imidazol-1-yl)phenyl]amino}pyrimidin-4-yl)amino]-4-{[(1R)-1,2,2-trimethylpropyl]amino}cyclobut-3-ene-1,2-dione;

3-({2-[(4'-methoxy-1,1'-biphenyl-4-yl)amino]pyrimidin-4-yl}amino)-4-{[(1R)-1,2,2-trimethylpropyl]amino}cyclobut-3-ene-1,2-dione;

3-[(2-{[4-(dimethylamino)phenyl]amino}pyrimidin-4-yl)amino]-4-{[(1R)-1,2,2-trimethylpropyl]amino}cyclobut-3-ene-1,2-dione;

3-({2-[(4-methoxyphenyl)(methyl)amino]pyrimidin-4-yl}amino)-4-{[(1R)-1,2,2-trimethylpropyl]amino}cyclobut-3-ene-1,2-dione;

3-({2-[(4'-chloro-1,1'-biphenyl-4-yl)amino]pyrimidin-4-yl}amino)-4-{[(1R)-1,2,2-trimethylpropyl]amino}cyclobut-3-ene-1,2-dione;

3-[(2-{[4-(1,2,3-thiadiazol-4-yl)phenyl]amino}pyrimidin-4-yl)amino]-4-{[(1R)-1,2,2-trimethylpropyl]amino}cyclobut-3-ene-1,2-dione;

3-({2-[(4-thien-2-ylphenyl)amino]pyrimidin-4-yl}amino)-4-{[(1R)-1,2,2-trimethylpropyl]amino}cyclobut-3-ene-1,2-dione;

3-{[2-(1,3-benzothiazol-6-yl)pyrimidin-4-yl]amino}-4-{[(1R)-1,2,2-trimethylpropyl]amino}cyclobut-3-ene-1,2-dione;

3-(tert-butylamino)-4-({2-[(4-fluoro-3-methylphenyl)amino]pyrimidin-4-yl}amino)cyclobut-3-ene-1,2-dione;

3-{[2-(1,3-benzothiazol-6-ylamino)pyrimidin-4-yl]amino}-4-(tert-butylamino)cyclobut-3-ene-1,2-dione;

3-(tert-butylamino)-4-[(2-{[4-(1,2,3-thiadiazol-4-yl)phenyl]amino}pyrimidin-4-yl)amino]cyclobut-3-ene-1,2-dione;

3-(tert-butylamino)-4-[(2-{[4-(4-methylpiperazin-1-yl)phenyl]amino}pyrimidin-4-yl)amino]cyclobut-3-ene-1,2-dione;

3-(tert-butylamino)-4-({2-[(4-hydroxy-3-methylphenyl)amino]pyrimidin-4-yl}amino)cyclobut-3-ene-1,2-dione;

3-(tert-butylamino)-4-{[2-(2,3-dihydro-1H-inden-5-ylamino)pyrimidin-4-yl]amino}cyclobut-3-ene-1,2-dione;

3-(tert-butylamino)-4-({2-[(4-morpholin-4-ylphenyl)amino]pyrimidin-4-yl}amino)cyclobut-3-ene-1,2-dione;

3-(tert-butylamino)-4-[(2-{[4-(morpholin-4-ylmethyl)phenyl]amino}pyrimidin-4-yl)amino]cyclobut-3-ene-1,2-dione;

3-(tert-butylamino)-4-{[2-(2-naphthylamino)pyrimidin-4-yl]amino}cyclobut-3-ene-1,2-dione;

3-{[2-(1-benzothien-5-ylamino)pyrimidin-4-yl]amino}-4-(tert-butylamino)cyclobut-3-ene-1,2-dione;

3-(tert-butylamino)-4-{[2-(2,3-dihydro-1-benzofuran-5-ylamino)pyrimidin-4-yl]amino}cyclobut-3-ene-1,2-dione;

3-{[2-(1-benzofuran-5-ylamino)pyrimidin-4-yl]amino}-4-(tert-butylamino)cyclobut-3-ene-1,2-dione;

3-(tert-butylamino)-4-{[2-(1H-indol-5-ylamino)pyrimidin-4-yl]amino}cyclobut-3-ene-1,2-dione;

3-(tert-butylamino)-4-{[2-(1H-indazol-5-ylamino)pyrimidin-4-yl]amino}cyclobut-3-ene-1,2-dione;

3-(tert-butylamino)-4-({2-[(1-methyl-1H-indazol-5-yl)amino]pyrimidin-4-yl}amino)cyclobut-3-ene-1,2-dione;

3-(tert-butylamino)-4-[(2-{[4-(1H-pyrrol-1-yl)phenyl]amino}pyrimidin-4-yl)amino]cyclobut-3-ene-1,2-dione;

3-(tert-butylamino)-4-[(2-{[4-(1H-pyrazol-1-yl)phenyl]amino}pyrimidin-4-yl)amino]cyclobut-3-ene-1,2-dione;

3-(tert-butylamino)-4-[(2-{[4-(4,6-dimethoxypyrimidin-2-yl)phenyl]amino}pyrimidin-4-yl)amino]cyclobut-3-ene-1,2-dione;

3-({2-[(1-acetyl-2,3-dihydro-1H-indol-5-yl)amino]pyrimidin-4-yl}amino)-4-(tert-butylamino)cyclobut-3-ene-1,2-dione;

3-(tert-butylamino)-4-{[2-(2,3-dihydro-1H-indol-5-ylamino)pyrimidin-4-yl]amino}cyclobut-3-ene-1,2-dione;

3-{[2-(1,3-benzothiazol-5-ylamino)pyrimidin-4-yl]amino}-4-(tert-butylamino)cyclobut-3-ene-1,2-dione;

3-({2-[(4-phenyl-1,3-thiazol-2-yl)amino]pyrimidin-4-yl}amino)-4-{[(1R)-1,2,2-trimethylpropyl]amino}cyclobut-3-ene-1,2-dione;

3-(tert-butylamino)-4-({2-[(4-phenyl-1,3-thiazol-2-yl)amino]pyrimidin-4-yl}amino)cyclobut-3-ene-1,2-dione;

3-{[2-(1,1'-biphenyl-4-ylamino)pyrimidin-4-yl]amino}-4-(tert-butylamino)cyclobut-3-ene-1,2-dione;

3-{[2-(1,1'-biphenyl-4-ylamino)pyrimidin-4-yl]amino}-4-(neopentylamino)cyclobut-3-ene-1,2-dione;

3-{[2-(1,1'-biphenyl-4-ylamino)pyrimidin-4-yl]amino}-4-[(cyclopropylmethyl)amino]cyclobut-3-ene-1,2-dione;

3-{[2-(1,1'-biphenyl-4-ylamino)pyrimidin-4-yl]amino}-4-[(2-morpholin-4-ylethyl)amino]cyclobut-3-ene-1,2-dione;

3-{[2-(1,1'-biphenyl-4-ylamino)pyrimidin-4-yl]amino}-4-[(1,3-dimethylbutyl)amino]cyclobut-3-ene-1,2-dione;

3-{[2-(1,1'-biphenyl-4-ylamino)pyrimidin-4-yl]amino}-4-[(1,2-dimethylpropyl)amino]cyclobut-3-ene-1,2-dione;

3-{[2-(1,1'-biphenyl-4-ylamino)pyrimidin-4-yl]amino}-4-[(1-phenylethyl)amino]cyclobut-3-ene-1,2-dione;

3-{[2-(1,1'-biphenyl-4-ylamino)pyrimidin-4-yl]amino}-4-{[(1S)-1,2,2-trimethylpropyl]amino}cyclobut-3-ene-1,2-dione;

3-{[2-(1,1'-biphenyl-4-ylamino)pyrimidin-4-yl]amino}-4-[(1,1-dimethylpropyl)amino]cyclobut-3-ene-1,2-dione;

3-({4-[(3,4,5-trimethoxyphenyl)amino]-1,3,5-triazin-2-yl}amino)-4-{[(1R)-1,2,2-trimethylpropyl]amino}cyclobut-3-ene-1,2-dione;

4-({3,4-dioxo-2-[(1-phenylethyl)amino]cyclobut-1-en-1-yl}amino)-2-[(3,4,5-trimethoxyphenyl)amino]pyrimidine-5-carbonitrile;

4-[(3,4-dioxo-2-{[(1S)-1,2,2-trimethylpropyl]amino}cyclobut-1-en-1-yl)amino]-2-[(3,4,5-trimethoxyphenyl)amino]pyrimidine-5-carbonitrile;

4-({2-[(1,2-dimethylpropyl)amino]-3,4-dioxocyclobut-1-en-1-yl}amino)-2-[(3,4,5-trimethoxyphenyl)amino]pyrimidine-5-carbonitrile;

3-{[3-(1,1'-biphenyl-4-ylamino)-1,2,4-thiadiazol-5-yl]amino}-4-{[(1R)-1,2,2-trimethylpropyl]amino}cyclobut-3-ene-1,2-dione;

3-{[3-(1,1'-biphenyl-4-ylamino)-1,2,4-thiadiazol-5-yl]amino}-4-{[(1S)-1,2,2-trimethylpropyl]amino}cyclobut-3-ene-1,2-dione;

3-(tert-butylamino)-4-({2-[(4-iodophenyl)amino]pyrimidin-4-yl}amino)cyclobut-3-ene-1,2-dione;

3-(tert-butylamino)-4-({2-[(4-pyridin-4-ylphenyl)amino]pyrimidin-4-yl}amino)cyclobut-3-ene-1,2-dione;

3-(tert-butylamino)-4-({2-[(4-pyridin-3-ylphenyl)amino]pyrimidin-4-yl}amino)cyclobut-3-ene-1,2-dione;

3-(tert-butylamino)-4-[(2-{[4-(1H-pyrazol-4-yl)phenyl]amino}pyrimidin-4-yl)amino]cyclobut-3-ene-1,2-dione;

3-(tert-butylamino)-4-({2-[(4-pyrimidin-5-ylphenyl)amino]pyrimidin-4-yl}amino)cyclobut-3-ene-1,2-dione;

3-(tert-butylamino)-4-[(2-{[4-(2,4-dimethoxypyrimidin-5-yl)phenyl]amino}pyrimidin-4-yl)amino]cyclobut-3-ene-1,2-dione;

3-(tert-butylamino)-4-[(2-{[4-(2-methoxypyrimidin-5-yl)phenyl]amino}pyrimidin-4-yl)amino]cyclobut-3-ene-1,2-dione;

3-(tert-butylamino)-4-[(5-fluoro-2-{[4-(1,2,3-thiadiazol-4-yl)phenyl]amino}pyrimidin-4-yl)amino]cyclobut-3-ene-1,2-dione;

3-(tert-butylamino)-4-[(2-{[4-(1H-1,2,4-triazol-1-yl)phenyl]amino}pyrimidin-4-yl)amino]cyclobut-3-ene-1,2-dione;

3-(tert-butylamino)-4-[(2-{[4-(1H-pyrazol-5-yl)phenyl]amino}pyrimidin-4-yl)amino]cyclobut-3-ene-1,2-dione;

3-{[2-(1H-1,2,3-benzotriazol-5-ylamino)pyrimidin-4-yl]amino}-4-(tert-butylamino)cyclobut-3-ene-1,2-dione;

3-(tert-butylamino)-4-({2-[(4-thien-3-ylphenyl)amino]pyrimidin-4-yl}amino)cyclobut-3-ene-1,2-dione;

3-{[2-(1H-benzimidazol-5-ylamino)pyrimidin-4-yl]amino}-4-(tert-butylamino)cyclobut-3-ene-1,2-dione;

3-({2-[(1-acetyl-2,3-dihydro-1H-indol-6-yl)amino]pyrimidin-4-yl}amino)-4-(tert-butylamino)cyclobut-3-ene-1,2-dione;

N-{3-[(4-{[2-(tert-butylamino)-3,4-dioxocyclobut-1-en-1-yl]amino}pyrimidin-2-yl)amino]phenyl}methanesulfonamide;

3-(tert-butylamino)-4-[(2-{[2-(trifluoromethyl)-1H-benzimidazol-5-yl]amino}pyrimidin-4-yl)amino]cyclobut-3-ene-1,2-dione;

N-{4-[(4-{[2-(tert-butylamino)-3,4-dioxocyclobut-1-en-1-yl]amino}pyrimidin-2-yl)amino]phenyl}-4-methylbenzenesulfonamide;

3-(tert-butylamino)-4-({2-[(2-methyl-1,3-benzothiazol-5-yl)amino]pyrimidin-4-yl}amino)cyclobut-3-ene-1,2-dione;

3-(tert-butylamino)-4-[(2-{[4-(morpholin-4-ylsulfonyl)phenyl]amino}pyrimidin-4-yl)amino]cyclobut-3-ene-1,2-dione;

3-(tert-butylamino)-4-[(2-{[3-(morpholin-4-ylsulfonyl)phenyl]amino}pyrimidin-4-yl)amino]cyclobut-3-ene-1,2-dione;

3-(tert-butylamino)-4-({2-[(2-methyl-1H-benzimidazol-6-yl)amino]pyrimidin-4-yl}amino)cyclobut-3-ene-1,2-dione;

3-(tert-butylamino)-4-{[2-({1-[(4-methylphenyl)sulfonyl]-1H-indol-5-yl}amino)pyrimidin-4-yl]amino}cyclobut-3-ene-1,2-dione;

3-(tert-butylamino)-4-[(2-{[1-(methylsulfonyl)-2,3-dihydro-1H-indol-5-yl]amino}pyrimidin-4-yl)amino]cyclobut-3-ene-1,2-dione;

3-(tert-butylamino)-4-({2-[(4-pyridin-2-ylphenyl)amino]pyrimidin-4-yl}amino)cyclobut-3-ene-1,2-dione;

3-(tert-butylamino)-4-{[2-({4-[4-(methylsulfonyl)piperazin-1-yl]phenyl}amino)pyrimidin-4-yl]amino}cyclobut-3-ene-1,2-dione;

3-(tert-butylamino)-4-[(2-{[3-(1H-pyrrol-1-yl)phenyl]amino}pyrimidin-4-yl)amino]cyclobut-3-ene-1,2-dione;

3-(tert-butylamino)-4-({2-[(2-methyl-1,3-benzothiazol-6-yl)amino]pyrimidin-4-yl}amino)cyclobut-3-ene-1,2-dione;

3-(tert-butylamino)-4-[(2-{[4-(1,3-oxazol-5-yl)phenyl]amino}pyrimidin-4-yl)amino]cyclobut-3-ene-1,2-dione;

3-(tert-butylamino)-4-{[2-(pyridin-4-ylamino)pyrimidin-4-yl]amino}cyclobut-3-ene-1,2-dione;

3-(tert-butylamino)-4-{[2-({4-[(dimethylamino)methyl]phenyl}amino)pyrimidin-4-yl]amino}cyclobut-3-ene-1,2-dione;

5-[(4-{[2-(tert-butylamino)-3,4-dioxocyclobut-1-en-1-yl]amino}pyrimidin-2-yl)amino]-2-methyl-1H-isoindole-1,3(2H)-dione;

3-(tert-butylamino)-4-({6-[(4-iodophenyl)amino]pyrimidin-4-yl}amino)cyclobut-3-ene-1,2-dione;

3-(cyclopropylamino)-4-({2-[(4-iodophenyl)amino]pyrimidin-4-yl}amino)cyclobut-3-ene-1,2-dione;

3-(cyclobutylamino)-4-({2-[(4-iodophenyl)amino]pyrimidin-4-yl}amino)cyclobut-3-ene-1,2-dione;

3-(cyclobutylamino)-4-({2-[(4-pyridin-4-ylphenyl)amino]pyrimidin-4-yl}amino)cyclobut-3-ene-1,2-dione;

4'-[(4-{[2-(tert-butylamino)-3,4-dioxocyclobut-1-en-1-yl]amino}pyrimidin-2-yl)amino]-N,N-dimethyl-1,1'-biphenyl-4-carboxamide;

3-(tert-butylamino)-4-({6-methyl-2-[(4-thien-3-ylphenyl)amino]pyrimidin-4-yl}amino)cyclobut-3-ene-1,2-dione;

3-[(4-{[2-(tert-butylamino)-3,4-dioxocyclobut-1-en-1-yl]amino}pyrimidin-2-yl)amino]benzenesulfonamide;

3-(tert-butylamino)-4-({2-[(3-methoxyphenyl)amino]pyrimidin-4-yl}amino)cyclobut-3-ene-1,2-dione;
3-[(2-{[4-(4-benzylpiperazin-1-yl)phenyl]amino}pyrimidin-4-yl)amino]-4-(tert-butylamino)cyclobut-3-ene-1,2-dione;
3-(tert-butylamino)-4-({2-[(4-nitrophenyl)amino]pyrimidin-4-yl}amino)cyclobut-3-ene-1,2-dione;
3-(tert-butylamino)-4-({2-[(6-chloro-5-methylpyridin-3-yl)amino]pyrimidin-4-yl}amino)cyclobut-3-ene-1,2-dione;
4-[(4-{[2-(tert-butylamino)-3,4-dioxocyclobut-1-en-1-yl]amino}pyrimidin-2-yl)amino]-3-methoxy-N-piperidin-4-ylbenzamide;
3-{[(1R)-1-cyclohexylethyl]amino}-4-({2-[(4-thien-3-ylphenyl)amino]pyrimidin-4-yl}amino)cyclobut-3-ene-1,2-dione;
3-{[(1S)-1-cyclohexylethyl]amino}-4-[(2-{[4-(4,6-dimethoxypyrimidin-2-yl)phenyl]amino}pyrimidin-4-yl)amino]cyclobut-3-ene-1,2-dione;
3-{[(1R)-1-cyclohexylethyl]amino}-4-[(2-{[4-(4,6-dimethoxypyrimidin-2-yl)phenyl]amino}pyrimidin-4-yl)amino]cyclobut-3-ene-1,2-dione;
3-{[(1S)-1-cyclohexylethyl]amino}-4-({2-[(4-pyridin-4-ylphenyl)amino]pyrimidin-4-yl}amino)cyclobut-3-ene-1,2-dione;
3-{[(1R)-1-cyclohexylethyl]amino}-4-({2-[(4-pyridin-4-ylphenyl)amino]pyrimidin-4-yl}amino)cyclobut-3-ene-1,2-dione;
3-(tert-butylamino)-4-[(2-{[4-(1-methylpiperidin-4-yl)phenyl]amino}pyrimidin-4-yl)amino]cyclobut-3-ene-1,2-dione;
3-(piperidin-4-ylamino)-4-({2-[(4-pyridin-4-ylphenyl)amino]pyrimidin-4-yl}amino)cyclobut-3-ene-1,2-dione;
3-[(4-{[2-(tert-butylamino)-3,4-dioxocyclobut-1-en-1-yl]amino}pyrimidin-2-yl)amino]-N-(1-methylpiperidin-4-yl)benzamide;
3-[(4-{[2-(tert-butylamino)-3,4-dioxocyclobut-1-en-1-yl]amino}pyrimidin-2-yl)amino]benzoic acid;
3-[(4-{[2-(tert-butylamino)-3,4-dioxocyclobut-1-en-1-yl]amino}pyrimidin-2-yl)amino]-N-cycloheptylbenzamide;
3-[(4-{[2-(tert-butylamino)-3,4-dioxocyclobut-1-en-1-yl]amino}pyrimidin-2-yl)amino]-N-cyclohexylbenzamide;
3-[(4-{[2-(tert-butylamino)-3,4-dioxocyclobut-1-en-1-yl]amino}pyrimidin-2-yl)amino]-N-cyclopentylbenzamide;
3-[(4-{[2-(tert-butylamino)-3,4-dioxocyclobut-1-en-1-yl]amino}pyrimidin-2-yl)amino]-N-cyclobutylbenzamide;
3-[(4-{[2-(tert-butylamino)-3,4-dioxocyclobut-1-en-1-yl]amino}pyrimidin-2-yl)amino]-N-cyclohexyl-4-methoxybenzamide;
3-[(4-{[2-(tert-butylamino)-3,4-dioxocyclobut-1-en-1-yl]amino}pyrimidin-2-yl)amino]-4-methoxybenzoic acid;
3-(tert-butylamino)-4-{[2-(quinolin-6-ylamino)pyrimidin-4-yl]amino}cyclobut-3-ene-1,2-dione;
3-({2-[(4-fluoro-3-methylphenyl)amino]pyrimidin-4-yl}amino)-4-{[(1R)-1,2,2-trimethylpropyl]amino}cyclobut-3-ene-1,2-dione;
3-(tert-butylamino)-4-({5-fluoro-2-[(2'-methoxy-1,1'-biphenyl-4-yl)amino]pyrimidin-4-yl}amino)cyclobut-3-ene-1,2-dione;
N-cyclobutyl-4-{[4-({2-[(2-(hydroxy-1,1-dimethylethyl)amino]-3,4-dioxocyclobut-1-en-1-yl}amino)pyrimidin-2-yl]amino}-3-methoxybenzamide;
N-cyclobutyl-3-methoxy-4-{[4-({2-[(1-methyl-1-phenylethyl)amino]-3,4-dioxocyclobut-1-en-1-yl}amino)pyrimidin-2-yl]amino}benzamide;
N-cyclobutyl-4-{[4-({2-[(1,1-dimethylprop-2-ynyl)amino]-3,4-dioxocyclobut-1-en-1-yl}amino)pyrimidin-2-yl]amino}-3-methoxybenzamide;
4-{[4-({2-[(1-cyano-1-methylethyl)amino]-3,4-dioxocyclobut-1-en-1-yl}amino)pyrimidin-2-yl]amino}-N-cyclobutyl-3-methoxybenzamide;
N-cyclobutyl-4-{[4-({2-[(1-cyclopropyl-1-methylethyl)amino]-3,4-dioxocyclobut-1-en-1-yl}amino)pyrimidin-2-yl]amino}-3-methoxybenzamide;
N-cyclobutyl-4-{[4-({2-[(1,1-dimethyl-2-morpholin-4-ylethyl)amino]-3,4-dioxocyclobut-1-en-1-yl}amino)pyrimidin-2-yl]amino}-3-methoxybenzamide;
N-cyclobutyl-4-{[4-({2-[(1,1-dimethyl-3-oxobutyl)amino]-3,4-dioxocyclobut-1-en-1-yl}amino)pyrimidin-2-yl]amino}-3-methoxybenzamide;
N-cyclobutyl-4-[(4-{[3,4-dioxo-2-(propylamino)cyclobut-1-en-1-yl]amino}pyrimidin-2-yl)amino]-3-methoxybenzamide;
4-({4-[(2-anilino-3,4-dioxocyclobut-1-en-1-yl)amino]pyrimidin-2-yl}amino)-N-cyclobutyl-3-methoxybenzamide;
N-cyclopentyl-4-[(4-{[2-(diethylamino)-3,4-dioxocyclobut-1-en-1-yl]amino}pyrimidin-2-yl)amino]-3-methoxybenzamide;
2-{4-[(4-{[2-(tert-butylamino)-3,4-dioxocyclobut-1-en-1-yl]amino}pyrimidin-2-yl)amino]phenyl}-N-(1-methylpiperidin-4-yl)acetamide;
2-{4-[(4-{[2-(tert-butylamino)-3,4-dioxocyclobut-1-en-1-yl]amino}pyrimidin-2-yl)amino]phenyl}-N-(pyridin-3-ylmethyl)acetamide;
2-{3-[(4-{[2-(tert-butylamino)-3,4-dioxocyclobut-1-en-1-yl]amino}pyrimidin-2-yl)amino]phenyl}-N-(1-methylpiperidin-4-yl)acetamide;
2-{3-[(4-{[2-(tert-butylamino)-3,4-dioxocyclobut-1-en-1-yl]amino}pyrimidin-2-yl)amino]phenyl}-N-cyclobutylacetamide;
3-(tert-butylamino)-4-[(2-{[4-(pyridin-2-ylethynyl)phenyl]amino}pyrimidin-4-yl)amino]cyclobut-3-ene-1,2-dione;
3-(tert-butylamino)-4-({2-[(4-pent-1-ynylphenyl)amino]pyrimidin-4-yl}amino)cyclobut-3-ene-1,2-dione;
3-(tert-butylamino)-4-{[2-({4-[3-(diethylamino)prop-1-ynyl]phenyl}amino)pyrimidin-4-yl]amino}cyclobut-3-ene-1,2-dione;
3-(tert-butylamino)-4-{[2-({4-[(1E)-4-hydroxybut-1-enyl]phenyl}amino)pyrimidin-4-yl]amino}cyclobut-3-ene-1,2-dione;
3-(tert-butylamino)-4-{[2-({4-[(E)-2-pyridin-2-ylvinyl]phenyl}amino)pyrimidin-4-yl]amino}cyclobut-3-ene-1,2-dione;
3-(tert-butylamino)-4-{[2-({4-[(1E)-pent-1-enyl]phenyl}amino)pyrimidin-4-yl]amino}cyclobut-3-ene-1,2-dione;
N-{4-[(4-{[2-(tert-butylamino)-3,4-dioxocyclobut-1-en-1-yl]amino}pyrimidin-2-yl)amino]-3-methoxyphenyl}cyclopentanecarboxamide;
3-({2-[(4-amino-2-methoxyphenyl)amino]pyrimidin-4-yl}amino)-4-(tert-butylamino)cyclobut-3-ene-1,2-dione;
6-[(4-{[2-(tert-butylamino)-3,4-dioxocyclobut-1-en-1-yl]amino}pyrimidin-2-yl)amino]-N-cyclopentylnicotinamide;

4-[(4-{[2-(tert-butylamino)-3,4-dioxocyclobut-1-en-1-yl]amino}pyrimidin-2-yl)amino]-N-cyclopentyl-3-fluorobenzamide;

4-[(4-{[2-(tert-butylamino)-3,4-dioxocyclobut-1-en-1-yl]amino}pyrimidin-2-yl)amino]benzoic acid;

4-[(4-{[2-(tert-butylamino)-3,4-dioxocyclobut-1-en-1-yl]amino}pyrimidin-2-yl)amino]-N-[(1R)-1-(hydroxymethyl)-3-methylbutyl]benzamide;

N-2-{4-[(4-{[2-(tert-butylamino)-3,4-dioxocyclobut-1-en-1-yl]amino}pyrimidin-2-yl)amino]benzoyl}-L-leucinamide;

4-[(4-{[2-(tert-butylamino)-3,4-dioxocyclobut-1-en-1-yl]amino}pyrimidin-2-yl)amino]-N-[(1S)-2-hydroxy-1-phenylethyl]benzamide;

4-[(4-{[2-(tert-butylamino)-3,4-dioxocyclobut-1-en-1-yl]amino}pyrimidin-2-yl)amino]-N-(3-ethoxypropyl)benzamide;

4-[(4-{[2-(tert-butylamino)-3,4-dioxocyclobut-1-en-1-yl]amino}pyrimidin-2-yl)amino]-N-[3-(methylthio)propyl]benzamide;

4-[(4-{[2-(tert-butylamino)-3,4-dioxocyclobut-1-en-1-yl]amino}pyrimidin-2-yl)amino]-N-[4-(dimethylamino)butyl]benzamide;

4-[(4-{[2-(tert-butylamino)-3,4-dioxocyclobut-1-en-1-yl]amino}pyrimidin-2-yl)amino]-N-(2-phenoxyethyl)benzamide;

4-[(4-{[2-(tert-butylamino)-3,4-dioxocyclobut-1-en-1-yl]amino}pyrimidin-2-yl)amino]-N-[3-(2-oxopyrrolidin-1-yl)propyl]benzamide;

4-[(4-{[2-(tert-butylamino)-3,4-dioxocyclobut-1-en-1-yl]amino}pyrimidin-2-yl)amino]-N-(3,4-difluorobenzyl)benzamide;

N-{2-[4-(aminosulfonyl)phenyl]ethyl}-4-[(4-{[2-(tert-butylamino)-3,4-dioxocyclobut-1-en-1-yl]amino}pyrimidin-2-yl)amino]benzamide;

4-[(4-{[2-(tert-butylamino)-3,4-dioxocyclobut-1-en-1-yl]amino}pyrimidin-2-yl)amino]-N-(pyridin-2-ylmethyl)benzamide;

4-[(4-{[2-(tert-butylamino)-3,4-dioxocyclobut-1-en-1-yl]amino}pyrimidin-2-yl)amino]-N-[2-(1H-imidazol-4-yl)ethyl]benzamide;

4-[(4-{[2-(tert-butylamino)-3,4-dioxocyclobut-1-en-1-yl]amino}pyrimidin-2-yl)amino]-N-(2-morpholin-4-yl-ethyl)benzamide;

4-[(4-{[2-(tert-butylamino)-3,4-dioxocyclobut-1-en-1-yl]amino}pyrimidin-2-yl)amino]-3-methoxybenzoic acid;

4-[(4-{[2-(tert-butylamino)-3,4-dioxocyclobut-1-en-1-yl]amino}pyrimidin-2-yl)amino]-N-[4-(dimethylamino)cyclohexyl]-3-methoxybenzamide;

4-[(4-{[2-(tert-butylamino)-3,4-dioxocyclobut-1-en-1-yl]amino}pyrimidin-2-yl)amino]-N-(1,1-dimethyl-2-morpholin-4-ylethyl)-3-methoxybenzamide;

4-[(4-{[2-(tert-butylamino)-3,4-dioxocyclobut-1-en-1-yl]amino}pyrimidin-2-yl)amino]-N-(1-ethylpiperidin-3-yl)-3-methoxybenzamide; and 4-[(4-{[2-(tert-butylamino)-3,4-dioxocyclobut-1-en-1-yl]amino}pyrimidin-2-yl)amino]-N-cyclobutyl-3-(trifluoromethoxy)benzamide.

* * * * *

UNITED STATES PATENT AND TRADEMARK OFFICE
CERTIFICATE OF CORRECTION

PATENT NO. : 7,956,185 B2 Page 1 of 1
APPLICATION NO. : 11/753279
DATED : June 7, 2011
INVENTOR(S) : Diebold et al.

It is certified that error appears in the above-identified patent and that said Letters Patent is hereby corrected as shown below:

Column 71, line 10, claim 1: "$R^9$ cycloalkyl" to read as --$R^9$ is cycloalkyl--

Column 71, line 34, claim 1: "$R^{31}$" to read as --$R^{30}$--

Column 77, line 14, claim 7: before "3-{[(1R)-1-cyclohexylethyl]amino}-4-({2-[(4-thien-3-ylphenyl)amino]pyrimidin-4-yl}amino)cyclobut-3-ene-1,2-dione;" insert --3-{[(1S)-1-cyclohexylethyl]amino}-4-({2-[(4-thien-3-ylphenyl)amino]pyrimidin-4-yl}amino)cyclobut-3-ene-1,2-dione;--

Signed and Sealed this
Twenty-ninth Day of May, 2012

David J. Kappos
*Director of the United States Patent and Trademark Office*